US012665123B2

(12) United States Patent
Ridler et al.

(10) Patent No.: US 12,665,123 B2
(45) Date of Patent: *Jun. 23, 2026

(54) INDUCTANCE COIL WITH VARIED GEOMETRY

(71) Applicant: Cochlear Limited, Macquarie University (AU)

(72) Inventors: Oliver John Ridler, Cherrybrook (AU); Patrik Kennes, Mechelen (BE); Kurt Forrester, Bangor (AU)

(73) Assignee: Cochlear Limited, Macquarie University (AU)

( * ) Notice: Subject to any disclaimer, the term of this patent is extended or adjusted under 35 U.S.C. 154(b) by 479 days.

This patent is subject to a terminal disclaimer.

(21) Appl. No.: 17/828,385

(22) Filed: May 31, 2022

(65) Prior Publication Data

US 2022/0293330 A1 Sep. 15, 2022

Related U.S. Application Data

(63) Continuation of application No. 16/907,990, filed on Jun. 22, 2020, now Pat. No. 11,348,720, which is a
(Continued)

(51) Int. Cl.
*H01Q 1/22* (2006.01)
*A61N 1/372* (2006.01)
(Continued)

(52) U.S. Cl.
CPC ..... *H01F 27/2804* (2013.01); *A61N 1/37229* (2013.01); *H01F 5/003* (2013.01);
(Continued)

(58) Field of Classification Search
CPC .. H01F 27/2804; H01Q 1/2291; H01Q 1/248; H01Q 1/273; H01Q 1/36; H01Q 7/00; H01Q 21/28
See application file for complete search history.

(56) References Cited

U.S. PATENT DOCUMENTS 3,656,168 A 4/1972 Stropki
5,610,433 A 3/1997 Merrill et al.
(Continued)

FOREIGN PATENT DOCUMENTS

CN 101599574 A 12/2009
CN 201868563 U 6/2011
(Continued)

OTHER PUBLICATIONS

International Search Report and Written Opinion for PCT/IB2016/056436, mailed Feb. 6, 2017.
(Continued)

*Primary Examiner* — Hoang V Nguyen
(74) *Attorney, Agent, or Firm* — Pilloff Passino & Cosenza LLP; Martin J. Cosenza

(57) ABSTRACT

An inductance communication coil, including a conductor having at least one conductive turn, wherein a width of the conductor is wider at a first location relative to that at a second location. The conductor can be made out of metal. In some embodiments, the first location and the second location are on the same turn. In some embodiments, the conductor includes a plurality of turns, wherein the first location is at a first turn and the second location is at a second turn.

16 Claims, 41 Drawing Sheets

Related U.S. Application Data continuation of application No. 15/334,950, filed on Oct. 26, 2016, now Pat. No. 10,692,642.

(60) Provisional application No. 62/246,848, filed on Oct. 27, 2015.

(51) Int. Cl.

| | |
|---|---|
| *H01F 5/00* | (2006.01) |
| *H01F 27/00* | (2006.01) |
| *H01F 27/28* | (2006.01) |
| *H01F 38/14* | (2006.01) |
| *H01Q 1/24* | (2006.01) |
| *H01Q 1/27* | (2006.01) |
| *H01Q 1/36* | (2006.01) |
| *H01Q 1/38* | (2006.01) |
| *H01Q 7/00* | (2006.01) |
| *H01Q 21/28* | (2006.01) |
| *H02J 7/42* | (2026.01) |
| *H02J 50/00* | (2016.01) |
| *H02J 50/10* | (2016.01) |
| *H04R 25/00* | (2006.01) |
| *A61N 1/36* | (2006.01) |
| *A61N 1/378* | (2006.01) |

(52) U.S. Cl.

CPC ....... *H01F 27/006* (2013.01); *H01F 27/2871* (2013.01); *H01F 38/14* (2013.01); *H01Q 1/2291* (2013.01); *H01Q 1/248* (2013.01); *H01Q 1/273* (2013.01); *H01Q 1/36* (2013.01); *H01Q 1/38* (2013.01); *H01Q 7/00* (2013.01); *H01Q 21/28* (2013.01); *H02J 7/42* (2026.01); *H02J 50/005* (2020.01); *H02J 50/10* (2016.02); *H04R 25/505* (2013.01); *H04R 25/554* (2013.01); *A61N 1/36038* (2017.08); *A61N 1/3787* (2013.01); *H04R 2225/43* (2013.01); *H04R 2225/51* (2013.01); *H04R 2225/67* (2013.01)

(56) References Cited

U.S. PATENT DOCUMENTS

| | | | |
|---|---|---|---|
| 7,260,435 | B2 | 8/2007 | Ibrahim |
| 7,973,635 | B2 | 7/2011 | Baarman et al. |
| 8,126,563 | B2 | 2/2012 | Ibrahim |
| 8,410,636 | B2 | 4/2013 | Kurs et al. |
| 8,538,545 | B2 | 9/2013 | Meskens |
| 8,749,337 | B2 | 6/2014 | Baram et al. |
| 8,773,232 | B2 | 7/2014 | Kato |
| 8,829,734 | B2 | 9/2014 | Gulak et al. |
| 2003/0202937 | A1* | 10/2003 | Sabbadini .............. G01N 33/60 424/9.34 |
| 2009/0085706 | A1 | 4/2009 | Baarman et al. |
| 2009/0227829 | A1* | 9/2009 | Burnett ................... A61N 2/02 600/15 |
| 2009/0295658 | A1 | 12/2009 | Ki |
| 2011/0009924 | A1* | 1/2011 | Meskens ............ A61N 1/36038 607/57 |
| 2011/0266883 | A1 | 11/2011 | Eray |
| 2012/0130206 | A1 | 5/2012 | Vajha et al. |
| 2012/0249276 | A1 | 10/2012 | Fontana et al. |
| 2012/0326931 | A1 | 12/2012 | Murayama et al. |
| 2013/0069445 | A1 | 3/2013 | Waffenschmidt |
| 2013/0069749 | A1 | 3/2013 | Singh et al. |
| 2013/0201589 | A1 | 8/2013 | Singh et al. |
| 2014/0152118 | A1 | 6/2014 | Kim |
| 2015/0187484 | A1 | 7/2015 | Jeong et al. |
| 2015/0265842 | A1 | 9/2015 | Ridler et al. |
| 2015/0283313 | A1 | 10/2015 | Huber |
| 2015/0325362 | A1 | 11/2015 | Kumura et al. |
| 2017/0117086 | A1 | 4/2017 | Ridler et al. |
| 2017/0117087 | A1 | 4/2017 | Ridler et al. |

FOREIGN PATENT DOCUMENTS

| | | |
|---|---|---|
| CN | 103298523 A | 9/2013 |
| CN | 104752817 A | 7/2015 |

OTHER PUBLICATIONS

Uei-Ming Jow et al., "Design and Optimization of Printed Spiral Coils for Efficient Transcutaneous Inductive Power Transmission," IEEE Transactions on Biomedical Circuits and Systems, Sep. 2007, vol. 1, No. 3.

Hao Ma et al., "An Improved Multi-layer PCB Winding and Circuit Design for Universal Contactless Charging Platform," 36th Annual Conference on IEEE Industrial Electronics, Nov. 2010, pp. 1,763-1,768.

Sidharth Dalmia et al., "High-Q RF Passives on Organic Substrates Using a Low-Cost Low-Temperature Laminate Process," SPIE Proceedings, Mar. 19, 2002, vol. 4,755.

Cam Nguyen, "Radio-Frequency Integrated-Circuit Engineering," Mar. 2015, p. 53, Wiley.

Integrated Circuit Inductors, https://www.physicsforums.com/threads/q-integrated-circuit-inductors.655401/, accessed Jan. 2016.

Extended European Search Report for European Patent Application No. 16 859 166.7, mailed May 3, 2019.

* cited by examiner

Figure 2A:
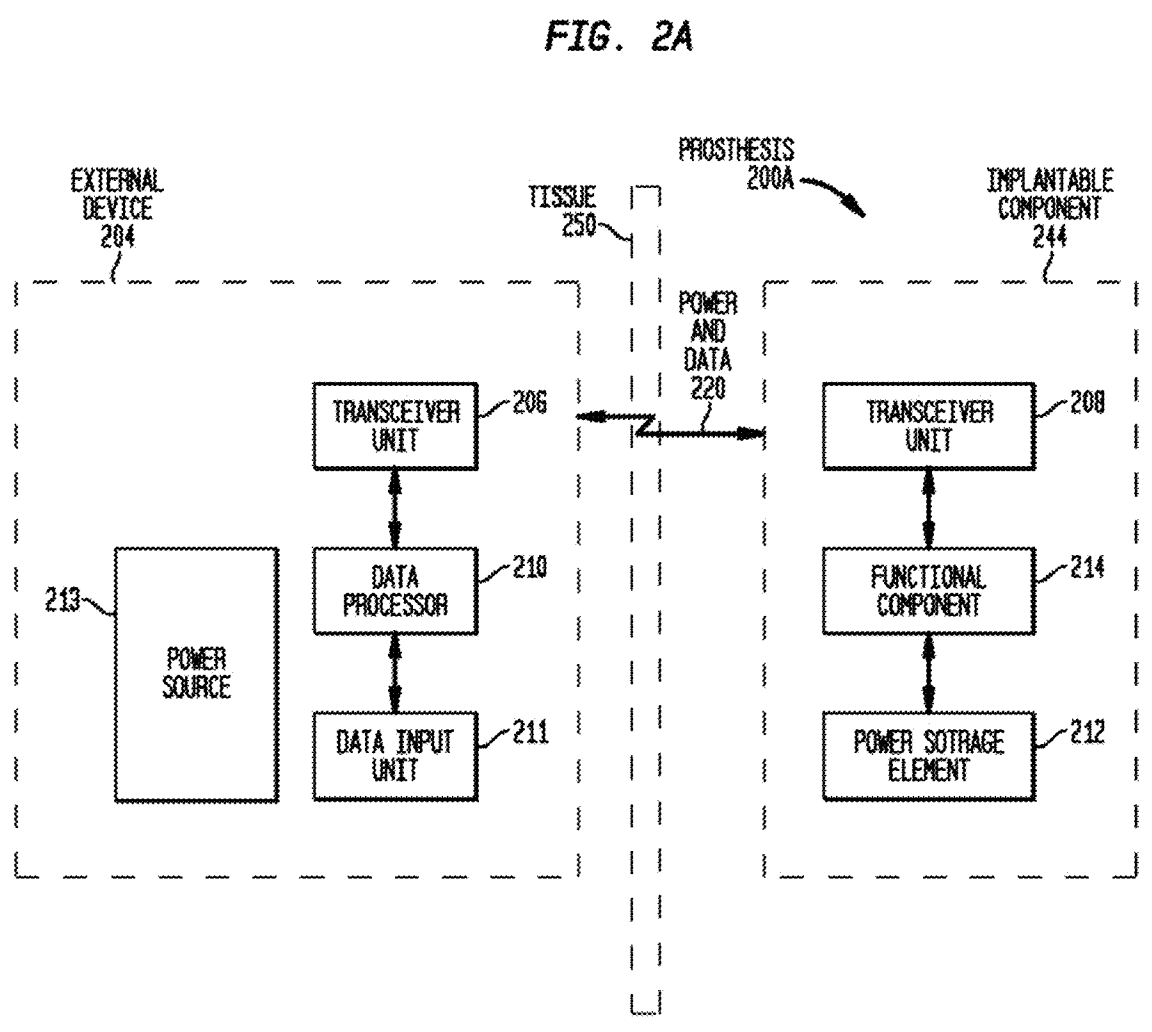

PROSTHESIS 200A

INPLANTABLE COMPONENT 244

TRANSCEIVER UNIT 208

FUNCTIONAL COMPONENT 214

POWER STORAGE ELEMENT 212

POWER AND DATA 220

TISSUE 250

EXTERNAL DEVICE 204

TRANSCEIVER UNIT 206

DATA PROCESSOR 210

DATA INPUT UNIT 211

POWER SOURCE 213

*FIG. 4B*

INDUCTIVE COMMUNICATION COMPONENT 416

TRANSMITTER UNIT 406B

POWER TRANSMITTER 412B

DATA TRANSMITTER 414B

FIG. 8

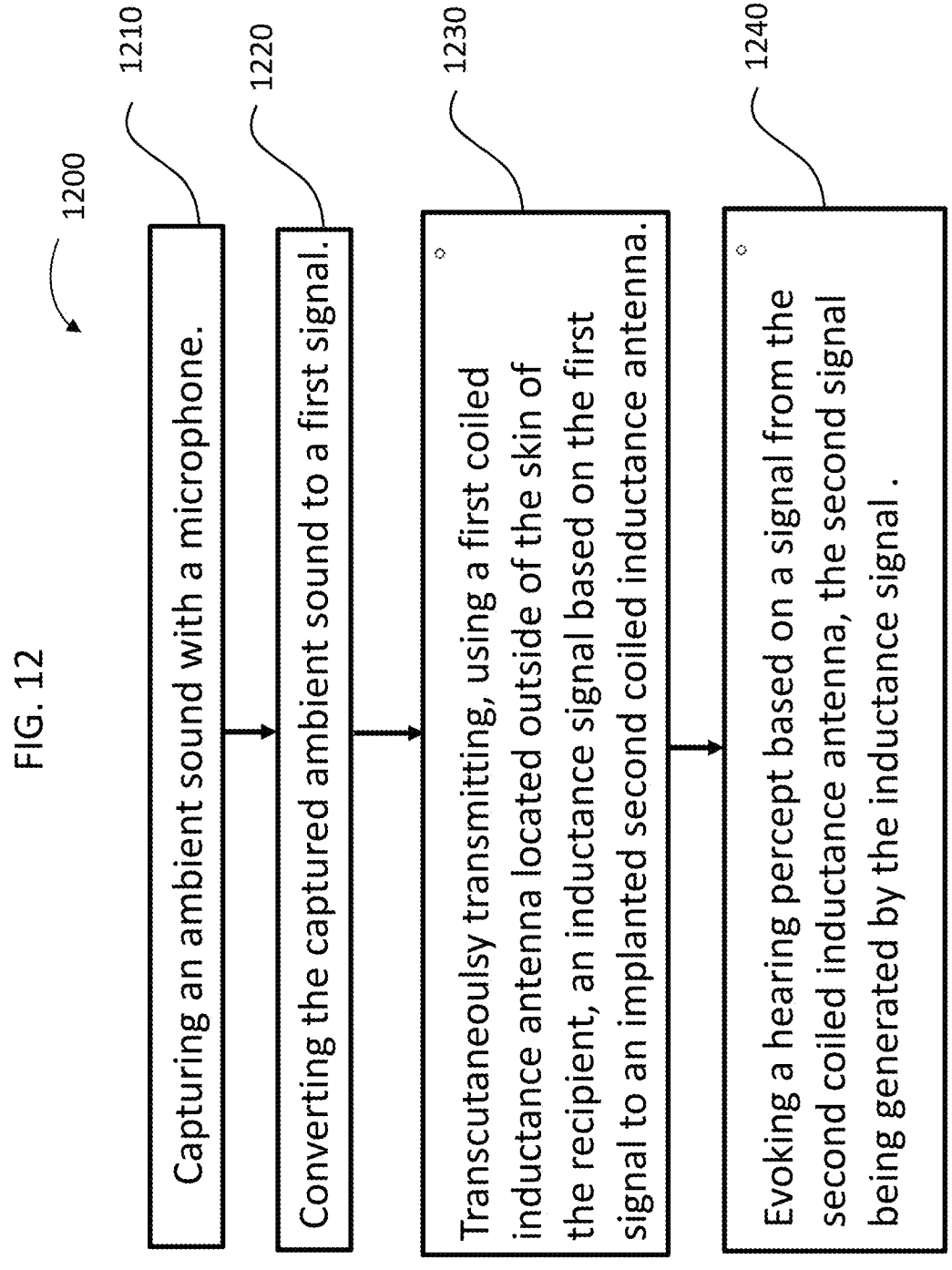

Capturing an ambient sound with a microphone.

1220

Converting the captured ambient sound to a first signal.

1230

Transcutaneoulsy transmitting, using a first coiled inductance antenna located outside of the skin of the recipient, an inductance signal based on the first signal to an implanted second coiled inductance antenna.

1240

Evoking a hearing percept based on a signal from the second coiled inductance antenna, the second signal being generated by the inductance signal .

FIG. 13

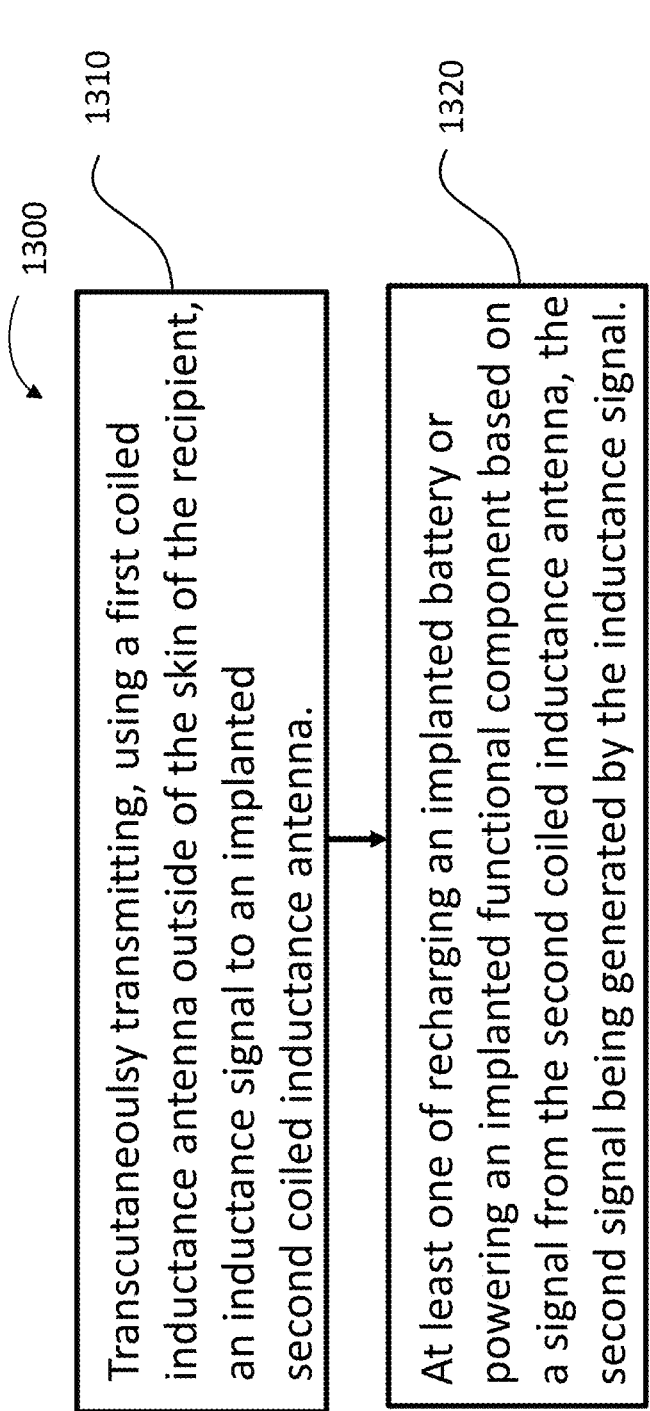

1300

1310

Transcutaneoulsy transmitting, using a first coiled inductance antenna outside of the skin of the recipient, an inductance signal to an implanted second coiled inductance antenna.

1320

At least one of recharging an implanted battery or powering an implanted functional component based on a signal from the second coiled inductance antenna, the second signal being generated by the inductance signal.

Figure 20:
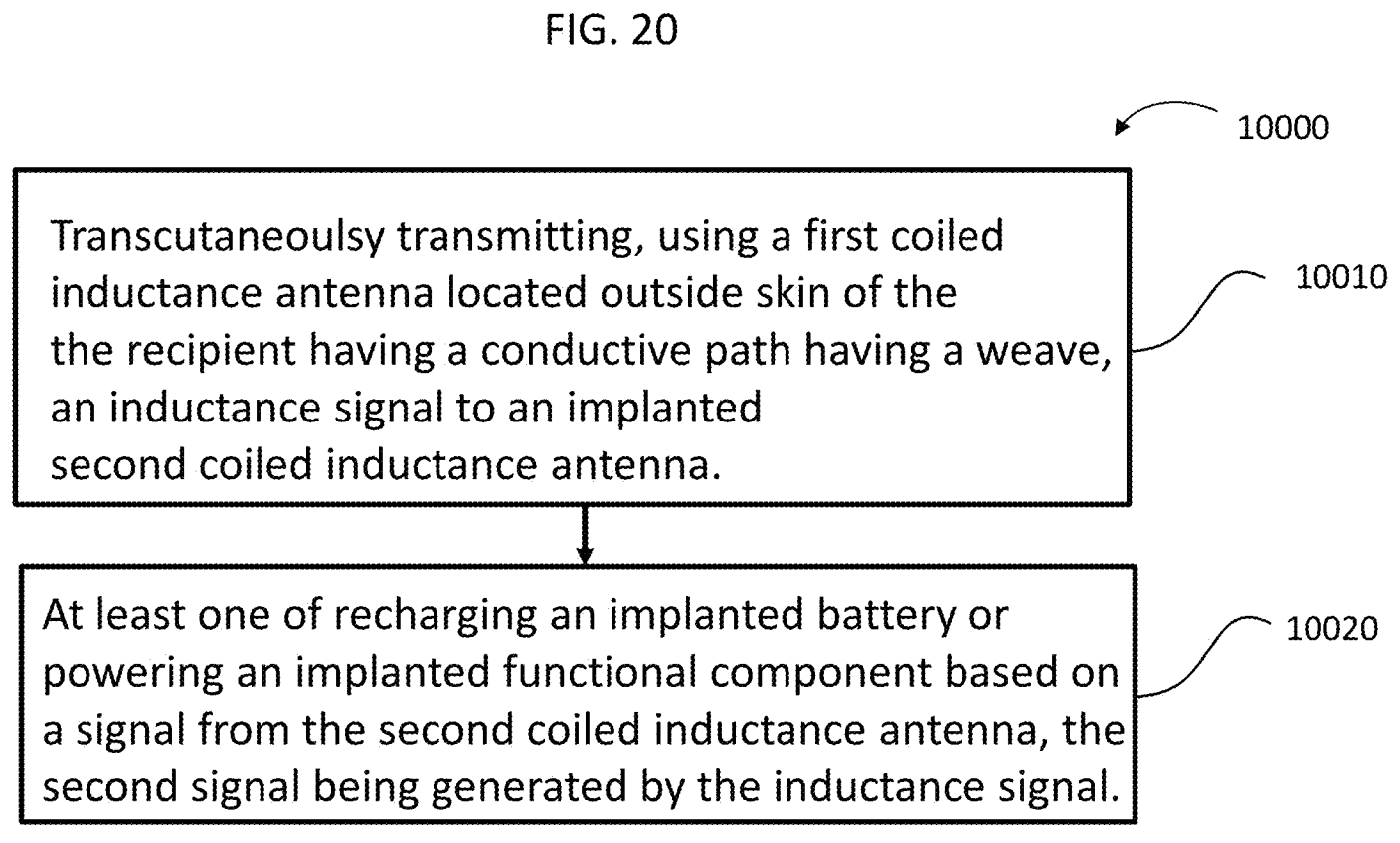

Transcutaneoulsy transmitting, using a first coiled inductance antenna located outside skin of the the recipient having a conductive path having a weave, an inductance signal to an implanted second coiled inductance antenna.

10020

At least one of recharging an implanted battery or powering an implanted functional component based on a signal from the second coiled inductance antenna, the second signal being generated by the inductance signal.

FIG. 23

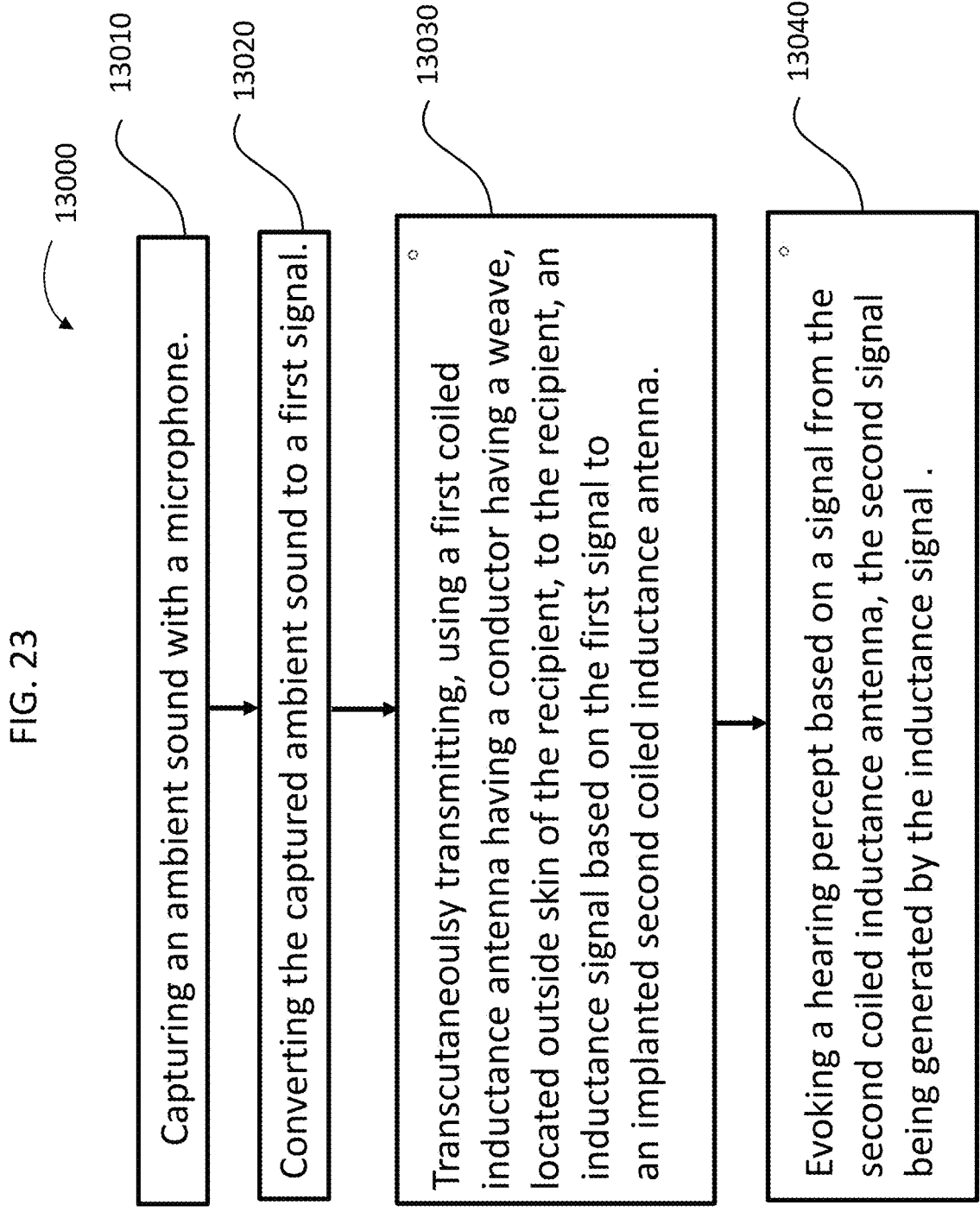

13000

13010
Capturing an ambient sound with a microphone.

13020
Converting the captured ambient sound to a first signal.

13030
Transcutaneoulsy transmitting, using a first coiled inductance antenna having a conductor having a weave, located outside skin of the recipient, to the recipient, an inductance signal based on the first signal to an implanted second coiled inductance antenna.

13040
Evoking a hearing percept based on a signal from the second coiled inductance antenna, the second signal being generated by the inductance signal.

INDUCTANCE COIL WITH VARIED GEOMETRY

CROSS-REFERENCE TO RELATED APPLICATIONS

This application is a Continuation application of U.S. patent application Ser. No. 16/907,990, filed Jun. 22, 2020, which is a Continuation application of U.S. patent application Ser. No. 15/334,950, filed Oct. 26, 2016 (now U.S. Pat. No. 10,692,642), which claims priority to Provisional U.S. Patent Application No. 62/246,848, entitled INDUCTANCE COIL WITH VARIED GEOMETRY, filed on Oct. 27, 2015, naming Oliver John RIDLER of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is an inductance communication coil, comprising a conductor having at least one conductive turn, wherein a width of the conductor is wider at a first location relative to that at a second location.

In accordance with another exemplary embodiment, there is a transcutaneous inductance communication antenna, comprising a conductor having a non-uniform geometry.

In accordance with another exemplary embodiment, there is a coiled conductor including at least three turns on a first layer, wherein a maximum outer diameter of the outermost turn of the at least three turns is about 30 mm, and the coiled conductor is of a configuration where a bare winding thereof, when subjected to an electrical current having a frequency of 5 MHz, has a Q factor of at least 75.

In accordance with another exemplary embodiment, there is a method, comprising transcutaneously transmitting, using a first coiled inductance antenna located outside the skin of the recipient, an inductance signal to an implanted second coiled inductance antenna and at least one of recharging an implanted battery or powering an implanted functional component based on a second signal from the second coiled inductance antenna, the second signal being generated by the inductance signal, wherein a current is applied to the first coiled inductance antenna to generate a magnetic field, thereby transmitting the inductance signal, and an average current density at least one of increases or decreases with distance from a geometric center of turns of the first coiled inductance antenna over at least a portion of the distance from the geometric center.

In accordance with another exemplary embodiment, there is an inductance coil, comprising a conductor having a plurality of turns, wherein DC resistance of the conductor varies along a path between a first location and a second location, wherein the plurality of turns are electrically located between the first location and the second location.

BRIEF DESCRIPTION OF THE DRAWINGS

Embodiments are described below with reference to the attached drawings, in which:

FIG. 1E is a side view of an exemplary hearing prosthesis in which at least some of the teachings detailed herein are applicable;

FIG. 2A is a functional block diagram of a prosthesis, in accordance with some embodiments;

FIG. 4B is a simplified schematic diagram of a transmitter unit of an external device in accordance with some embodiments;

FIG. 8 depicts an exemplary graph presenting data according to an exemplary embodiment;

FIG. 12 presents a flowchart for an exemplary schematic according to an exemplary embodiment;

FIG. 13 presents a flowchart for another exemplary schematic according to an exemplary embodiment;

FIG. 20 presents a flowchart for an exemplary schematic according to an exempla embodiment;

FIG. 23 presents a flowchart for an exemplary schematic according to an exemplary embodiment.

DETAILED DESCRIPTION

Exemplary embodiments will be described in terms of a cochlear implant. That said, it is noted that the teachings detailed herein and/or variations thereof can be utilized with other types of hearing prosthesis, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component (herein referred to as a medical device) having a coil that is implantable in a recipient. That said, the teachings detailed herein and variations thereof can also be applicable to non-medical device signal transfer, such as by way of example only and not by way of limitation, wireless power transfer between a charging station and a consumer electronic device. Any application to which the teachings detailed herein can be applicable can be included in some embodiments.

Figure 1A:
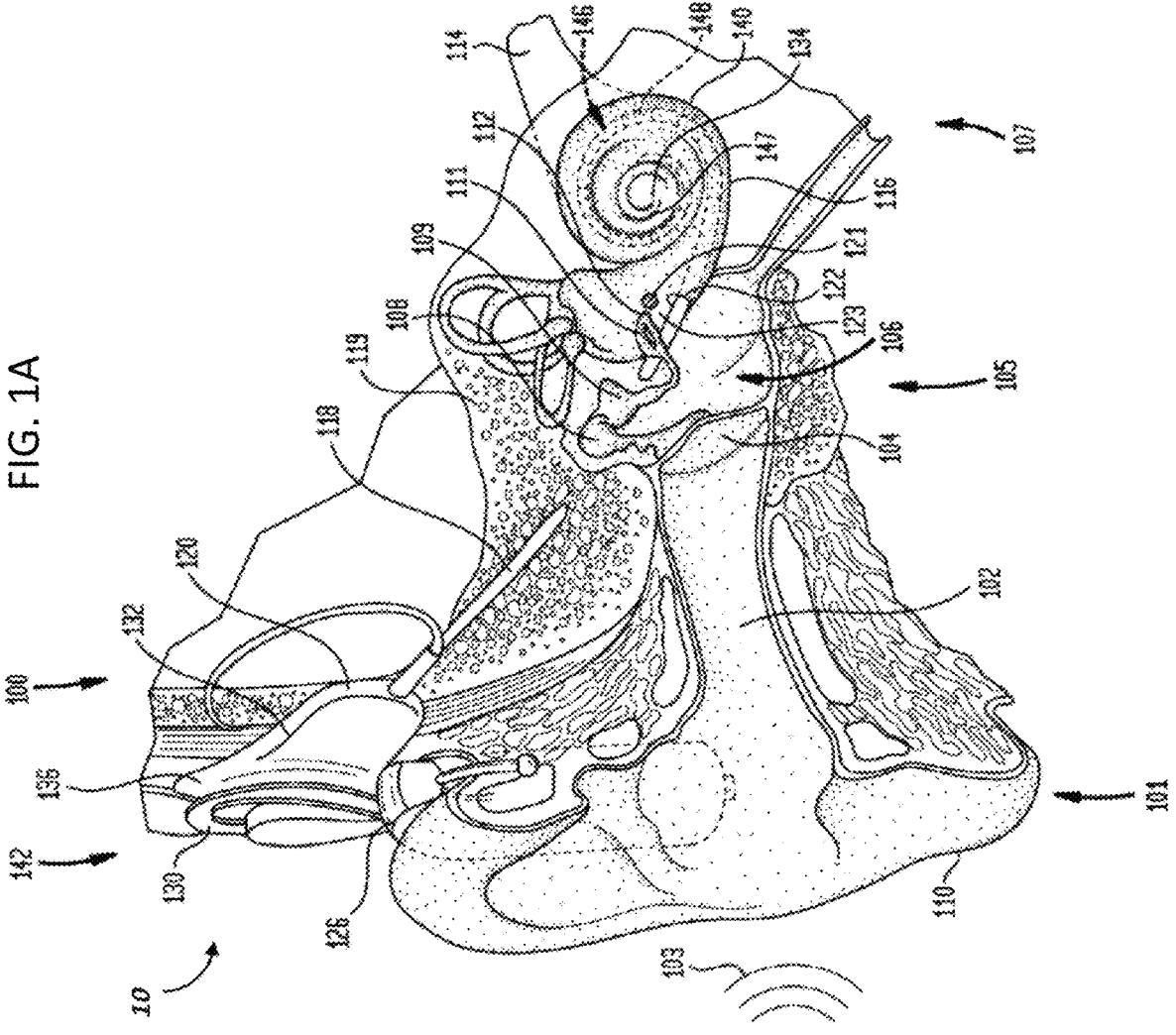
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prostheses, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100 (where the data can be used to evoke a hearing percept—even in "totally implantable" hearing prostheses, in some instances, there is utilitarian value in using an external microphone). In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. In an exemplary embodiment the external coil 130 can be a PCB based coil where the windings are copper traces formed on the PCB, as will be described in greater detail below.

External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises an internal coil assembly 136. Internal coil assembly 136 typically includes a wire antenna coil comprised of multiple turns of electrically insulated single-strand or multi-strand platinum or gold wire, as will be described in greater detail below. It is noted that in at least some exemplary embodiments, the internal coil assembly 136 is also a PCB based coil, while in other embodiments the internal coil assembly is not PCB based/it is not a PCB based coil. Thus, in an exemplary embodiment, there is a prostheses that includes an external component and an implantable component, wherein the two components are in transcutaneous signal communication with one another (e.g., RF signal communication, such as by way of example only and not by way of limitation, the communication that exists with respect to the cochlear implant detailed above and below), wherein the external component includes a PCB based coil according to the teachings detailed herein and/or variations thereof, and the implantable component includes a non-PCB based coil, which coils are utilized for the transcutaneous communication. It is also noted that in an exemplary embodiment, the coil of the external component is a two or more layer component, concomitant with the teachings as will be provided in greater detail below, while the coil of the implantable component that is in signal communication with the coil of the external component is a single layer coil where the loops of the coil are on one layer and on no other layer (i.e., all are on the same layer). In an exemplary embodiment, the coil of the external component corresponds to any of the teachings detailed herein, while the coil of the implantable component in signal communication with the coil of the external component is a coil made of a wire (as opposed to a printed conductor, etc.) having a round or rectangular cross-section (normal to the longitudinal axis of the wire), where the wire spirals inward no more two times, no more than three times or no more than four times/has no more than two, no more than three or no more than four tracks/turns. In an exemplary embodiment, the coil of the implantable component in signal communication with the external component has a constant cross-sectional shape and/or has a constant width. In this regard, in an exemplary embodiment, the coil of the external component is of a different configuration than the coil of the implantable component.

Cochlear implant 100 further comprises a main implantable component 120 and an elongate electrode assembly 118. Collectively, the coil assembly 136, the main implantable component 120, and the electrode assembly 118 correspond to the implantable component of the system 10.

In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
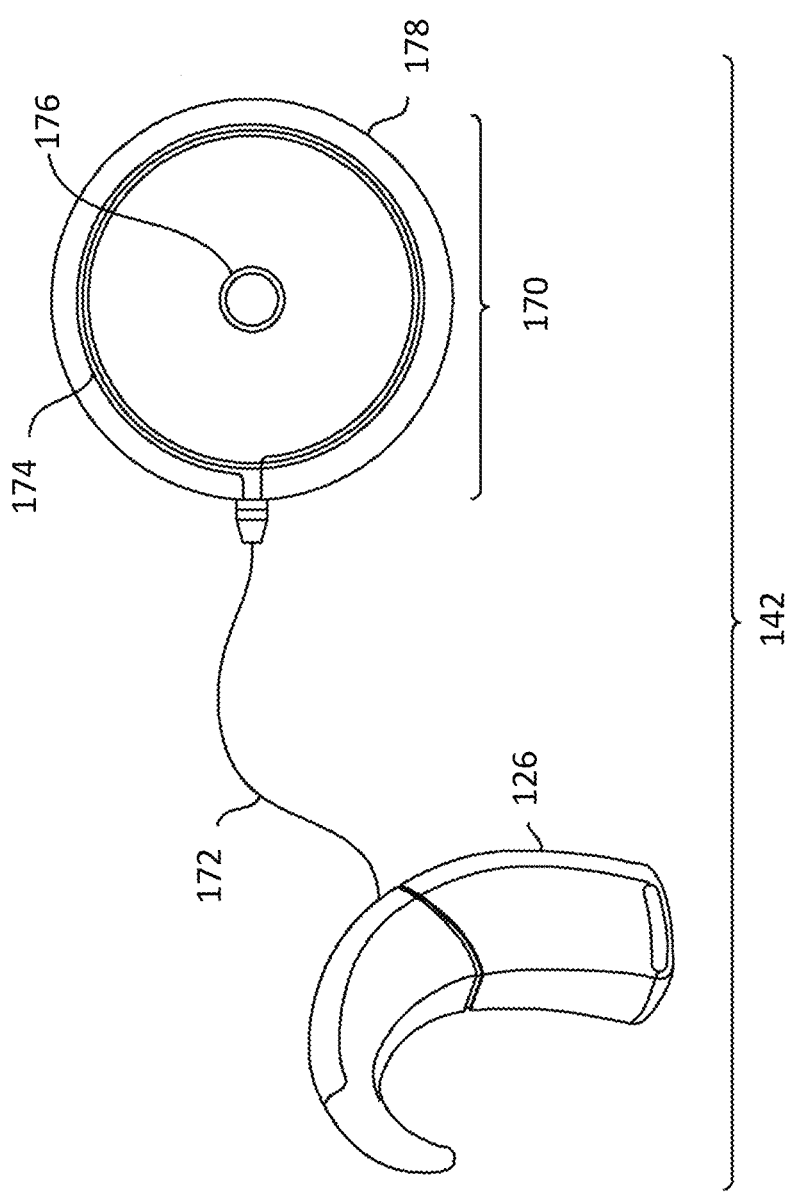
FIG. 1B is a top view of an exemplary hearing prosthesis in which at least some of the teachings detailed herein are applicable.

FIG. 1B presents some additional details of the external component 142. As can be seen, external component 142 includes a BTE device 126 which is connected via cable 172 to an exemplary inductive communication component 170 including an external inductance coil 174 (the external coil of FIG. 1A). As illustrated, an external component 142 of a cochlear implant prosthesis comprises a headpiece 178 that includes the coil 174 and a magnet 176, which magnet interacts with the implanted magnet of the implantable component (more on this below) to hold the headpiece 178 against the skin of the recipient. In an exemplary embodiment, the external component 142 is configured to transmit magnetic data and/or power transcutaneously via external inductive communication component 170 to an implantable component including an inductance coil. Inductive communication component 170 is electrically coupled to behind-the-ear (BTE) device 126 via cable 172. BTE device 126 may include, for example, at least some of the components of the external devices/components described below.

While the teachings detailed herein are often presented with regard to the external component in general, and the external inductive coil in particular, in at least some embodiments, the teachings detailed herein are also applicable to the implantable component, at least unless otherwise specified.

Figure 1C:
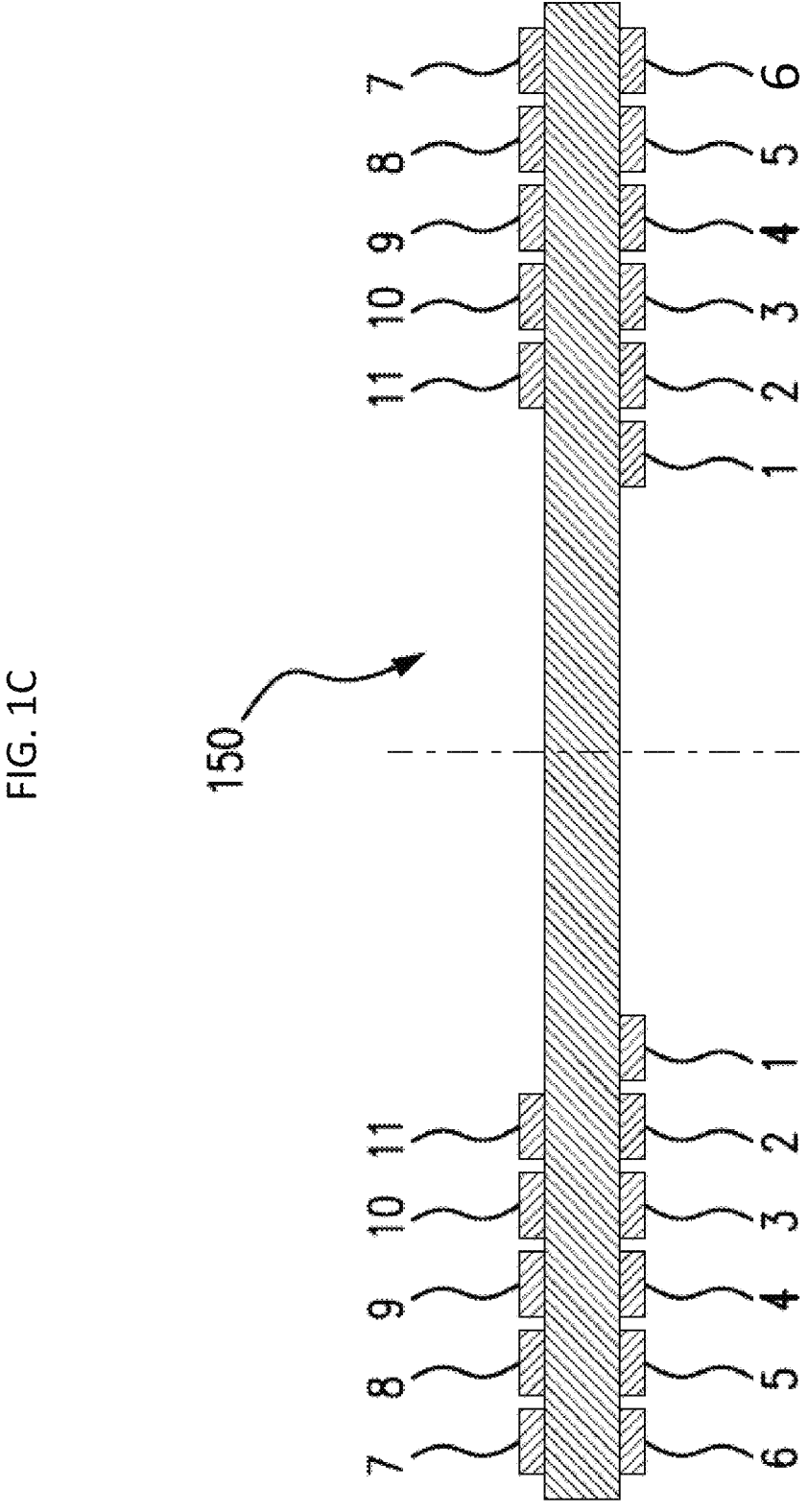
FIG. 1C is a cross-sectional view of an exemplary hearing prosthesis in which at least some of the teachings detailed herein are applicable.

FIG. 1C is a quasi-functional depiction of a portion of a cross section of the external inductive communication component 170. Specifically, FIG. 1C presents a printed circuit board (PCB) 150 including traces entailing turns 1-11 of coil 174. In this regard, PCB 150 is "embedded" or otherwise enclosed in the headpiece 178, and the PCB 150 is in communication with the BTE deice 126 via cable 172. It is noted that layers of the PCB are not shown for clarity. It is further noted that unless otherwise specified, the teachings detailed herein are also applicable to non-PCB implementations. In this regard, PCB based implementations are simply presented as but one example of a way to implement.

Figure 1D:
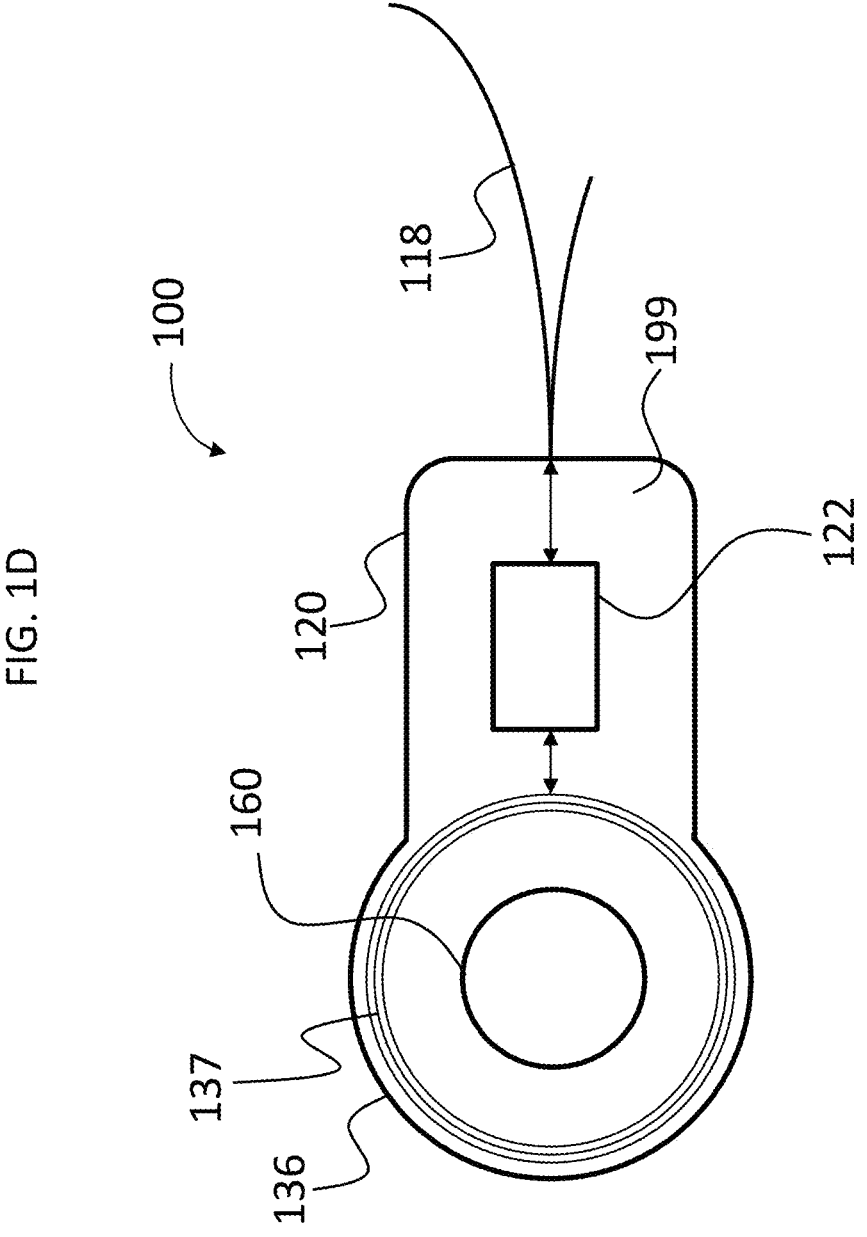
FIG. 1D is a top view of an exemplary hearing prosthesis in which at least some of the teachings detailed herein are applicable.

FIG. 1D depicts an exemplary high-level diagram of the implantable component (sometimes referred to as the cochlear implant) 100 of the system 10, looking downward from outside the skull towards the skull. As can be seen, implantable component 100 includes a magnet 160 that is surrounded by an implantable inductance coil 137 that is in two-way communication (although in other embodiments, the communication is one-way) with a stimulator unit 122, which in turn is in communication with the electrode assembly 118. The coil 137 is presented in a conceptual manner, and some specific details of the coil 137 will described below. The magnet 160 interacts with magnet 176 to retain the headpiece 178 against the skin of the recipient so that transcutaneous inductance communication can take place between the two components via inductance communication between coil 174 and coil 137. As noted above, any disclosure herein regarding the features of the external inductance coil are also applicable to the implanted inductance coil unless otherwise specified. Corollary to this is that any disclosure herein regarding the features of the implanted inductance coil are also applicable to the external inductance coil unless otherwise specified.

In an exemplary embodiment of the embodiment of FIG. 1D, there is a silicone encapsulate made of elastomeric material 199.

It is noted that magnet 160 is presented in a conceptual manner. In this regard, it is noted that in at least some embodiments, the magnet apparatus 160 is an assembly that includes a magnet surrounded by a biocompatible coating. Still further, in an exemplary embodiment, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet).

Figure 1E:
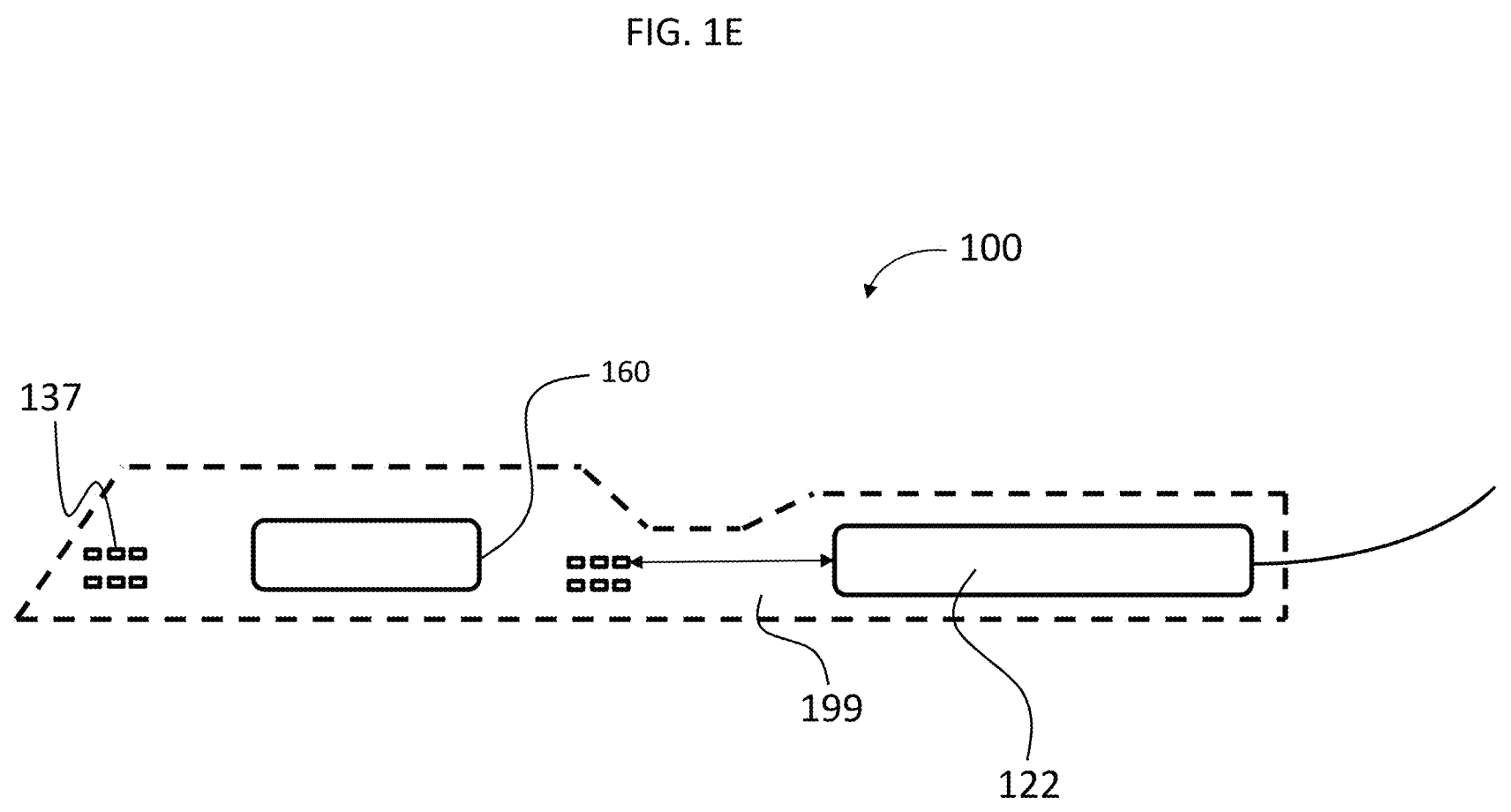

With reference now to FIG. 1E, it can be seen that the coil 137 is a multi-layered coil, with two sets of turns on two different layers, one of which is located above the other. Additional details of this will be described below. It is noted that the outlines of the housing made from elastomeric material 199 are presented in dashed line format for ease of discussion. In an exemplary embodiment, silicone or some other elastomeric material fills the interior within the dashed line, other than the other components of the implantable device magnet. That said, in an alternative embodiment, silicone or some other elastomeric material substantially fills the interior within the dashed lines other than the components of the implantable device (e.g., there can be pockets within the dashed line in which no components and no silicone is located).

It is noted that FIGS. 1B, 1C, 1D, and 1E are conceptual FIGs. presented for purposes of discussion. Commercial embodiments corresponding to these FIGs. can be different from that depicted in the figures.

It is further noted that any disclosure of features associated with the external coil/external inductance communication component corresponds to a disclosure applicable to the implantable coil/implanted inductance communication component, and visa-versa.

Additional details of the plates, magnets, and housing made of elastomeric material will be described in greater detail below. First, however, additional functional details of various embodiments of the system 10 will now be described.

FIG. 2A is a functional block diagram of a prosthesis 200A corresponding to a cochlear implant in accordance with embodiments of the present invention. Prosthesis 200A comprises an implantable component 244 configured to be implanted beneath a recipient's skin or other tissue 250 and an external device 204. For example, implantable component 244 may be implantable component 100 of FIG. 1A, and the external device may be the external device 142 of FIG. 1A. Similar to the embodiments described above with reference to FIG. 1A, implantable component 244 comprises a transceiver unit 208 which receives data and power from external device 204. External device 204 transmits power and data 220 via transceiver unit 206 to transceiver unit 208 via a magnetic induction data link 220. As used herein, the term receiver refers to any device or component configured to receive power and/or data such as the receiving portion of a transceiver or a separate component for receiving. The details of transmission of power and data to transceiver unit 208 are provided below. With regard to transceivers, it is noted at this time that while embodiments may utilize transceivers, separate receivers and/or transmitters may be utilized as appropriate. This will be apparent in view of the description below.

Implantable component 244 may comprise a power storage element 212 and a functional component 214. Power storage element 212 is configured to store power received by transceiver unit 208, and to distribute power, as needed, to the elements of implantable component 244. Power storage element 212 may comprise, for example, a rechargeable battery 212. An example of a functional component may be a stimulator unit 120 as shown in FIG. 1B.

In certain embodiments, implantable component 244 may comprise a single unit having all components of the implantable component 244 disposed in a common housing. In other embodiments, implantable component 244 comprises a combination of several separate units communicating via wire or wireless connections. For example, power storage element 212 may be a separate unit enclosed in a hermetically sealed housing. The implantable magnet apparatus and plates associated therewith may be attached to or otherwise be a part of any of these units, and more than one of these units can include the magnet apparatus and plates according to the teachings detailed herein and/or variations thereof.

In the embodiment depicted in FIG. 2A, external device 204 includes a data processor 210 that receives data from data input unit 211 and processes the received data. The processed data from data processor 210 is transmitted by transceiver unit 206 to transceiver unit 208. In an exemplary embodiment, data processor 210 may be a sound processor, such as the sound processor of FIG. 1A for the cochlear implant thereof, and data input unit 211 may be a microphone of the external device.

Figure 2B:
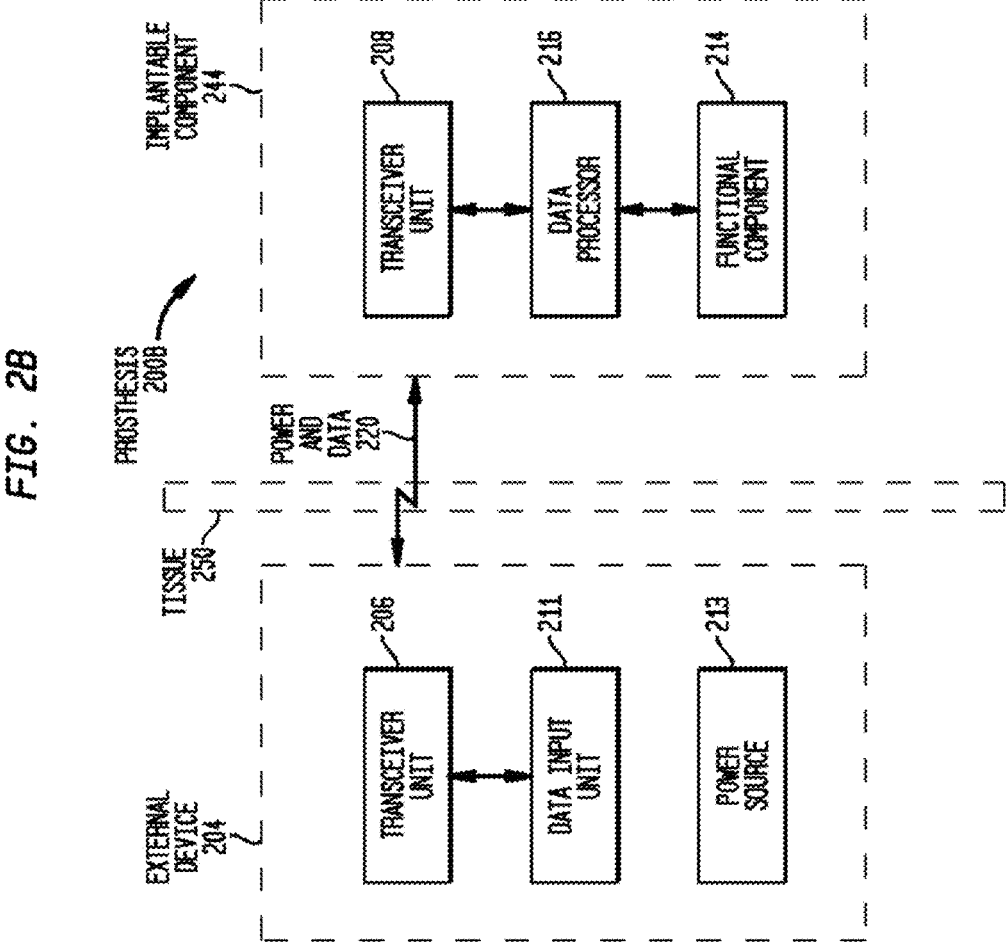
FIG. 2B is an alternate functional block diagram of a prosthesis, in accordance with some embodiments.

FIG. 2B presents an alternate embodiment of the prosthesis 200A of FIG. 2A, identified in FIG. 2B as prosthesis 200B. As may be seen from comparing FIG. 2A to FIG. 2B, the data processor can be located in the external device 204 or can be located in the implantable component 244. In some embodiments, both the external device 204 and the implantable component 244 can include a data processor.

As shown in FIGS. 2A and 2B, external device 204 can include a power source 213. Power from power source 213 can be transmitted by transceiver unit 206 to transceiver unit 208 to provide power to the implantable component 244, as will be described in more detail below.

While not shown in FIGS. 2A and 2B, external device 204 and/or implantable component 244 include respective inductive communication components. These inductive communication components can be connected to transceiver unit 206 and transceiver unit 208, permitting power and data 220 to be transferred between the two units via magnetic induction.

As used herein, an inductive communication component includes both standard induction coils and inductive communication components configured to vary their effective coil areas.

Figure 3A:
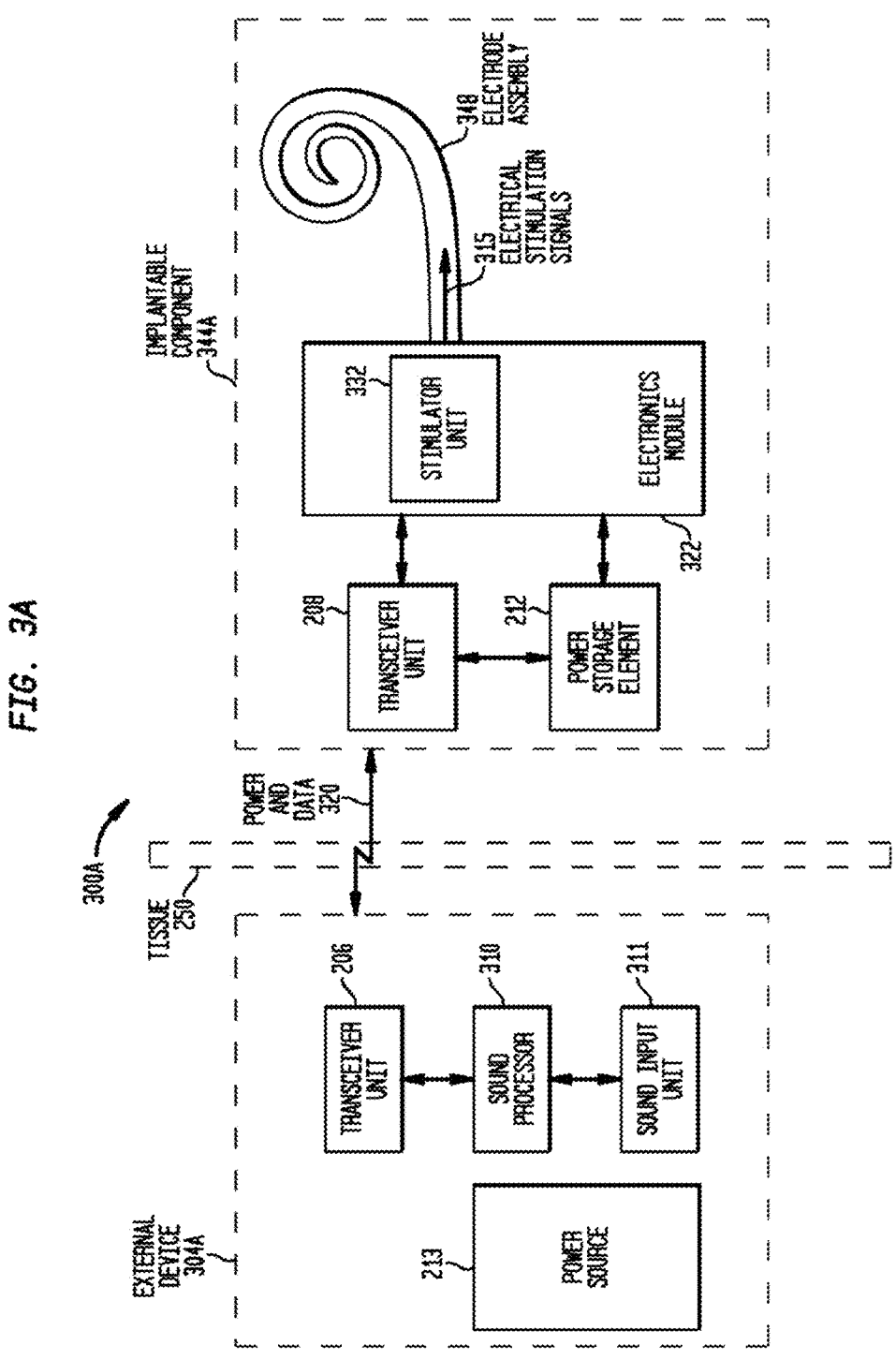
FIG. 3A is a functional block diagram of a cochlear implant, in accordance with some embodiments.

As noted above, prosthesis 200A of FIG. 2A may be a cochlear implant. In this regard, FIG. 3A provides additional details of an embodiment of FIG. 2A where prosthesis 200A is a cochlear implant. Specifically, FIG. 3A is a functional block diagram of a system 300A in accordance with embodiments.

It is noted that the components detailed in FIGS. 2A and 2B may be identical to the components detailed in FIG. 3A, and the components of 3A may be used in the embodiments depicted in FIGS. 2A and 2B.

System 300A comprises an implantable component 344A (e.g., implantable component 100 of FIG. 1) configured to be implanted beneath a recipient's skin or other tissue 250, and an external device 304A. External device 304A may be an external component such as external component 142 of FIG. 1.

Similar to the embodiments described above with reference to FIGS. 2A and 2B, implantable component 344A comprises a transceiver unit 208 (which may be the same transceiver unit used in FIGS. 2A and 2B) which receives data and power from external device 304A. External device 304A transmits data and/or power 320 to transceiver unit 208 via a magnetic induction data link. This can be done while charging module 202.

Implantable component 344A also comprises a power storage element 212, electronics module 322 (which may include components such as sound processor 126 and/or may include a stimulator unit 322 corresponding to stimulator unit 122 of FIG. 1B) and an electrode assembly 348 (which may include an array of electrode contacts 148 of FIG. 1A). Power storage element 212 is configured to store power received by transceiver unit 208, and to distribute power, as needed, to the elements of implantable component 344A.

As shown, electronics module 322 includes a stimulator unit 332. Electronics module 322 can also include one or more other functional components used to generate or control delivery of electrical stimulation signals 315 to the recipient. As described above with respect to FIG. 1A, electrode assembly 348 is inserted into the recipient's cochlea and is configured to deliver electrical stimulation signals 315 generated by stimulator unit 332 to the cochlea.

In the embodiment depicted in FIG. 3A, the external device 304A includes a sound processor 310 configured to convert sound signals received from sound input unit 311 (e.g., a microphone, an electrical input for an FM hearing system, etc.) into data signals. In an exemplary embodiment, the sound processor 310 corresponds to data processor 210 of FIG. 2A.

Figure 3B:
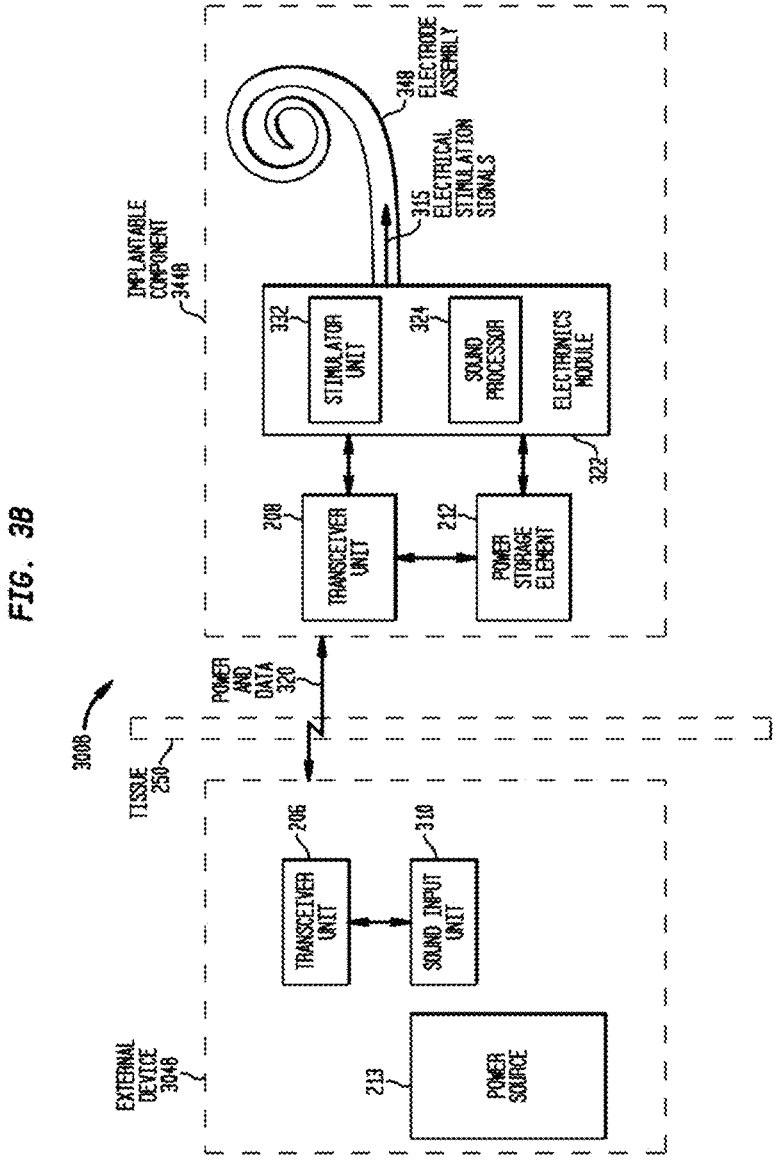
FIG. 3B is an alternate functional block diagram of a cochlear implant, in accordance with some embodiments.

FIG. 3B presents an alternate embodiment of a system 300B. The elements of system 300B correspond to the elements of system 300A except that external device 304B does not include sound processor 310. Instead, the implantable component 344B includes a sound processor 324, which may correspond to sound processor 310 of FIG. 3A.

As will be described in more detail below, while not shown in the figures, external device 304A/304B and/or implantable component 344A/344B include respective inductive communication components.

FIGS. 3A and 3B illustrate that external device 304A/304B can include a power source 213, which may be the same as power source 213 depicted in FIG. 2A. Power from power source 213 can be transmitted by transceiver unit 306 to transceiver unit 308 to provide power to the implantable component 344A/344B, as will be detailed below. FIGS. 3A and 3B further detail that the implantable component 344A/344B can include a power storage element 212 that stores power received by the implantable component 344 from power source 213. Power storage element 212 may be the same as power storage element 212 of FIG. 2A.

Figure 3C:
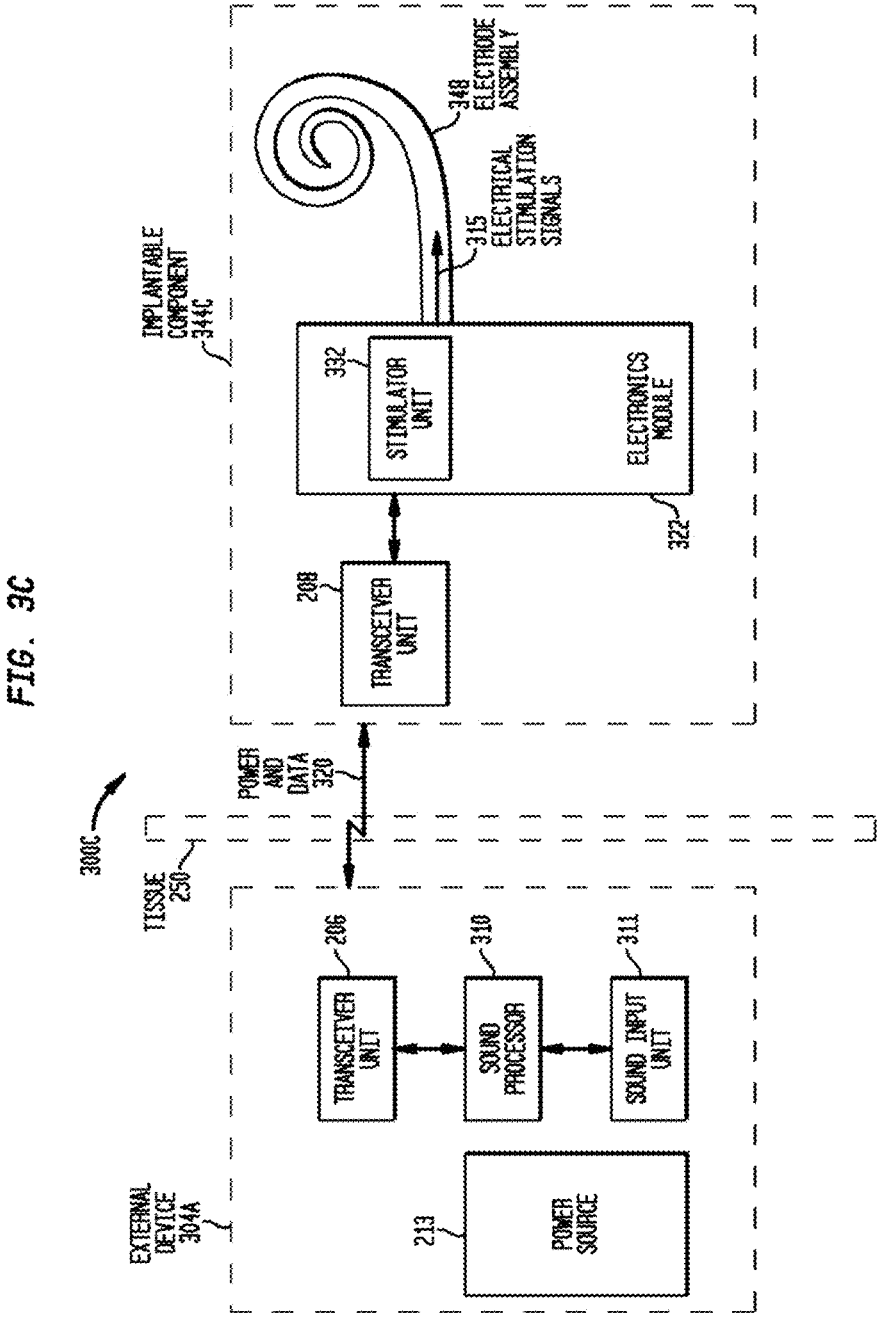
FIG. 3C is yet another alternate functional block diagram of a cochlear implant, in accordance with some embodiments.

In contrast to the embodiments of FIGS. 3A and 3B, as depicted in FIG. 3C, an embodiment of a system 300C includes an implantable component 344C that does not include a power storage element 212. In the embodiment of FIG. 3C, sufficient power is supplied by external device 304A/304B in real time to power implantable component 344C without storing power in a power storage element. In FIG. 3C, all of the elements are the same as FIG. 3A except for the absence of power storage element 212.

Some of the components of FIGS. 3A-3C will now be described in greater detail.

Figure 4A:
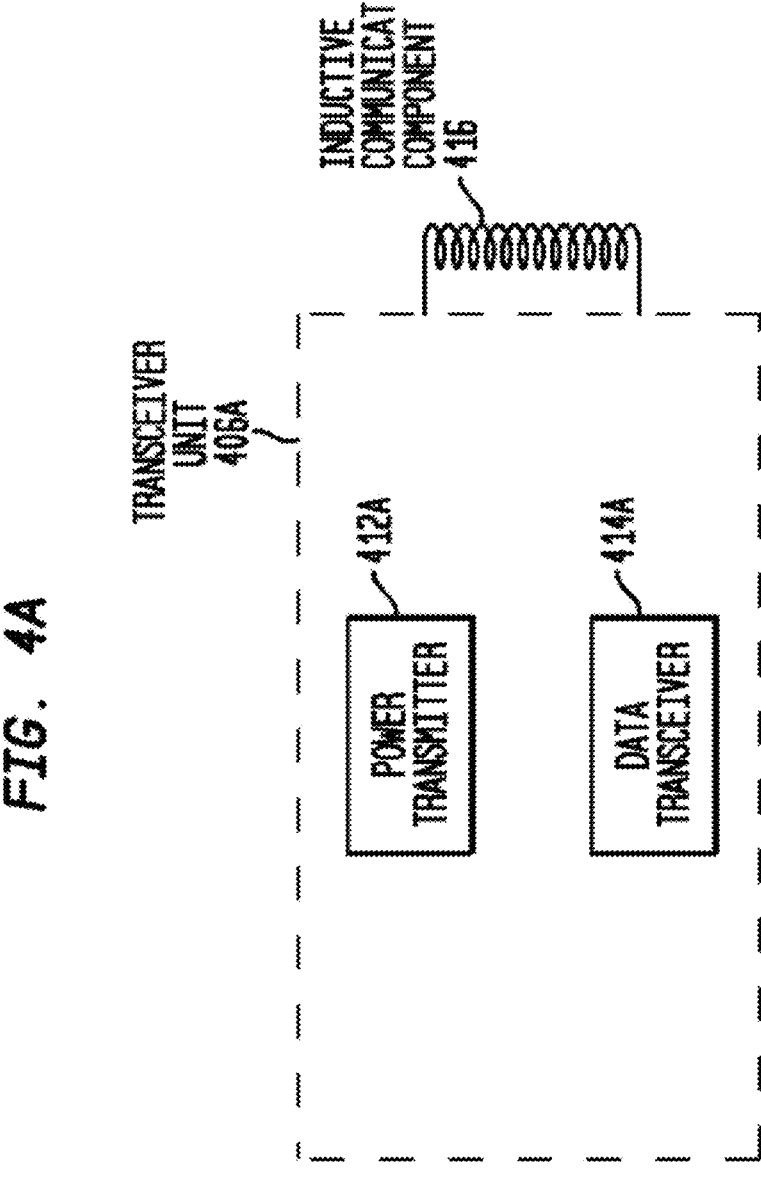
FIG. 4A is a simplified schematic diagram of a transceiver unit of an external device in accordance with some embodiments.

FIG. 4A is a simplified schematic diagram of a transceiver unit 406A in accordance with an embodiment. An exemplary transceiver unit 406A may correspond to transceiver unit 206 of FIGS. 2A-3C. As shown, transceiver unit 406A includes a power transmitter 412 *a*, a data transceiver 414A and an inductive communication component 416.

In an exemplary embodiment, as will be described in more detail below, inductive communication component 416 comprises one or more wire antenna coils (depending on the embodiment) comprised of multiple turns of electrically insulated single-strand or multi-strand platinum or gold wire (thus corresponding to coil 137 of FIG. 1B). Power transmitter 412A comprises circuit components that inductively transmit power from a power source, such as power source 213, via an inductive communication component 416 to implantable component 344A/B/C (FIGS. 3A-3C). Data transceiver 414A comprises circuit components that cooperate to output data for transmission to implantable component 344A/B/C (FIGS. 3A-3C). Transceiver unit 406A can receive inductively transmitted data from one or more other components of system 300A/B/C, such as telemetry or the like from implantable component 344A (FIG. 3A).

Transceiver unit 406A can be included in a device that includes any number of components which transmit data to implantable component 334A/B/C. For example, the transceiver unit 406A may be included in a behind-the-ear (BTE) device having one or more of a microphone or sound processor therein, an in-the-ear device, etc.

Figure 4B:
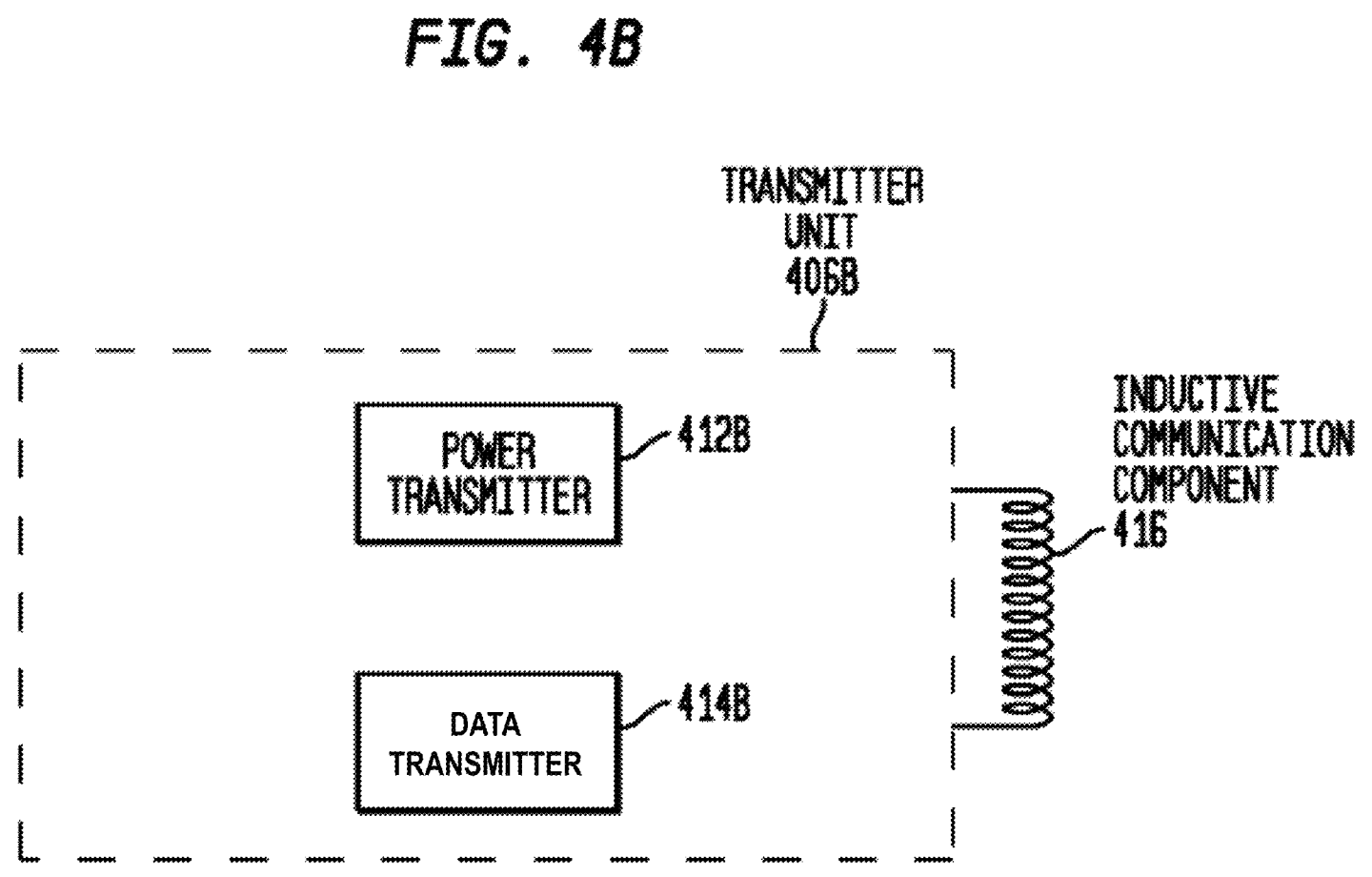

FIG. 4B depicts a transmitter unit 406B, which is identical to transceiver unit 406A, except that it includes a power transmitter 412B and a data transmitter 414B.

It is noted that for ease of description, power transmitter 412A and data transceiver 414A/data transmitter 414B are shown separate. However, it should be appreciated that in certain embodiments, at least some of the components of the two devices may be combined into a single device.

Figure 4C:
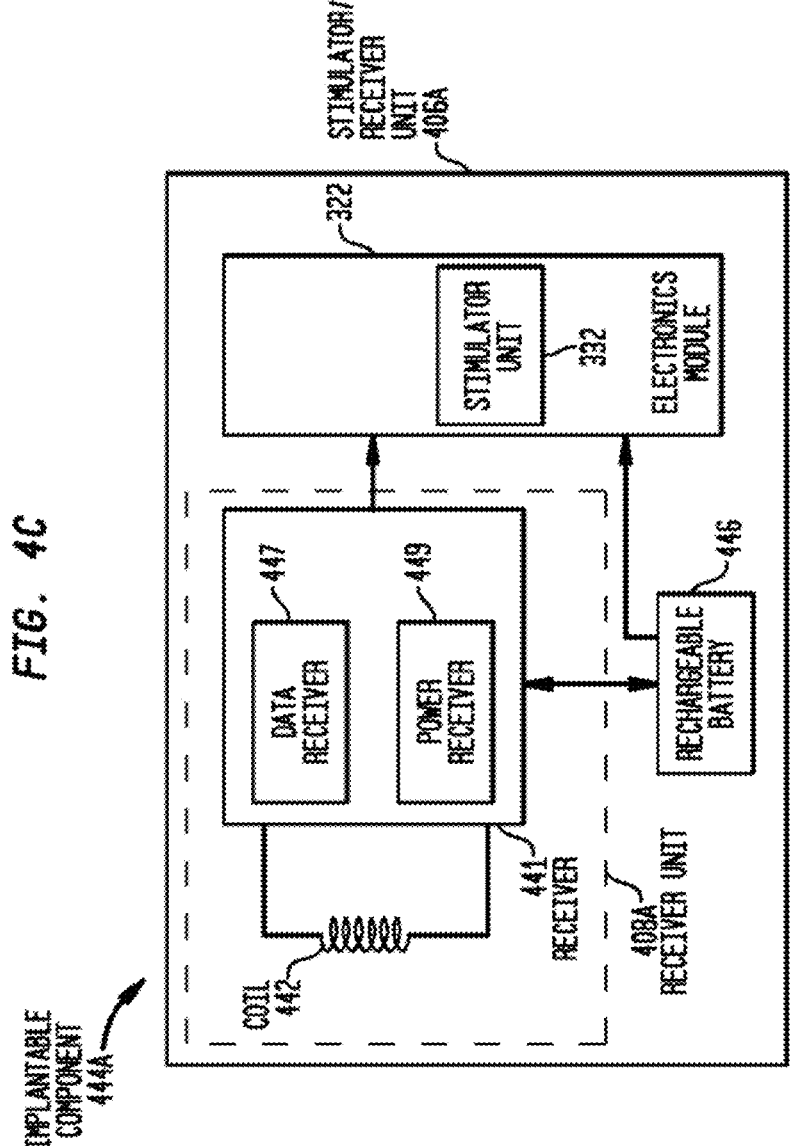
FIG. 4C is a simplified schematic diagram of a stimulator/receiver unit including a data receiver of an implantable device in accordance with in accordance with some embodiments.

FIG. 4C is a simplified schematic diagram of one embodiment of an implantable component 444A that corresponds to implantable component 344A of FIG. 3A, except that transceiver unit 208 is a receiver unit. In this regard, implantable component 444A comprises a receiver unit 408A, a power storage element, shown as rechargeable battery 446, and electronics module 322, corresponding to electronics module 322 of FIG. 3A. Receiver unit 408A includes an inductance coil 442 connected to receiver 441. Receiver 441 comprises circuit components which receive via an inductive communication component corresponding to an inductance coil 442 inductively transmitted data and power from other components of system 300A/B/C, such as from external device 304A/B. The components for receiving data and power are shown in FIG. 4C as data receiver 447 and power receiver 449. For ease of description, data receiver 447 and power receiver 449 are shown separate. However, it should be appreciated that in certain embodiments, at least some of the components of these receivers may be combined into one component.

In the illustrative embodiments, receiver unit 408A and transceiver unit 406A (or transmitter unit 406B) establish a transcutaneous communication link over which data and power is transferred from transceiver unit 406A (or transmitter unit 406B), to implantable component 444A. As shown, the transcutaneous communication link comprises a magnetic induction link formed by an inductance communication component system that includes inductive communication component 416 and coil 442.

The transcutaneous communication link established by receiver unit 408A and transceiver unit 406A (or whatever other viable component can so establish such a link), in an exemplary embodiment, may use time interleaving of power and data on a single radio frequency (RF) channel or band to transmit the power and data to implantable component 444A. A method of time interleaving power according to an exemplary embodiment uses successive time frames, each having a time length and each divided into two or more time slots. Within each frame, one or more time slots are allocated to power, while one or more time slots are allocated to data. In an exemplary embodiment, the data modulates the RF carrier or signal containing power. In an exemplary embodiment, transceiver unit 406A and transmitter unit 406B are configured to transmit data and power, respectively, to an implantable component, such as implantable component 344A, within their allocated time slots within each frame.

The power received by receiver unit 408A can be provided to rechargeable battery 446 for storage. The power received by receiver unit 408A can also be provided for distribution, as desired, to elements of implantable component 444A. As shown, electronics module 322 includes stimulator unit 332, which in an exemplary embodiment corresponds to stimulator unit 322 of FIGS. 3A-3C, and can also include one or more other functional components used to generate or control delivery of electrical stimulation signals to the recipient.

In an embodiment, implantable component 444A comprises a receiver unit 408A, rechargeable battery 446 and electronics module 322 integrated in a single implantable housing, referred to as stimulator/receiver unit 406A. It would be appreciated that in alternative embodiments, implantable component 344 may comprise a combination of several separate units communicating via wire or wireless connections.

Figure 4D:
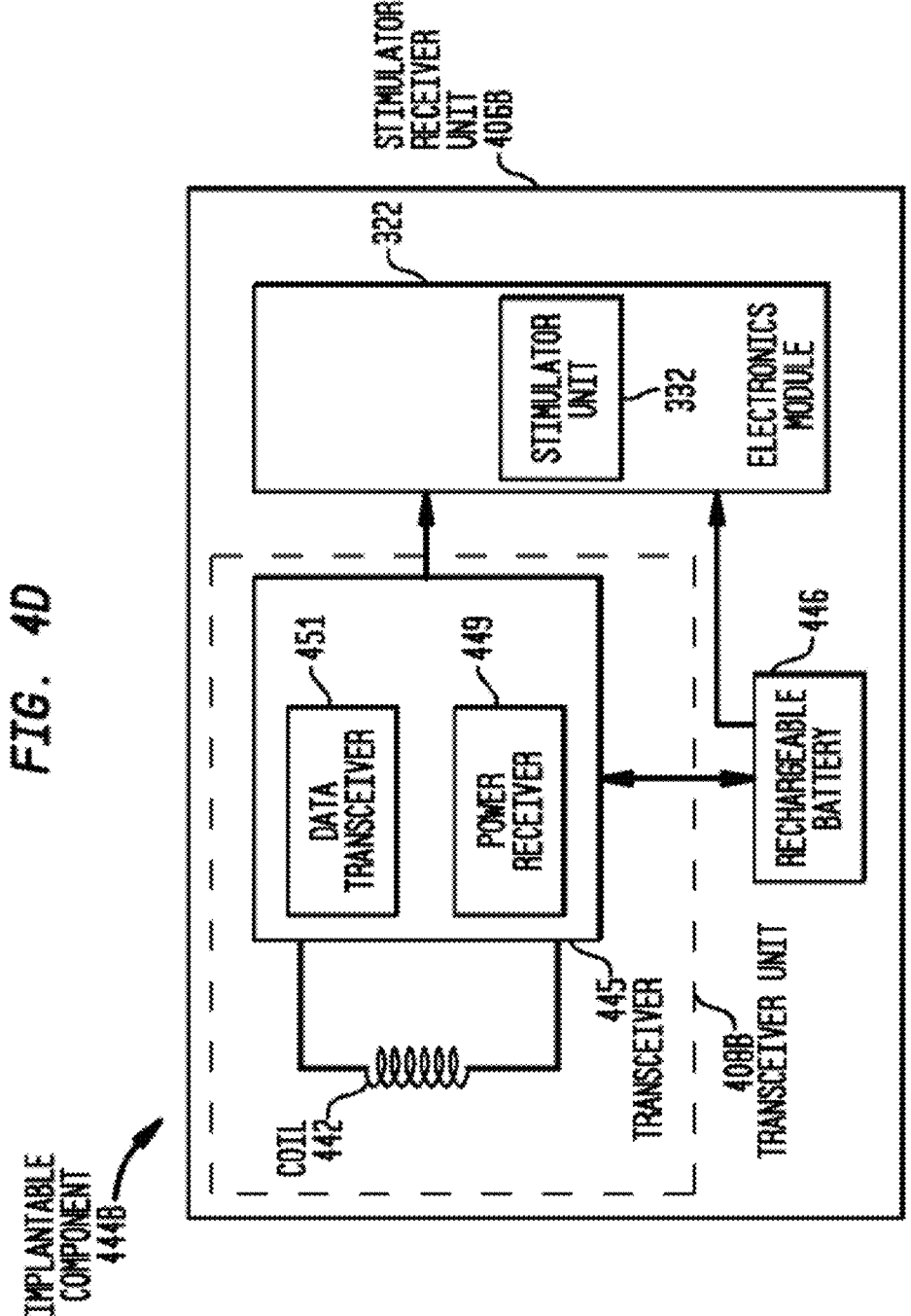
FIG. 4D is a simplified schematic diagram of a stimulator/receiver unit including a data transceiver of an implantable device in accordance with some embodiments.

FIG. 4D is a simplified schematic diagram of an alternate embodiment of an implantable component 444B. Implantable component 444B is identical to implantable component 444A of FIG. 4C, except that instead of receiver unit 408A, it includes transceiver unit 408B. Transceiver unit 408B includes transceiver 445 (as opposed to receiver 441 in FIG. 4C). Transceiver unit 445 includes data transceiver 451 (as opposed to data receiver 447 in FIG. 4C).

Figure 4E:
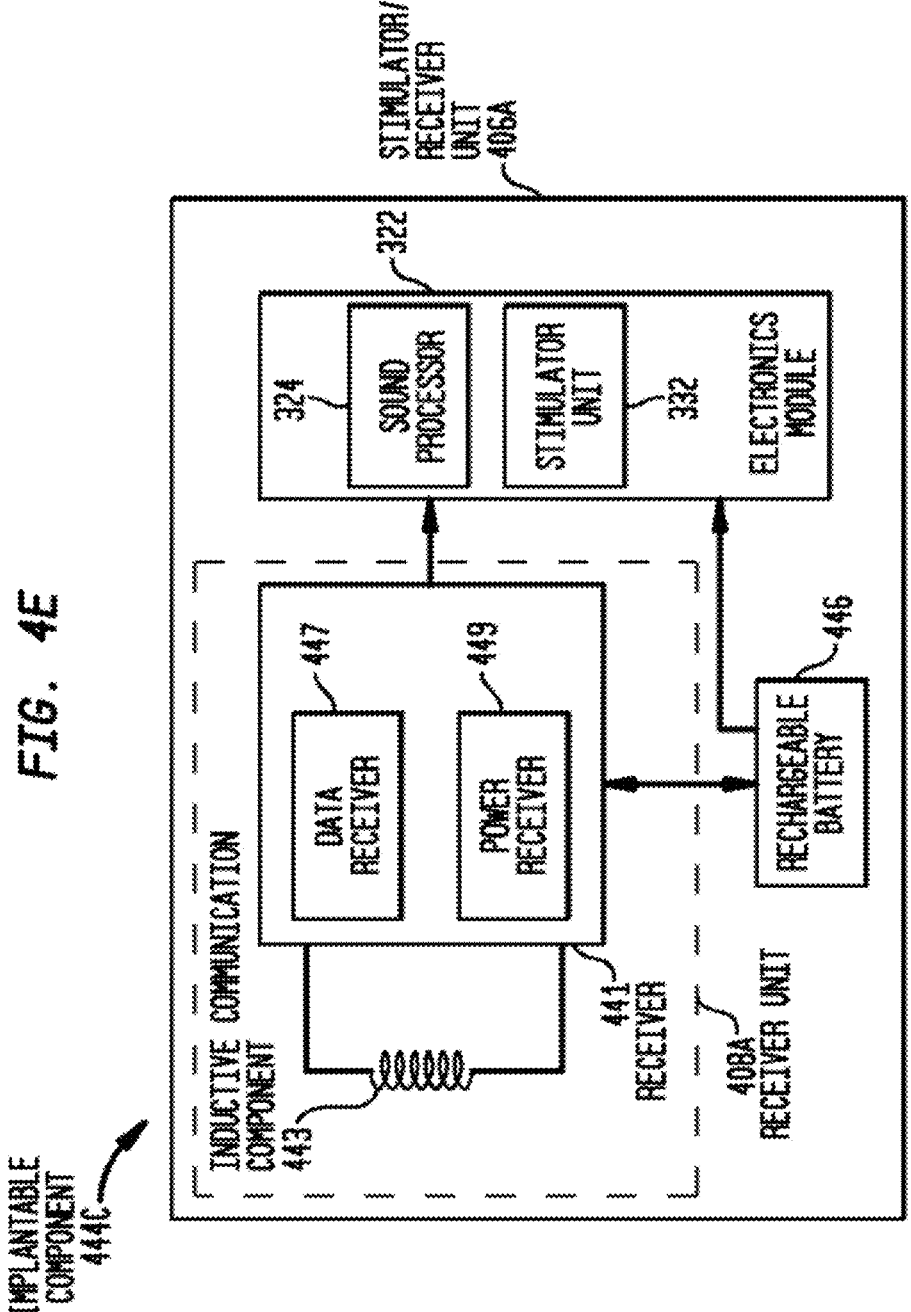
FIG. 4E is a simplified schematic diagram of a stimulator/receiver unit including a data receiver and a communication component configured to vary the effective coil area of an implantable device in accordance with some embodiments.
Figure 4F:
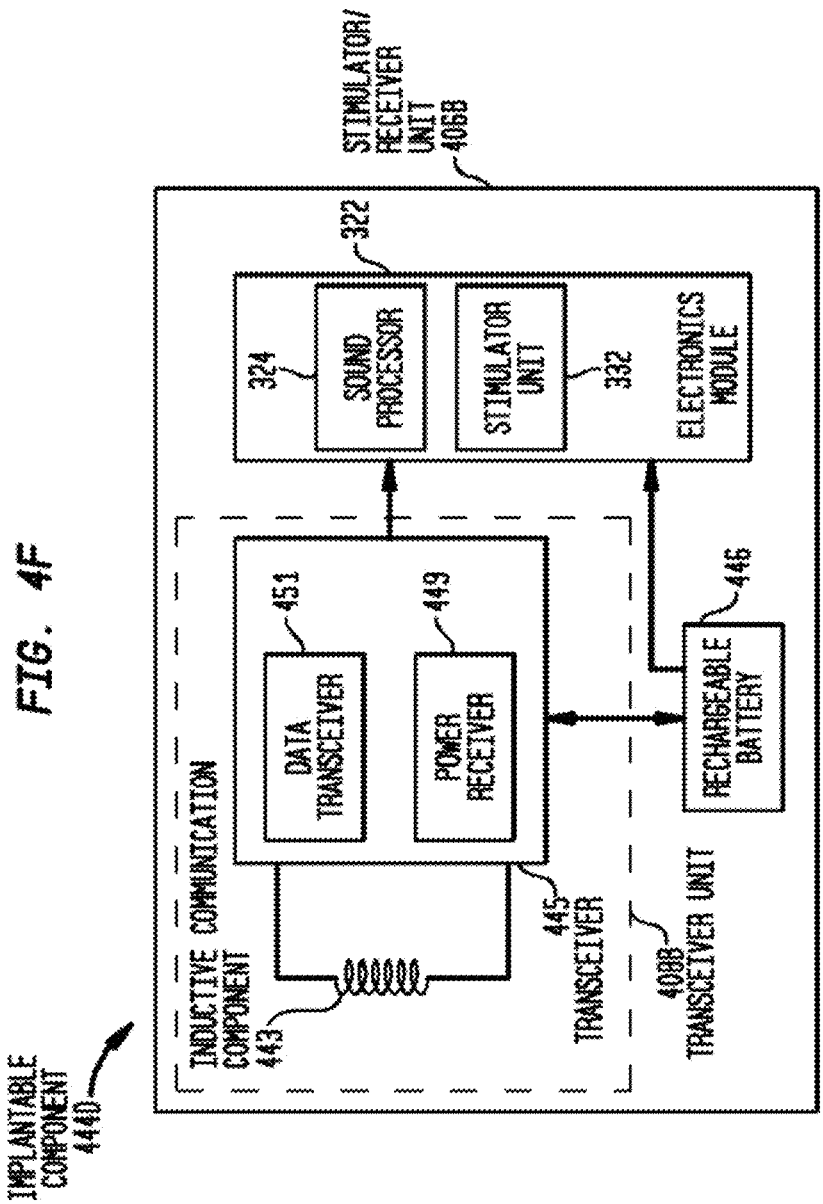
FIG. 4F is a simplified schematic diagram of a stimulator/receiver unit including a data transceiver and a communication component configured to vary the effective coil area of an implantable device in accordance with some embodiments.

FIGS. 4E and 4F depict alternate embodiments of the implantable components 444A and 444B depicted in FIGS. 4C and 4D, respectively. In FIGS. 4E and 4F, instead of coil 442, implantable components 444C and 444D (FIGS. 4E and 4F, respectively) include inductive communication component 443. Inductive communication component 443 is configured to vary the effective coil area of the component, and may be used in cochlear implants where the exterior device 304A/B does not include a communication component configured to vary the effective coil area (i.e., the exterior device utilizes a standard inductance coil). In other respects, the implantable components 444C and 444D are substantially the same as implantable components 444A and 444B. Note that in the embodiments depicted in FIGS. 4E and 4F, the implantable components 444C and 444D are depicted as including a sound processor 342. In other embodiments, the implantable components 444C and 444D may not include a sound processor 342.

Figure 5A:
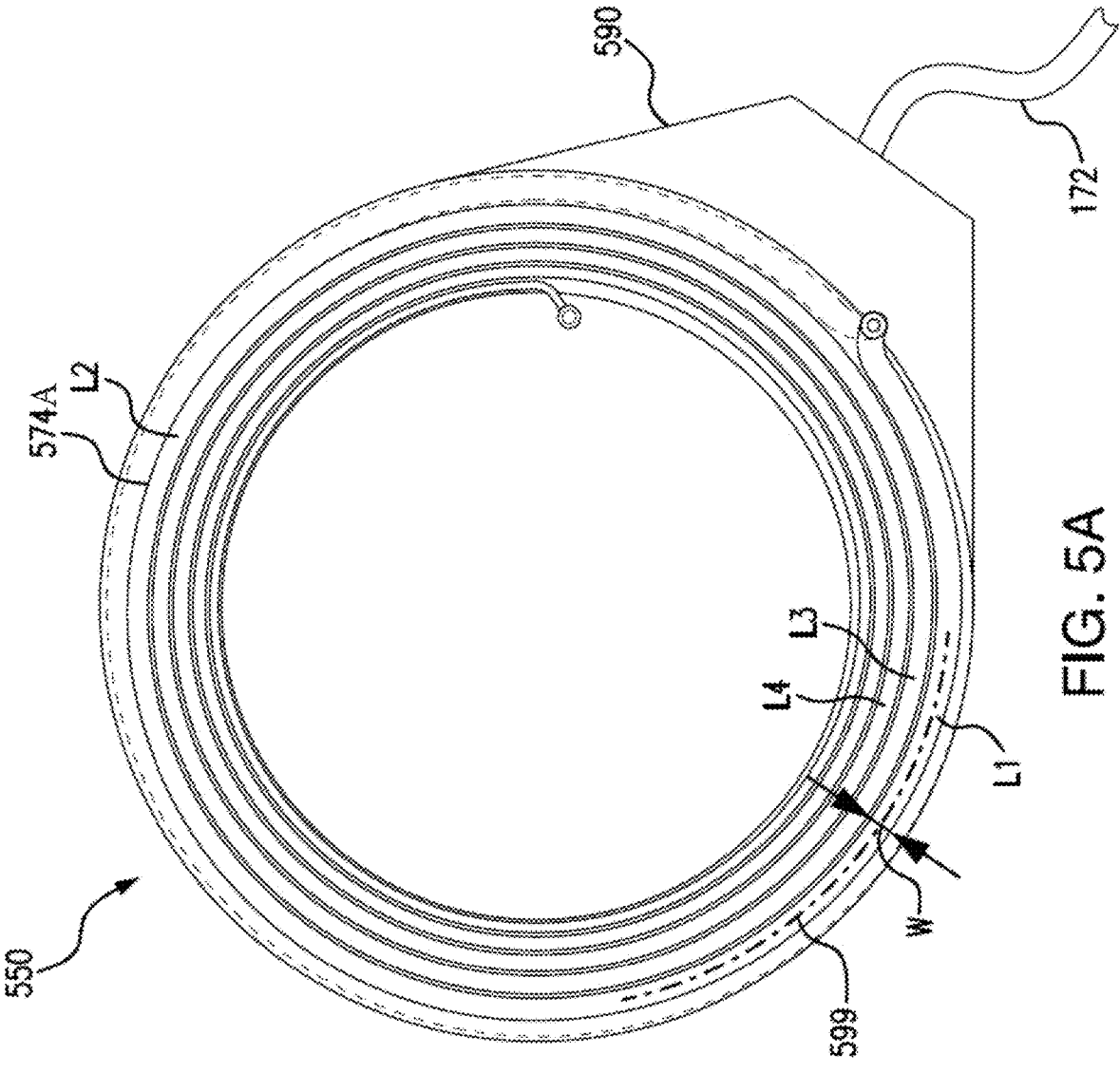
FIG. 5A is an exemplary conceptual schematic of a top view of an exemplary printed circuit board of an exemplary embodiment.

FIG. 5A depicts a top view of an exemplary embodiment of printed circuit board (PCB) 550A corresponding to a printed circuit board of an external inductance communication component corresponding with respect to functionality thereof to external inductance communication component 170 of FIG. 1B presented above. It is briefly noted that while the embodiments detailed herein are presented in terms of a PCB, alternative embodiments can be implemented in a non-PCB based device. Any arrangement that can enable the teachings detailed herein and/or variations thereof to be practiced can be utilized in at least some embodiments. As can be seen, the embodiment of FIG. 5A includes a coil 574A comprising a conductor that includes a plurality of turns, where the conductor has a non-uniform width. In the exemplary embodiment of FIG. 5A, the conductor has a width W that at least generally decreases with location (continuously or in discrete decrements) along the conductor from the portion of the conductor proximate to the connection/interface 590 with the cable 172, where the width W is measured normal to a local longitudinal axis 599 of the conductor of the coil 574A. In an exemplary embodiment, the width W is shortest distance from a first side of a turn to a second side of a turn across the top surface normal to respective tangent lines of the inner radius and the outer radius (the top surface facing the viewer with respect to FIG. 5A) at any given location along the conductor (as differentiated from, for example, the thickness of the conductor, which is measured in a direction normal to the plane of FIG. 5A).

Herein, the aforementioned width W will be sometimes referred to as the winding track width. In the exemplary embodiment of FIG. 5A, the winding track width is narrower in the inner turns relative to the outer turns. That said, as will be described below, in an alternative embodiment, the winding track width is widest in the middle turns.

More generally, it is noted that the embodiment of FIG. 5A includes five (5) conductor turns on the top layer (as seen in FIG. 5A), and includes six turns on the bottom layer (not visible in FIG. 5A, but discussed below). As used herein, a turn entails a portion of the conductor that subtends an angle of about 360°. A beginning of a turn can be considered to begin anywhere, although in the exemplary embodiments detailed herein, the turns will be described as beginning at the location closest to the connection interface 590. Thus, each turn begins at about the 6 o'clock position. In other embodiments, the turns can be considered to begin elsewhere.

Still further, in an exemplary embodiment, the coil 524 is implemented on a PCB. That is, in an exemplary embodiment, the coils are PCB based coils. Accordingly, in an exemplary embodiment, the coils can correspond to PCB traces/conductive traces.

Figure 5B:
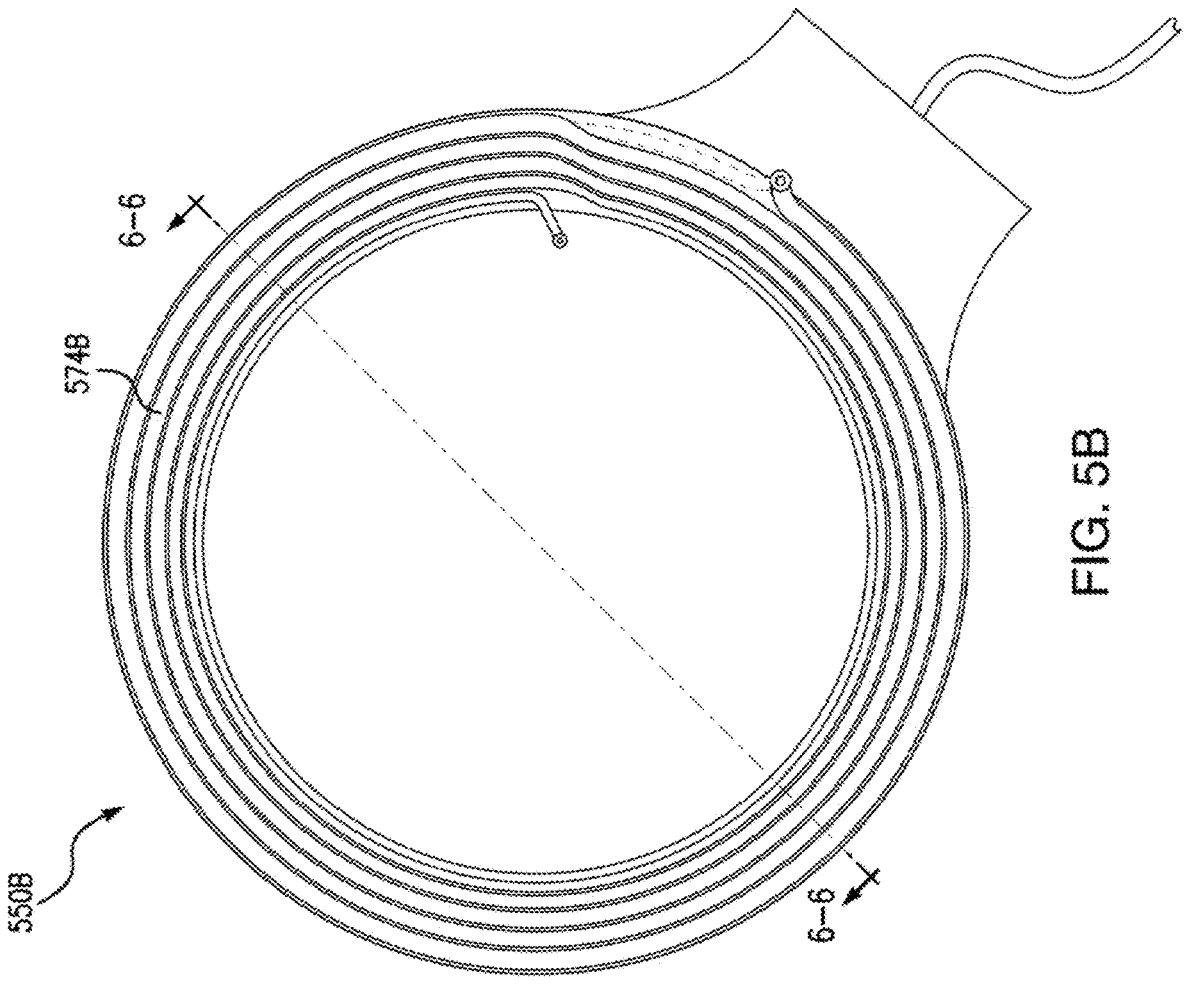
FIG. 5B is an exemplary conceptual schematic of a top view of another exemplary printed circuit board of an exemplary embodiment.

It is noted that the aforementioned decrease in width W can start immediately with respect to a given turn (e.g., at the 6 o'clock position), or can start somewhere downrange of a given turn. Additional exemplary variations of the width of the conductor will be described below. However, for the purposes of the present discussion, the coil 574A is a coil that continuously decreases in width with distance from the 6 o'clock position closest to the connection interface 590. Conversely, in other embodiments, as can be seen in FIG. 5B, the width of the conductor decreasing in a digital manner. FIG. 5B depicts an exemplary embodiment of printed circuit board (PCB) 550B corresponding to a printed circuit board of an external inductance communication component corresponding with respect to functionality thereof to external inductance communication component 170 of FIG. 1B presented above. As can be seen, the embodiment of FIG. 5B includes a coil 574B comprising a conductor that includes a plurality of turns, where the conductor has a non-uniform width with respect to a given turn.

In view of FIG. 5A, in an exemplary embodiment, there is an inductance communication coil, such as coil 574A, comprising, a conductor having at least one conductive turn, wherein a width of the conductor is wider at a first location (e.g., location L1 in FIG. 5A) relative to that at a second location (e.g., location L2 in FIG. 5A, location L3, location L4 in FIG. 5A, etc.).

Figure 6:
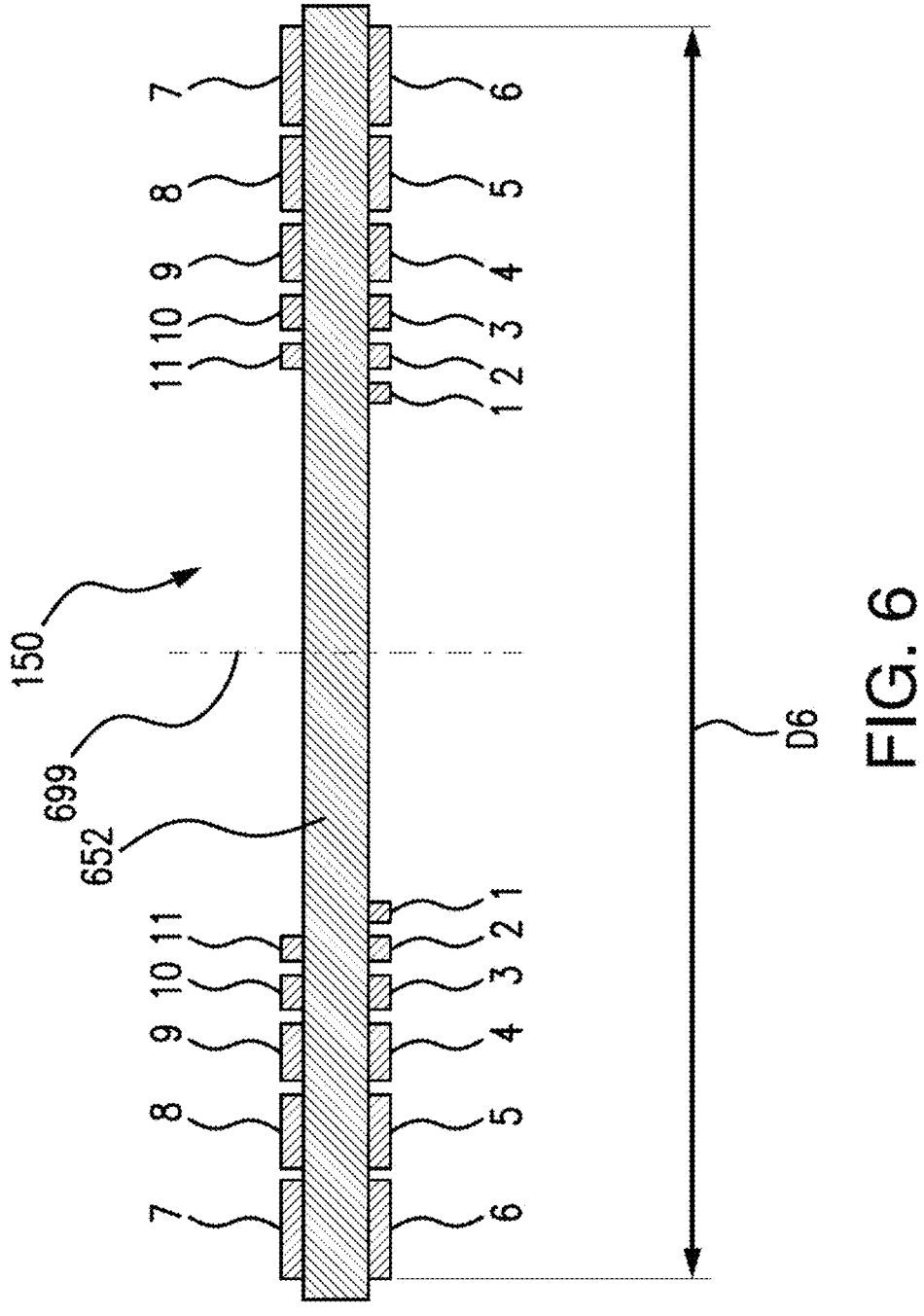
FIG. 6 is an exemplary cross-sectional view of the exemplary circuit board of FIG. 5B.

FIG. 6 depicts a cross-sectional view of the PCB 550B of FIG. 5B taken along the line 6-6, which extends between the 9 o'clock position to the 3 o'clock position (relative to the connection interface 590, with that being the 6 o'clock position). More specifically, FIG. 6 depicts substrate 652 having located thereon the conductor 574 including turns 1-11. Turns 1-6 are located on one side of the substrate (the far side of the depiction of FIG. 5A), and turns 7-11 are located on the other side of the substrate. As seen, respective turns on respective layers are aligned with one another and have the same widths (e.g., turn 6 as the same width as turn 7, turn 4 has the same width as turn 9, etc.), although in alternate embodiments, this is not the case. Further, it is noted that while the bottom turns include one more turn than the number of turns on the top, in an alternate embodiment, the number of turns are equal between the top and bottom or, in an alternate embodiment, the top includes more turns than the bottom.

It is noted that while the embodiments detailed herein are presented in terms of having six turns on one side and five turns on the other, in some alternate embodiments, more or fewer turns can be utilized. Any number of turns that can have utilitarian value with respect to the teachings detailed herein can be utilized in at least some exemplary embodiments. Indeed, in an exemplary embodiment, a single turn can be utilized (which includes a single turn on each side of the substrate 652). Note further that while the embodiments detailed herein depict turns/conductor componentry on both sides of the substrate 652, in some alternate embodiments, conductor componentry is located only on one side of the substrate. That said, in some alternate embodiments, a third and/or a fourth and/or a fifth and/or a sixth or more layers of conductor componentry are utilized in some exemplary embodiments of an inductive communication component utilizing at least some of the teachings detailed herein. Note further that there can be, in some embodiments, layers of substrate outside the layers of windings (e.g., with respect to FIG. 1C, above turns 7, 8, 9, 10, 11, and below turns 6, 5, 4, 3, 2, 1). That is, in some embodiments, the windings may not be on the outer layers.

Axis 699 constitutes the axis of rotation of the turns and/or the longitudinal axis of the PCB 550A/center of the PCB 550A.

It is noted that the widths of the cross-sections of the turns on the left side of axis 699/the distance between the outside of a given turn and the inside of a given turn as measured across the top surface the conductor is greater than those on the right side of axis 699, owing to the fact that the width decreases in a constant manner with movement along the conductor, as noted above. That said, as noted above, in an alternate embodiment, the widths can be the same on both sides of the axis 699, where the widths decrease in a digital manner again as will be described in greater detail below.

Figure 7:
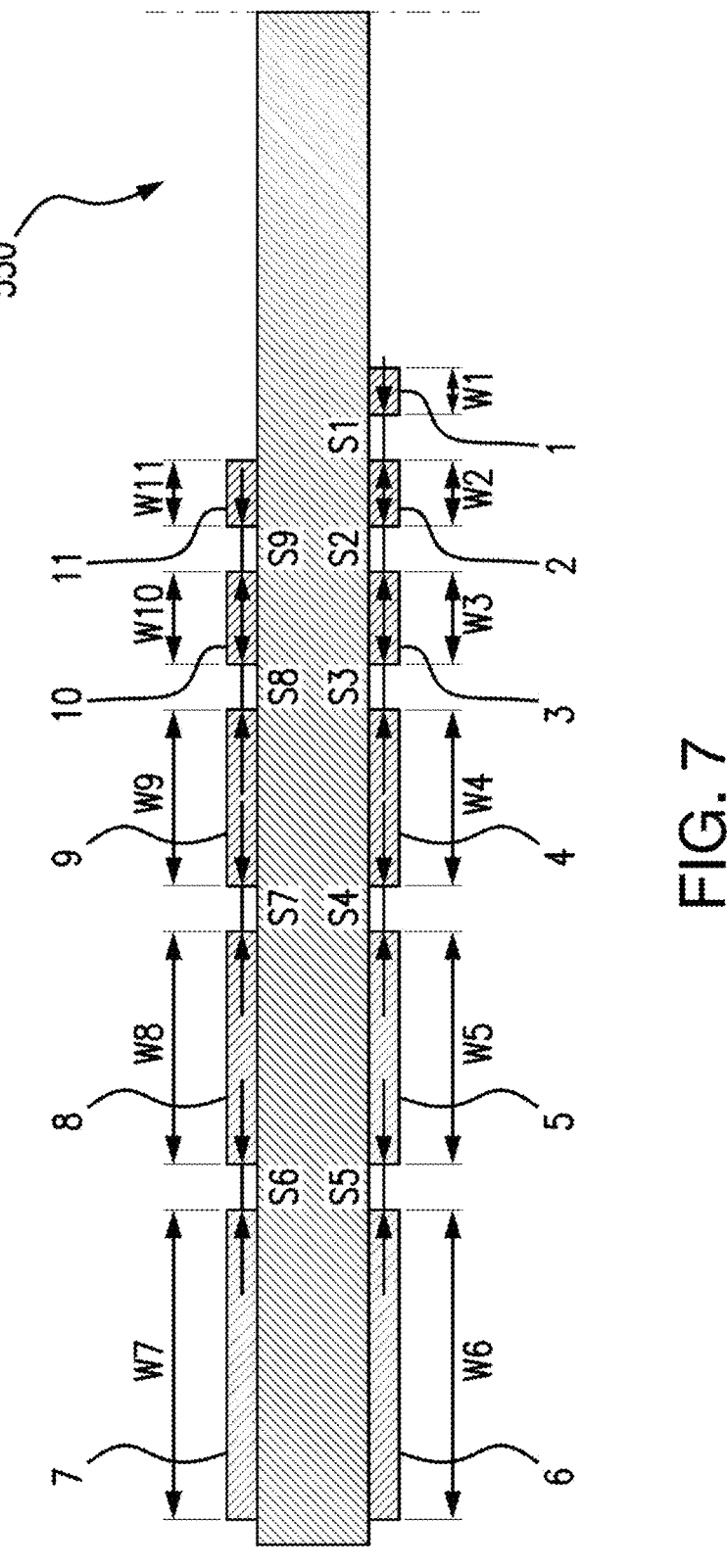
FIG. 7 depicts a detailed view of the exemplary cross-sectional view of FIG. 6.

FIG. 7 depicts a close-up view of the left portion of the PCB 550A. As can be seen, each trace includes a respective width "W" (W1, W2, W3, W4, W5, W6, W7, W8, W9, W10, and W11), where W6 is greater than W5 which is greater than W4 which is greater than W3 which is greater than W2 which is greater than W1, and W7 is greater than W8 which is greater than W9 which is greater than W10 which is greater than W11. Further, W6 is equal to W7, W8 is equal to W5, W4 is equal to W9, W10 is equal to W3, and W2 is equal to W11. That said, in an alternate embodiment, W6 is greater than or less than W7, W5 is greater than or less than W8, W4 is greater than or less than W9, W3 is greater than or less than W10 and/or W2 is greater than or less than W 11. W1 is less than all of the other widths W, although in an alternate embodiment, it can be equal to one or more of the aforementioned widths W. Indeed, this alternate embodiment would be the case in the scenario where the conductor continuously decreased/increased in width. This is because in an exemplary embodiment, because the conductor is configured such that the flow of current flows in the same direction (counterclockwise or clockwise with respect to the view of FIG. 5A) in both layers (again, with respect to the view of FIG. 5A), the portions of the conductor on the bottom layer, with respect to the cross-section of FIG. 7, will have widths that are less than those immediately above (where FIG. 7 corresponds to the portion of FIG. 6 on the left side of the axis 699), because the wider portion of a given turn would correspond to the portion closest to the via that extends from the top layer to the bottom layer). If FIG. 7 represented the portion of FIG. 6 on the right side of the axis 699, the widths on the bottom would be greater than those on the top.

Still further, as can be seen, the turns are separated by a given space "S." As can be seen, turns 1 and 2 are separated by space S1, turns 2 and 3 are separated by space S2, turns 3 and 4 are separated by space S3, turns four and 5 are separated by space S4, turns 5 and 6 are separated by space S5, turns seven and eight are separated by space S6, turns 8 and 9 are separated by space S7, turns 9 and 10 are separated by space S8, and turns 10 and 11 are separated by space S9. In the embodiment depicted herein, S6 is equal to S5, S7 is equal to S4, S8 is equal S3, and S9 is equal to S2. That said, in an alternative embodiment, S5 is greater than or less than S6, S4 is greater than or less than S7, S3 is greater than or less than S8, S2 is greater than or less than S9. S1 is less than all of the other spaces S, although in an alternate embodiment, it can equal one or greater than or more the aforementioned spaces S.

In an exemplary embodiment, the space(s) between the turns are the same. That is, S1 equals S2 which equal S3 which equals S4 which equals S5 which equals S6 which equals S7 which equals S8 which equals S9. In an alternate embodiment, the spaces between the turns are different. Some additional details of these features will be described below.

In view of the above, in an exemplary embodiment, there is an inductance communication coil, such as coil 574A or 574B, comprising a conductor having at least one conductive turn, wherein a width of the conductor is wider at a first location relative to that at a second location on the same turn (e.g., with respect to FIG. 5A, locations L1 and L2 on turn 7). Further, in view of the above, in an exemplary embodiment, there is an inductance communication coil, such as coil 574A or 574B, comprising a conductor having at least one conductive turn, wherein a width of the conductor is wider at a first location relative to that at a second location on a different turn (e.g., with respect to FIG. 5A, locations L1 and L3 on turns 7 and 8, respectively). As can be seen, the wider location is at a turn that is an outer turn relative to the narrower turn.

Still further, in an exemplary embodiment, the aforementioned inductance communication coil comprises at least three turns, wherein the first location is at a first turn (e.g., turn 8, L3) and the second location is at a second turn (e.g., turn 9, L4), and a width of the conductor is wider at a third location relative to that at the first location, and the third location is on a third turn (e.g., turn 7, L1). As can be seen, the third turn is an outer turn relative to the second and first turns, and the first turn is an outer turn relative to the second turn.

Because in at least this embodiment, the width varies along the length of a given turn, in an exemplary embodiment, the conductor comprises a plurality of turns, wherein the first location is at a first turn and the second location is at a second turn, and the width of the conductor is wider at a third location relative to that at the first location, and the third location is on one of the first or second turns.

Still further, as can be seen from the above, in an exemplary embodiment, there is a transcutaneous inductance communication coil, comprising a conductor having a non-uniform geometry, where the non-uniform geometry is a non-uniform width. In this regard, the conductor includes at least a first turn, a second turn and a third turn, wherein the first turn has a different width than the second turn and the third turn, and the second turn has a different width than the third turn. Still, with respect to the figures, it can be seen that an exemplary embodiment, the conductor includes more than three turns, such as a fourth turn, a fifth turn and/or a sixth turn, and a given turn has a different width than that of any of the others. That said, in at least some exemplary embodiments, widths of given turns can be the same, providing that widths of at least one other turn is different.

It is noted that all of the teachings detailed herein with respect to a set of turns on one side of the substrate of the PCB corresponds to a set of turns on the opposite side of the substrate of the PCB. In an exemplary embodiment, respective given turns are identical to one another. In this regard, in an exemplary embodiment, there is an inductance communication coil that includes a first turn located on a first side of a printed circuit board substrate and a second turn located on a second side of the substrate. In an exemplary embodiment, the width of the first turn is the same as the width of the second turn at least along substantially all of the turns. In an exemplary embodiment, the turns are mirror images of one another and/or duplicities of one another located on different levels of the inductance communication component, save for the sections connecting to the leads/feedthroughs (the portion that extends from one side of the substrate to the other side of the substrate, sometimes referred to as vias). In another exemplary embodiment, the turns are a copy that has been rotated through 180 degrees about an axis perpendicular to the coil's main axis and passing through the sections connecting to the leads/feedthroughs.

It is noted that in an exemplary embodiment, with respect to the aforementioned first, second, and third turns, the respective widths vary linearly. This is also the case with respect to fourth, fifth, and/or sixth turns of such as present. That is, by way of example only and not by way of limitation, W5 can be 0.95×W6, W4 can be 0.9×W6, W3 can be 0.85×W6, W2 can be 0.8×W6, W1 can be 0.75×W6. That said, in an alternate embodiment, the widths of at least three turns vary non-linearly. In an exemplary embodiment, the widths of these three or more turns vary exponentially.

In an exemplary embodiment, the track width/conductor width varies as follows with n corresponding to a given turn, and the subscript corresponding to turn number 6:

$$W_5 = W_6 \times (1-\alpha)$$

$$W_4 = W_6 \times (1-2\alpha)$$

$$W_3 = W_6 \times (1-3\alpha)$$

$$W_n = W_6 \times (1-(N-n)\alpha)$$

where N is the total number of turns, and $\alpha$ is a scaling factor.

In an alternate embodiment, a non-linear change in trace width/conductor width varies as follows, with the subscript corresponding to the denominated turn, and n corresponding to the given turn:

$$W_5 = W_6 \times (1-\beta)$$

$$W_4 = W_5 \times (1-\beta)$$

$$W_3 = W_4 \times (1-\beta)$$

$$W_n = W_{n+1} \times (1-\beta)$$

where $\beta$ is a scaling factor.

Figure 8:
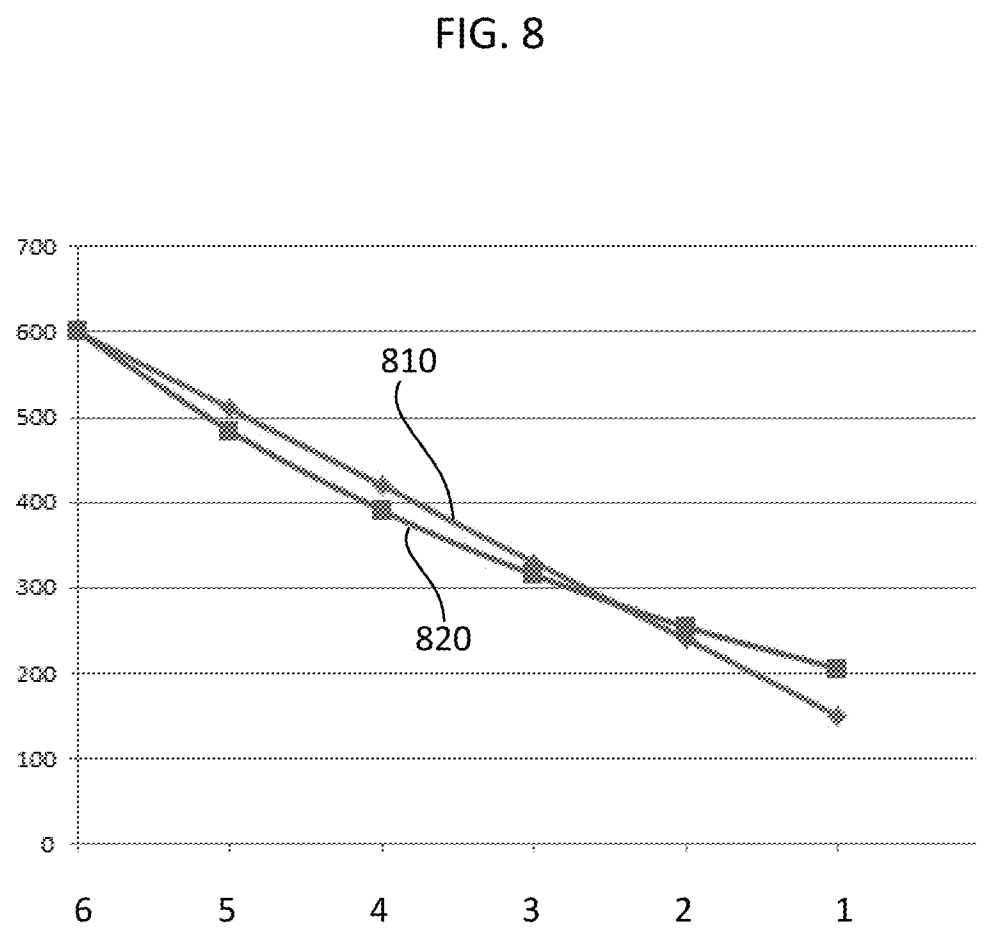

FIG. 8 depicts exemplary data plots for the linear (curve 810) and non-linear (curve 820) embodiments, where the X axis is the track/turn number, and the Y axis is the width of in micrometers.

It is noted that the above equations and plots are simply exemplary embodiments. Other trace width regimes can be utilized.

In this regard, in an exemplary embodiment, different width regimes can have different resulting coil quality factors Q. That is, a given width regime which yields an optimal Q factor for a coil with a first set of constraints (size, shape, transmission distance) might not necessarily result in an optimal Q factor for a coil with a second set of constraints. Accordingly, a method entails manufacturing an inductance communication component by empirically and/ or analytically optimizing the widths for different width regimes.

In view of the above, in an exemplary embodiment, there is an inductance communication component having an inductance coil, where the outer diameter (D6 with respect to FIG. 6) of the coil is controlled or at least influenced by the given environment/utilization of the inductance communication component. In an exemplary embodiment, the outer diameter is as large as utilitarianly feasible. With respect to a transcutaneous inductance component located above the mastoid bone for a hearing prosthesis, that outer diameter can be between about 25 mm to about 40 mm, such as, for example, 30 mm. Accordingly, in an exemplary embodiment, there is a method of manufacturing an inductance communication component that entails determining an outer diameter that is utilitarianly feasible, and in at least some exemplary embodiments, this outer diameter is as large as possible, or at least corresponds to a diameter such that the coupling factor K with the other inductance component in which the inductance communication component will be in communication with has utilitarian value.

Thus, having established the outer diameter of the coil, the width of the outermost turn, turn 6 (or 7) in the embodiment of FIG. 6 is established, and the widths of the remaining turns are then established, where a given spacing S is used between each turn. In an exemplary embodiment, the spacing S is constant, and can be determined based on manufacturing capabilities. The width of the outer turn (turn 6) can be iterated, and thus the width of the other turns will be iterated based on one or more of the above formulas etc., to determine the widths, where there can be a limit on the inside diameter of the coil (e.g., so as to avoid the magnet). Still further, instead of utilizing the above equations and/or alternate equations, all of the widths can be iterated independently. Any algorithm that can enable utilitarian widths to be developed can be utilized at least some exemplary embodiments.

The embodiment described above utilizes a constant spacing S between the turns. In at least some exemplary embodiments, this spacing is between about 50 and 500 micrometers. In an exemplary embodiment, the spacing S is about 50, 60, 70, 80, 90, 100, 110, 120, 130, 140, 150, 160, 170, 180, 190, 200, 210, 220, 230, 240, 250, 260, 270, 280, 290, or 300 or more micrometers or any value or range of values therebetween in about 1 micrometer increments (66 micrometers, about 89 micrometers, about 103 micrometers to about 177 micrometers, etc.). In an exemplary embodiment, the spacing as can be determined empirically and/or based on manufacturing capabilities. In this regard, in an exemplary embodiment, different respective spacings S for different width regimes can have different resulting coil quality factors Q. That is, in an exemplary embodiment, a given spacing S for first width regime which yields an optimal Q factor might not necessarily result in an optimal Q factor for a second width regime. Accordingly, a method entails manufacturing and inductance communication component by empirically and/or analytically optimizing the spacing S between the turns of a given coil for different width regimes.

It is further noted that while the embodiments detailed above are directed towards a spacing that is constant between all of the turns, in an alternative embodiment, the spacing S can vary between two or more turns relative to two or more other turns. That is, with respect to FIG. 7, S1 can be equal to or different from S2, S3, S4 and/or S5, S2 can be equal to or different from S3, S4 and/or S5, S3 can be equal to or different from S4 and/or S5 and S4 can be equal to or different from S5, etc. The differences can change linearly and/or nonlinearly across three or more different spacings. Any arrangement of widths and/or spacings that can enable the teachings detailed herein and/or variations thereof to be practiced can utilize in at least some exemplary embodiments.

In an exemplary embodiment, the spacing between conductors varies as follows with n corresponding to a given space, and the subscript corresponding to the space number:

$$S_4 = S_5 \times (1-\theta)$$

$$S_3 = S_5 \times (1-2\theta)$$

$$S_2 = S_5 \times (1-3\theta)$$

$$S_n = S_5 \times (1-(N-n)\theta)$$

where N is the total number of spaces, and $\theta$ is a scaling factor.

In an alternate embodiment, a non-linear change in trace spacing/conductor spacing varies as follows, with the subscript corresponding to the denominated turn, and n corresponding to the given space:

$$S_4 = S_5 = (1-\lambda)$$

$$S_3 = S_4 \times (1-\lambda)$$

$$S_2 = S_3 \times (1-\lambda)$$

$$S_n = S_{n+1} \times (1-\lambda)$$

where $\lambda$ is a scaling factor.

The embodiments depicted above present a width that is continuously changing along the conductor path (changing in an analogue manner). In an alternate embodiment, at least one of the first turn, the second turn or the third turn or the fourth turn or the fifth turn and/or the sixth turn has a uniform width over substantially all of the turn. In this regard, FIG. 8 depicts an alternate embodiment of a coil 874, where the width of the conductor changes in a digital manner. In an alternate embodiment, the widths change in a digital manner along the given turn. For example, after every 15° subtended by a given turn, the width can decrease by a given amount, either immediately (e.g., a cliff like reduction in width) or over a number of degrees (e.g., a funnel like reduction in width).

Figure 9:
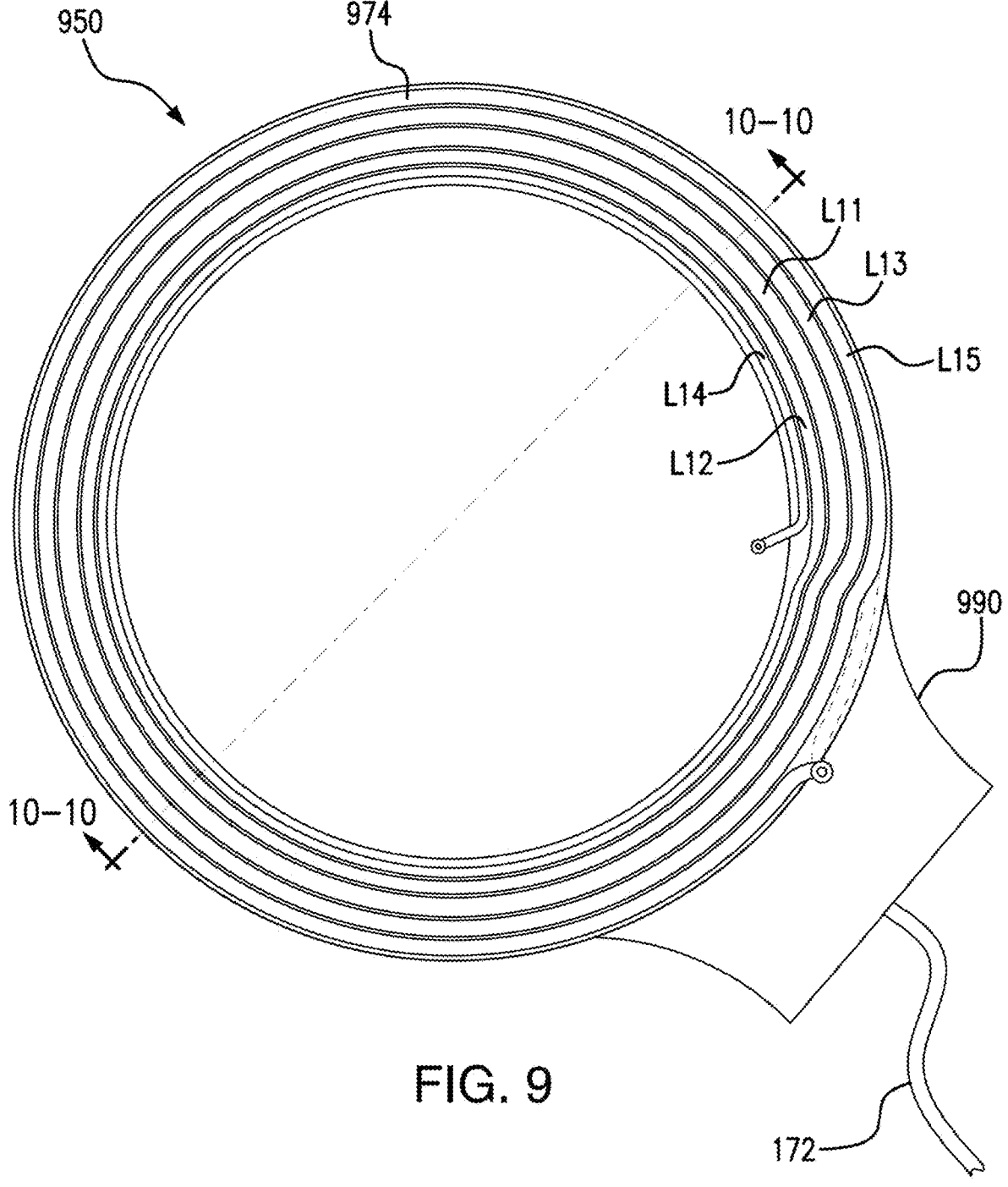
FIG. 9 is an exemplary conceptual schematic of a top view of another exemplary printed circuit board of an exemplary embodiment.

FIG. 9 depicts an exemplary embodiment of printed circuit board (PCB) 950 corresponding to a printed circuit board of an external inductance communication component corresponding with respect to functionality thereof to external inductance communication component 170 of FIG. 1B presented above. As can be seen, FIG. 9 depicts a coil 974 comprising a conductor that includes a plurality of turns, where the conductor has a non-uniform width. In the exemplary embodiment of FIG. 9, the middle turn (turn 3) is the widest. That is, the width of the conductor in the middle turn is greater than the width of the conductor in the remaining turns, including the outer turn (turn 1) and the inner turn (turn 5). The conductor has a width W that at least generally initially increases with location (in discrete increments, as can be seen, but in alternative embodiments, can increase continuously) along the conductor from the portion of the conductor proximate to the connection/interface 990 with the cable 172, where the width W is measured normal to a local longitudinal axis of the conductor of the coil 974, and then at least one of has a constant width W for the remainder or has a width that generally decreases with location (continuously or in discrete decrements) along the conductor.

It is noted that the aforementioned increase in width W can start immediately with respect to a given turn (e.g., at the 6 o'clock position), or can start somewhere downrange of a given turn. Additional exemplary variations of the width of the conductor will be described below. However, for the purposes of the present discussion, the coil 974 is a coil that has an increase in width beginning at about the 6 o'clock position closest to the connection interface 990. The aforementioned decrease in width W can start immediately with respect to a given turn (e.g., at the 6 o'clock position), or can start somewhere downrange of a given turn. However, for the purposes of the present discussion, the coil 974 is a coil that has a decrease in width beginning at about the 6 o'clock position. Conversely, in an alternate embodiment, the coil 974 can be a coil that continuously increases in width with distance from the 6 o'clock position closest to the connection interface 990 until the aforementioned stop in the increase in width. The aforementioned decrease in width W can start immediately with respect to a given turn (e.g., at the 6 o'clock position), or can start somewhere downrange of a given turn. In this alternate embodiment, the coil 974 can be a coil that continuously decreases in width with distance from the 6 o'clock position at the location where it stops increasing in width.

In view of FIG. 9, in an exemplary embodiment, there is an inductance communication coil, such as coil 974, comprising a conductor having at least one conductive turn, wherein a width of the conductor is wider at a first location (e.g., location L11 in FIG. 5) relative to that at a second location (e.g., location L12 and/or L14) and a third location (L13 and/or L15, respectively), which locations are respectively located at an inner turn and an outer turn relative to the turn at the first location.

Figure 10:
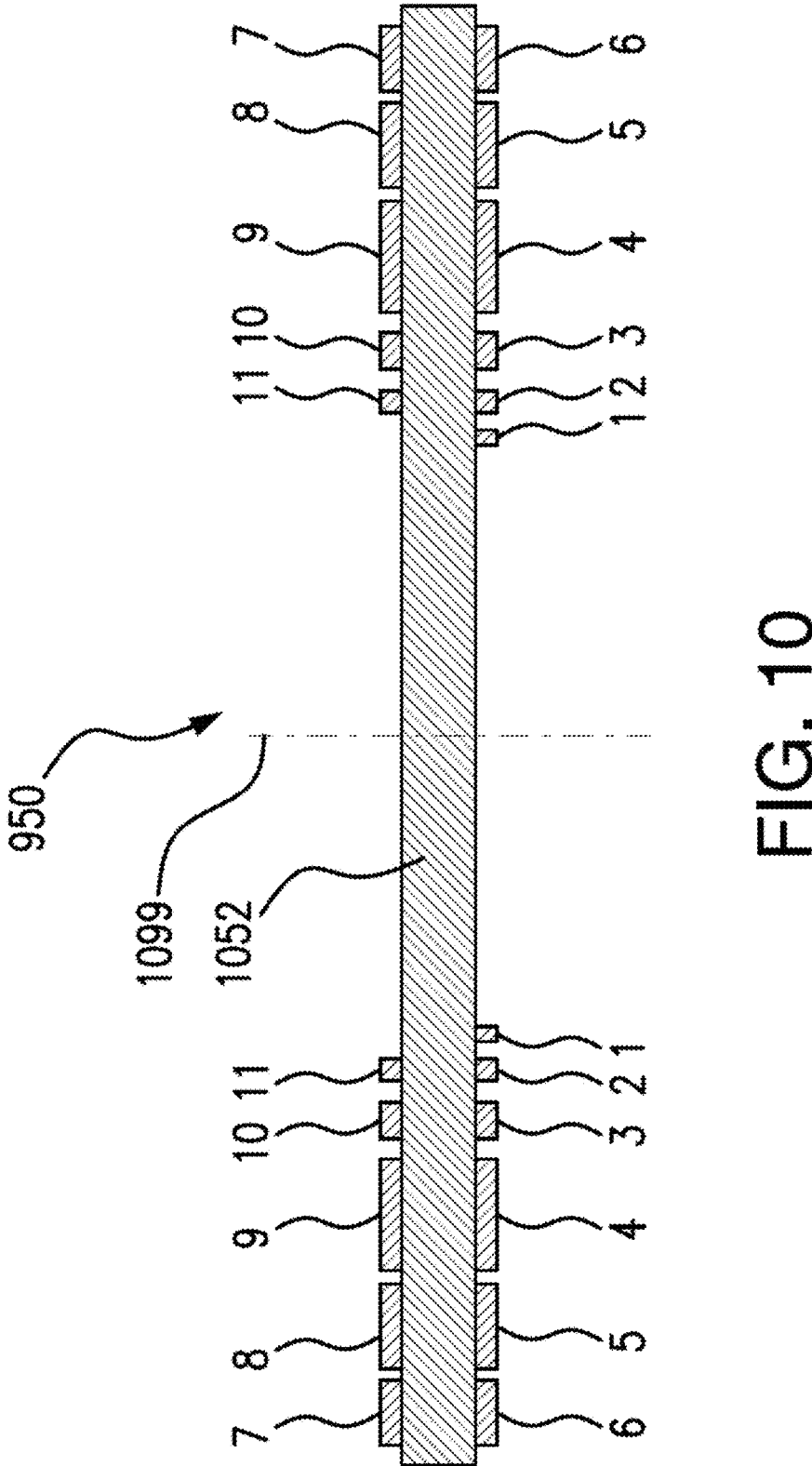
FIG. 10 is an exemplary cross-sectional view of the exemplary circuit board of FIG. 9.

FIG. 10 depicts a cross-sectional view of the PCB 950 of FIG. 9 taken along the line 9-9 which extends between the 9 o'clock position to the 3 o'clock position. More specifically, FIG. 10 depicts substrate 1052 having located thereon a conductor including turns 1-11. Turns 1-6 are located on one side of the substrate, and turns 7-11 are located on the other side of the substrate. As seen, respective turns on respective layers are aligned with one another and have the same widths (e.g., turn 6 has the same width as turn 7, turn 4 has the same width as turn 9, etc.), although in alternate embodiments, this is not the case. Further, it is noted that while the bottom turns include one more turn than the top turns, in an alternate embodiment, the number of turns are equal between the top and bottom or, in an alternate embodiment, the top includes more turns than the bottom.

Axis 1099 constitutes the axis of rotation of the turns and/or the longitudinal axis of the PCB 950/center of the PCB 950.

It is noted that in an embodiment where the width W changes along a given turn (e.g., constant change in W along a turn), the widths of the cross-sections of turns 5, 6, 7, and 8 on the left side of axis 1099/the distance between the outside of a given turn and the inside of a given turn as measured across the top surface the conductor will be less than those on the right side of axis 699, owing to the fact that the width increases in a constant manner with movement along the conductor until it stops increasing. (The opposite will be the case if the windings are wound in the opposite direction as that depicted in FIG. 9.) Conversely, the widths of a given turn are the same on both sides of the axis 1099, where the widths increase in a digital manner according to FIG. 9. Still further, it is noted that the widths of the cross-sections of turns 2, 3, 10, and 11 on the left side of axis 1099/the distance between the outside of a given turn and the inside of a given turn as measured across the top surface the conductor will be greater than those on the right side of axis 1099, owing to the fact that the width decreases in a constant manner with movement along the conductor after the width stops increasing, for embodiments where the width decreases in a constant manner with movement along the conductor. (The opposite will be the case if the windings are wound in the opposite direction as that depicted in FIG. 9.) Conversely, the widths of a given turn are the same on both sides of the axis 1099 for the embodiment of FIG. 9, where the widths increase a digital manner again as will be described in greater detail below.

Figure 11:
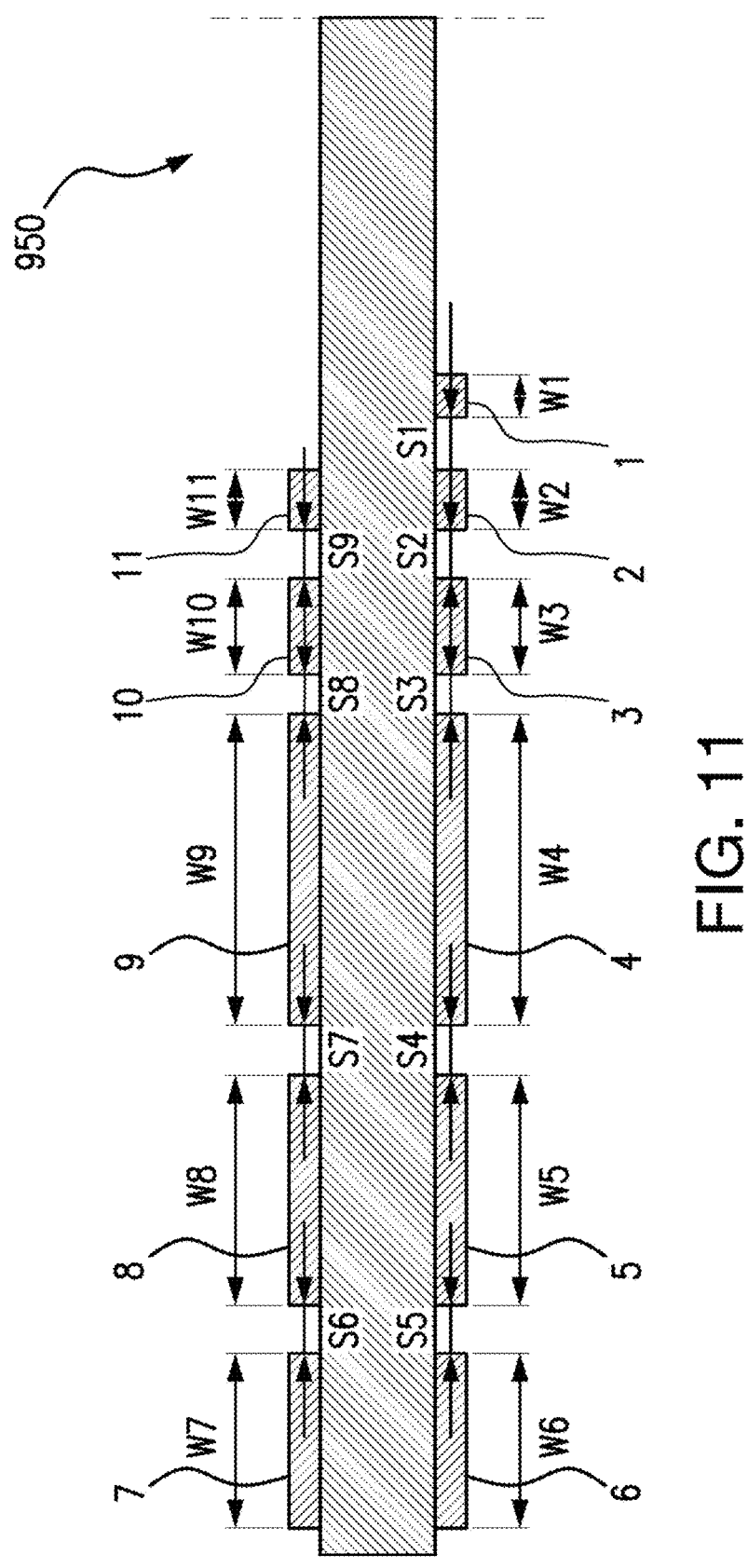
FIG. 11 depicts a detailed view of the exemplary cross-sectional view of FIG. 10.

FIG. 11 depicts a close-up view of the left portion of the PCB 950. As can be seen, each trace includes a respective width W (W1, W2, W3, W4, W5, W6, W7, W8, W9, W10, and W11), where W6 is less than W5 which is less than W4 which is greater than W3 which is greater than W2 which is greater than W1 (where W6 and W5 are greater than W3, W2 and W1 (but this can be reversed—W3 can be greater than W5, W2 can be greater than W6, both of or one of W3 or W2 can be greater than W6 and/or W5, etc.)) and W7 is less than W8 which is less than W9 which is greater than W10 which is greater than W11 (where W7 and W8 are greater than W10, and W11 (but this can be reversed—W10 can be greater than 8, W11 can be greater than 7, both of or one of W10 or W11 can be greater than W7 and/or W8, etc.))

Further, in this exemplary embodiment, W6 is equal to W7, W8 is equal to W5, W4 is equal to W9, W10 is equal to W3, and W2 is equal to W 11. That said, in an alternate embodiment, W6 is greater than or less than W7, W5 is greater than or less than W8, W4 is greater than or less than W9, W3 is greater than or less than W10 and W2 is greater than or less than W11. W1 is less than all of the other widths W, although in an alternate embodiment, it can be equal to one or more of the aforementioned widths W.

Still further, as can be seen, the turns are separated by a given space S. The spacing corresponds to that detailed above with respect to FIG. 7.

In view of the above, in an exemplary embodiment, there is an inductance communication coil, such as coil 974, comprising a conductor having at least one conductive turn, wherein a width of the conductor is wider at a first location (e.g., with respect to FIG. 9, location L11) relative to that at a second location on a different turn (e.g., with respect to FIG. 9, locations L12 and L13). As can be seen, the wider location is at a turn that is respectively an inner turn and an outer turn relative to respective narrower turns.

Still further, in an exemplary embodiment, as can be seen in FIGS. 9-11, the aforementioned inductance communication coil comprises at least three turns, wherein the first location is at a first turn and the second location is at a second turn and a width of the conductor is wider at a third location relative to that at the first location, and the third location is on a third turn. As can be seen, the third turn is an outer turn relative to the second turn and an inner turn relative to the first turn, and the first turn is an outer turn relative to the second and third turns.

The various local features described above with respect to FIGS. 5-7 are applicable to the embodiment of FIGS. 9-11.

In view of the above, in an exemplary embodiment, there is an inductance communication coil, such as coil 974, comprising a conductor having at least three conductive turns, wherein a width of the conductor is wider at a first location (e.g., L13) relative to that at a second location (e.g., L12), where the locations are on two different turns. Still further, a width of the conductor is wider at a third location (e.g., L11) relative to that at the first location, where the third location is on a different turn (a third turn) from the turns on which the first and second locations are located. The third turn is an outer turn relative to the second turn, and the first turn is an outer turn relative to the second turn and the third turn. That said, in an alternate embodiment, where the wider of the turns that parallel or otherwise run along with the widest turn is located on the inside of the widest turn instead of the outside of the widest turn, there is an inductance communication coil, such as coil 974, comprising a conductor having at least three conductive turns, wherein a width of the conductor is wider at a first location relative to that at a second location, where the locations are on two different turns. Still further, a width of the conductor is wider at a third location relative to that at the first location, where the third location is on a different turn (a third turn) from the turns on which the first and second locations are located. The third turn is an outer turn relative to the first turn, and the third turn is an inner turn relative to the second turn.

Moreover, in an exemplary embodiment where the conductor comprises a plurality of turns, where the width varies along a given turn, the aforementioned first location can be at a first turn and the aforementioned second location can be at a second turn, a width of the conductor can be wider at a third location relative to that at the first location, and the third location is on/at one of the first or second turns.

Still further, in an exemplary embodiment, the conductor of the coil includes a first turn, a second turn and a third turn, wherein the second turn is an outer turn relative to the first turn, and the third turn is an outer turn relative to the second turn. The second turn is wider than the width of the first turn and the width of the third turn. Moreover, in an exemplary embodiment, the conductor includes a fourth turn that is an inner turn relative to the first turn and the conductor includes a fifth turn that is an outer turn relative to the third turn. A width of the fourth turn is narrower than the width of the first turn and a width of the fifth turn is narrower than the width of the third turn.

As seen above, the coils of the embodiments presented above include a conductor that has components (e.g., five turns) on a first side of a printed circuit board substrate and components (e.g., six turns) on a second side of a printed circuit board substrate. That is, a given coil includes turns located at two different levels/tiers of the external inductance communication component. In an exemplary embodiment, the inductance coil is part of a printed circuit board or is supported by a substrate, and the coil includes at least three turns. A conductive path including the at least three turns is such that the path extends from a first turn to a second turn and then to a third turn of the at least three turns. The second turn is located at a different elevation with respect to printed circuit board (or substrate supporting the turns) than the first turn and the third turn.

It is noted that in alternate embodiments, turns can be located at three or more different levels/tiers (this will be discussed in greater detail below). That said, in alternative embodiments, the coils (all the coils) can be located on the same level/same elevation. Any arrangement that will enable the teachings detailed herein and/or variations thereof to be practiced can be utilized in at least some exemplary embodiments.

Still with respect to embodiments where components of the conductor are located at different levels, it is noted that in an exemplary embodiment, where a first turn is located at a first tier and a second turn is located at a second tier, a width of the first turn is the same as a width of the second turn at least along substantially all of the respective turns. However, in an alternate embodiment, a width of the first turn is the same as a width of the second turn at a location on the first turn that is less than substantially all of that turn (e.g., at a single cross section of the first turn, over about half of a turn of the first turn, etc.). In some embodiments, the widths of aligned turns (e.g., turns 6 and 7 of FIG. 11) are identical at least at substantially all cross-sections taken lying on a plane parallel to and on the axis 1099, at least where the turns overlap. In an exemplary embodiment, if cross-sections are taken in one degree increments (360 cross-sections in total), the widths will be the same for about 180, 190, 200, 210, 220, 230, 240, 250, 260, 270, 280, 290, 300, 310, 320, 330, 340, 350, or even 360 of these or any value or range of values therebetween in 1 increment.

As noted above, in an exemplary embodiment, the widths of the turns vary non-linearly from turn to adjacent turn. In an exemplary embodiment, the widths vary exponentially.

Moreover, the features detailed above with respect to the varying widths of the conductors can be quantified in terms of a conductor that has a plurality of turns, and a surface area of a first turn is different than that of the second turn beyond that due to the difference in circumference and/or diameter. That is, two exemplary turns having the same thickness will still have different surface areas if a diameter of one of the turns is different than that of the other turn (e.g., one turn is an inner turn and another turn is an outer turn). Thus, because the widths vary, the surface area of an inner turn will be different than that of the outer turn by an amount that cannot be explained due to mere difference in diameter. In an exemplary embodiment, this difference is a difference were all other factors are the same (or the difference is at least substantially entirely due to the differences in width, all other factors being the same). Corollary to this is that in an exemplary embodiment, there is a conductor that has a plurality of turns, and a radius normed surface area of a first turn is different than that of the second turn. That is, if the aforementioned phenomenon associated with the surface area being different due to differences in diameters of different turns were accounted for (e.g., dividing the surface area by the inner, middle, or outer radius of each turn, with or without another norming variable), the resulting surface area (the normed surface area) would still be different. This is as opposed to what would result of a conductor had a constant width from turn to turn, where the radius normed surface area of the turns would be the same.

Still with reference to the embodiment of FIGS. 9-11, in an exemplary embodiment, the track width/conductor width varies as follows with the subscript corresponding to the turn number:

$$W_6 = W_4 \times (1 + 2\Omega_{out})$$

$$W_5 = W_4 \times (1 + \Omega_{out})$$

$$W_3 = W_4 \times (1 + \Omega_{in})$$

$$W_2 = W_4 \times (1 + 2\Omega_{in})$$

$$W_1 = W_4 \times (1 + 3\Omega_{in})$$

where $\Omega_{out}$ is a scaling factor for the turns on the outside of the widest turn (W4), and $\Omega_{in}$ is a scaling factor for the turns on the inside of the widest turn (W4).

In an alternate embodiment, a non-linear change in trace width/conductor width varies in a non-linear manner according to alternate equations that yield a non-linear result.

In an exemplary embodiment, the spacing between conductors varies as follows, with the subscript corresponding to the turn number:

$$S_5 = S_3 \times (1 + 2\dot{\eta}_{out})$$

$$S_4 = S_3 \times (1 + \dot{\eta}_{out})$$

$$S_2 = S_3 \times (1 + \dot{\eta}_{in})$$

$$S_1 = S_3 \times (1 + 2\dot{\eta}_{in})$$

where $\dot{\eta}$ is a scaling factor.

In an alternate embodiment, a non-linear change in trace spacing/conductor spacing varies in a non-linear manner according to alternate equations that yield a non-linear result.

Again, any track width and/or spacing that can enable the teachings detailed herein and/or variations thereof to be practiced can be utilized in at least some embodiments.

It is noted that in an exemplary embodiment, in a conductor having a plurality of turns, the DC resistance of the conductor varies along a path between a first location and a second location, wherein the plurality of turns are electrically located between the first location and the second location. In this regard, by way of example only and not by way of limitation, the first location can be on turn 1 and the second location can be on turn 4 (or the first location could be on the lead leading to turn 1 (the lead that connects the coil to the other components of the implantable device), and the second location could be on turn 3 or, in the case where leads are used to connect a given turn in a serial, discrete, manner, the lead connecting turn 2 to turn 3). Still further, in an exemplary embodiment, the DC resistance of the conductor can vary along a path between two locations that are on the same turn. Indeed, by way of example only and not by way of limitation, the DC resistance of the conductor can vary along a path between a third location and a fourth location, where both the third location and the fourth location are located between the first location and the second location, and the third location and the fourth location are located on a single turn of the plurality of turns. In an exemplary embodiment, the various physical phenomena detailed herein (DC resistance features, Q value, etc.) are a result of the variation of the width of the turns.

That said, in an alternative embodiment, again by way of example only and not by way of limitation, DC resistance of the conductor is constant along a path between a third location and a fourth location, where both the third location and the fourth location are located between the first location and the second location. The third location and the fourth location are located on a single turn of the plurality of turns.

In an exemplary embodiment where the inductance coil includes a plurality of turns, a point to point DC resistance over a first arc of at least about 180 degrees on an outer turn of the plurality of turns is lower than that over a second arc, spanning the same angle as the first arc (e.g., if the first arc is 100 degrees, the second arc is 100 degrees, if the first arc is 75 degrees, the second arc is 75 degrees, etc.) on an inner turn of the plurality of turns. Conversely, in an alternate exemplary embodiment where the inductance coil includes a plurality of turns, a point to point DC resistance over a third arc of at least about 180 degrees on an outer turn of the plurality of turns is greater than that over a fourth arc, spanning the same angle as the third arc (e.g., if the third arc is 100 degrees, the fourth arc is 100 degrees, if the third arc is 75 degrees, the fourth arc is 75 degrees, etc.) on an inner turn of the plurality of turns.

FIG. 12 presents an exemplary flowchart 1200 for an exemplary method accordingly to an exemplary embodiment, as will now be described.

Method 1200 includes method action 1210, which entails capturing an ambient sound with a microphone. In an exemplary embodiment, this method action is executed using the cochlear implant system 10 detailed above, where the microphone is either implanted in the recipient or is external to the recipient (e.g., the totally implantable hearing prosthesis is utilizing an external microphone). Method 1200 further includes method action 1220, which entails converting the captured ambient sound to a first signal. In at least some exemplary embodiments, this first signal corresponds to the output of the aforementioned microphone.

Method 1200 also includes method action 1230, which entails transcutaneously transmitting, using a first coiled inductance antenna located outside the skin of the recipient, such as over a mastoid bone of the recipient (e.g., external coil 130 of FIG. 1A, corresponding to an embodiment detailed herein or a variation thereof) an inductance signal based on the first signal to an implanted second coiled inductance antenna. Thereafter, method action 1240 is executed, which entails evoking a hearing percept based on a signal from the second coiled inductance antenna, the second signal being generated by the inductance signal. It is noted that in an exemplary embodiment, method actions 1210, 1220, 1230 and 1240 are executed automatically.

In the execution of method action 1230, a current is applied to the first coiled inductance antenna to generate a magnetic field, thereby transmitting the inductance signal. In the method of 1200, an average current density at least one of increases or decreases with distance from a geometric center of turns of the first coiled inductance antenna and/or the second coiled inductance antenna over at least a portion of the distance from the geometric center.

FIG. 13 presents an exemplary flowchart 1300 for an exemplary method accordingly to another exemplary embodiment, as will now be described. Briefly, instead of transcutaneously transmitting a signal that is utilized to evoke a hearing percept, a signal is transcutaneously transmitted that it is utilized to at least one of power and/or recharge an implanted component. More specifically, method 1300 includes method action 1310, which entails transcutaneously transmitting, using a first coiled inductance antenna located over a mastoid bone of the recipient, an inductance signal to an implanted second coiled inductance antenna. Method 1300 also includes method action 1320, which entails at least one of recharging an implanted battery or powering an implanted functional component based on a signal from the second coiled inductance antenna, the second signal being generated by the inductance signal. Method action 1310 is executed by applying a current to the first coiled inductance antenna to generate a magnetic field, thereby transmitting the inductance signal. In the exemplary embodiment of method 1300, an average current density at least one of increases or decreases with distance from a geometric center of turns of the first coiled inductance antenna and/or the second coiled inductance antenna over at least a portion of the distance from the geometric center.

Figure 14A:
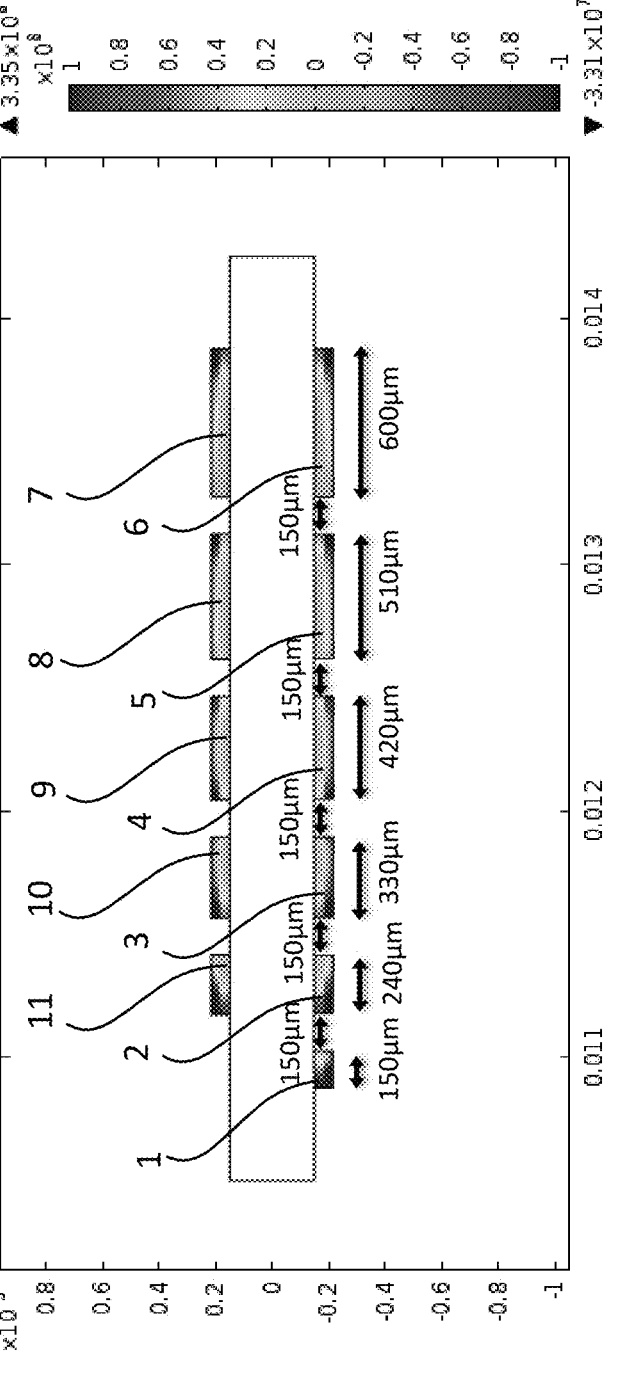
FIG. 14A presents a schematic presenting exemplary data according to an exemplary embodiment.

In view of the above, an exemplary embodiment includes an average current density that at least one of increases or decreases with distance from a geometric center of turns of a coiled inductance antenna over at least a portion of the distance from the geometric center. With reference to the embodiments of FIGS. 5A and 5B, the geometric center is axis 699, and with reference to the embodiments of FIG. 9, the geometric center is axis 1099. FIG. 14A presents a schematic presenting exemplary current densities in turns 1-11 for the embodiments of FIGS. 5A and 5B, where the X axis and the Y axis are presented in units of meters, and where the X axis represents distance from the geometric center. This current density is for a current frequency of 5 megahertz. As can be seen, where the color coded bar on the right side of FIG. 14A is in units of $A/m^2$, with distance from the geometric center, the average current density at a given cross-section of a given turn decreases with distance from the geometric center. In an exemplary embodiment, the average current density decreases with distance from a geometric center of turns of the first coiled inductance antenna over substantially all (including all) of the distance from the geometric center. With reference to FIG. 14A, it is noted that the maximum current density in this embodiment is $3.35×10^8$ $A/m^2$ and the lowest is $-3.31×10^7$ $A/m^2$.

Figure 14B:
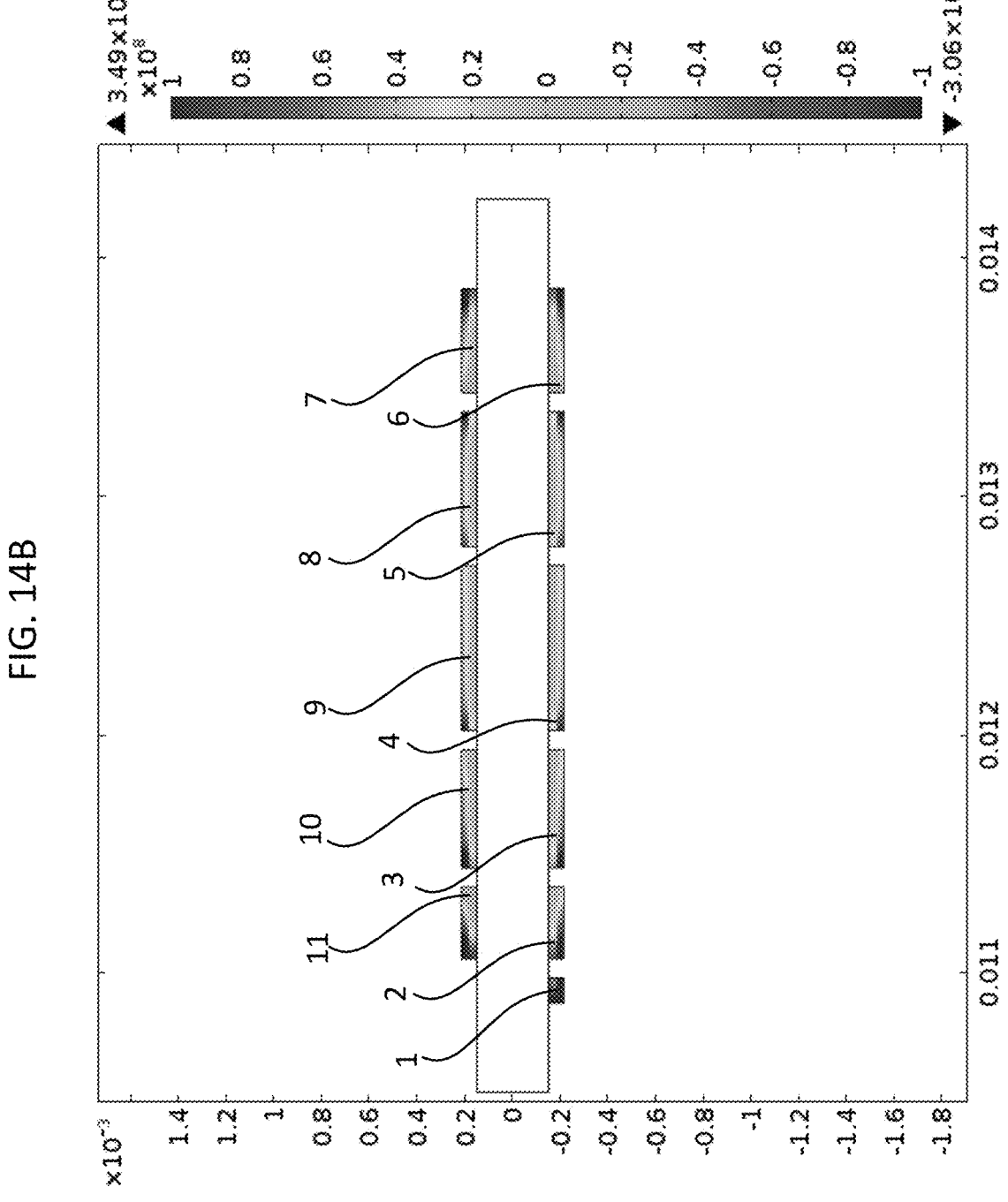
FIG. 14B presents a schematic presenting exemplary data according to another exemplary embodiment.

FIG. 14B presents a schematic presenting exemplary current densities in turns 1-11 for a variation of the embodiment of FIG. 9, where the X axis and the Y axis are presented in units of meters, and where the X axis represents distance from the geometric center. FIG. 14B is a variation of FIG. 9 because while turns 4 and 9 are the widest turns, as is the case in the embodiment of FIG. 9, turns 3 and 10 are wider than turns 6 and 7 (whereas in the embodiment of FIG. 9, turns 6 and 7 are wider than turns 3 and 10). As with FIG. 14A, the current density is for a current frequency of 5 megahertz. As can be seen, where the color coded bar on the right side of FIGS. 14A and 14B are units of $A/m^2$, with distance from the geometric center, the average current density at a given cross-section of a given turn decreases with distance from the geometric center for a portion of the distance from the geometric center (the distance from the center until turns 4 and 9), and then increases with distance from the geometric center for another portion of the distance from the geometric center. Thus, in an exemplary embodiment, there is a coil configured such that the average current density decreases over a first distance from a geometric center of turns of the first coiled inductance antenna over at least a portion of the distance from the geometric center, and the average current density increases over a second distance from the geometric center of turns of the first coiled inductance antenna over a second portion of the distance from the geometric center, wherein the portion of the distance from the geometric center corresponding to the first distance is located between the geometric center and the second portion. With reference to FIG. 14A, it is noted that the maximum current density in this embodiment is $3.49×10^8$ $A/m^2$, and the lowest is $-3.06×10^7$ $A/m^2$.

It is noted that as used herein, the term "average current density" is the average density of current in a given cross-section. In an exemplary embodiment, the average current densities of respective turns are measured on the same plane, where the plane is located on and parallel to the axis corresponding to the geometric center of the turns. In an exemplary embodiment, the plane is located such that it is normal to a tangent line of the inner and/or outer sides of the turns.

It is noted that by the average current density increasing or decreasing with distance from the geometric center, it is meant that the average current density increases along the arc of the turn as it moves outward from the geometric center (such as is the case with respect to the spiral configuration), and that for given cross-sections of the coil lying in a plane located on and parallel to the axis establishing the geometric center, the average current density for a given cross section is different than another given cross section that is a different distance from the geometric center.

At least some embodiments are configured such that the resulting inductance coil has a Q factor that has utilitarian value. In an exemplary embodiment, there is an inductance communication coil, comprising a coiled conductor including at least three turns on a first layer (e.g., the layer including turns 1-6 or the layer including turns 7-11 of the embodiments detailed above). In an exemplary embodiment, the number of turns on the first layer corresponds to 3, 4, 5, 6, 7, 8 9 or 10 turns or more. A maximum outer diameter D6 of the outermost turn (turns 6 or 7 in the exemplary embodiments detailed above) of the at least three turns (or any of the aforementioned number of turns) is about 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, or about 40 mm or any value or range of values therebetween in about 0.1 mm increments. Further, the coiled conductor is of a configuration where a bare winding thereof, when subjected to an electrical current having a frequency of 5 MHz, having one of the aforementioned number of turns within one of the aforementioned diameters, has a Q factor of one of at least 75, at least 76, at least 77, at least 78, at least 79, at least 80, at least 81, at least 82, at least 83, at least 85, at least 86, at least 87, at least 88, at least 89, at least 90, at least 91, at least 92, at least 93, at least 94 or more.

By "bare winding," it is meant that all other components of the inductance communication component are not present, such as the magnet, EMI shielding, etc. Such can be determined by way of example and not by way of limitation, by computer models, stimulations, or by holding the windings in space using materials that effectively do not impact the Q value.

Figure 14C:
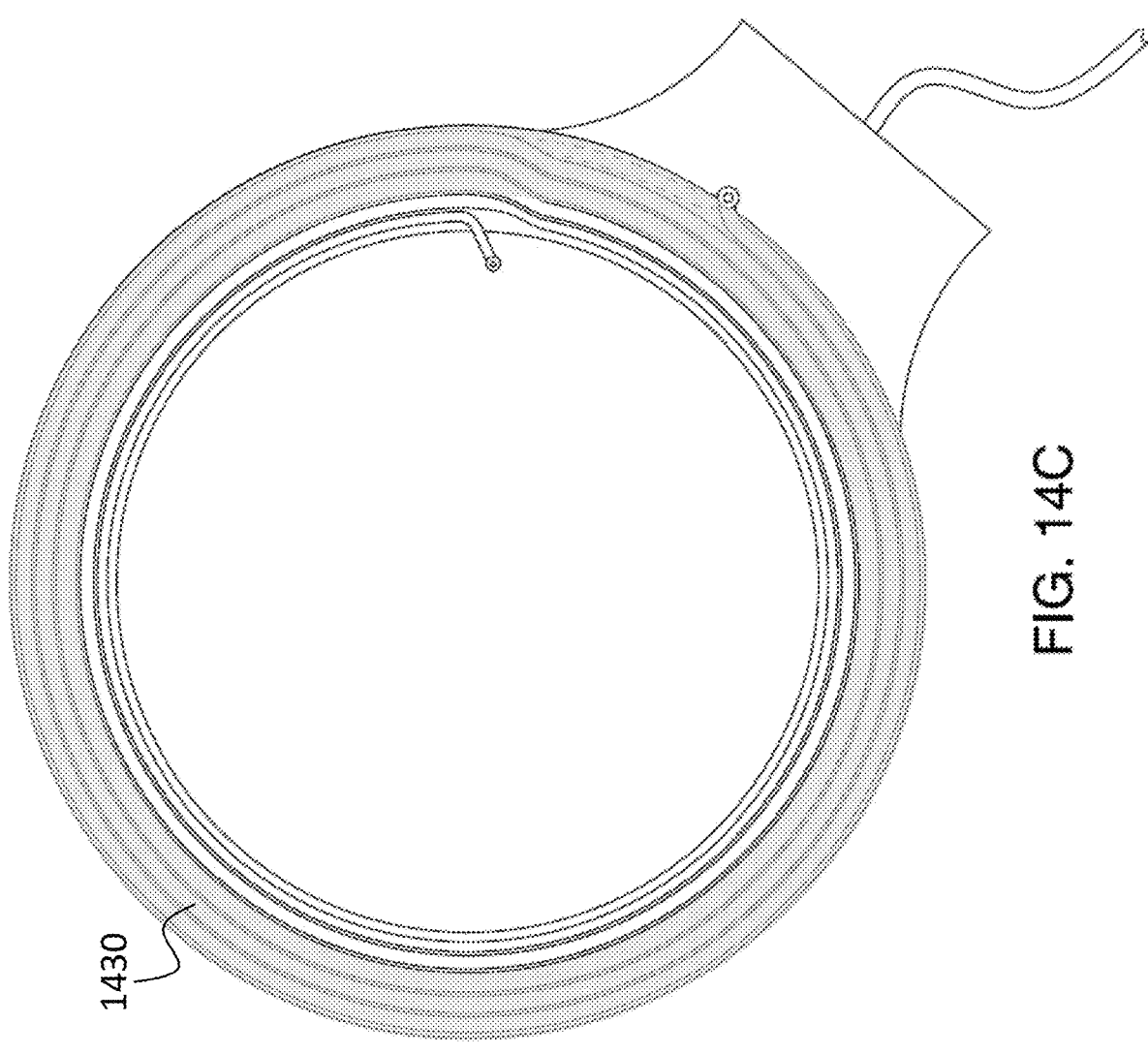
FIG. 14C presents a schematic presenting an exemplary concept of comparing some exemplary embodiments to alternate techniques of practicing inductance communication.

It is further noted that in an exemplary embodiment, a coil includes a plurality of turns, where a boundary area encompasses the plurality of turns. By way of example, FIG. 14C depicts such a boundary area 1430. In an exemplary embodiment, an effective AC resistance of a portion of the conductor located within the boundary area of an actual device under consideration is lower than that which would be the case for a hypothetical configuration having the same number of turns located within the same boundary area where the turns are spaced evenly apart from one another and where cross-sectional areas of the conductor on respective planes normal to a longitudinal axis of the conductor is non-varying with location along the conductor within the boundary area.

In an exemplary embodiment, the aforementioned hypothetical configuration is such that the volume of material making up the turns in the boundary area corresponds to that of the actual device (i.e., the device under consideration). In an exemplary embodiment, the aforementioned hypothetical configuration is such that the surface area of the turns in the boundary area corresponds to that of the actual device. In an exemplary embodiment, the aforementioned hypothetical configuration is such that the material of the turns is the same as that of the actual device. In an exemplary embodiment, the aforementioned hypothetical configuration is such that the average cross-sectional area of the turns and the boundary area corresponds to that of the actual device. In an exemplary embodiment, the only difference between the aforementioned hypothetical configuration and the actual device corresponds to the variation in the cross-sectional areas of the conductor on the respective planes. In an exemplary embodiment, the only difference between the aforementioned hypothetical configuration and the actual device corresponds to the variation in the spacing between the turns and/or the variation of the width of the turns.

In an exemplary embodiment, the only differences between the aforementioned hypothetical configuration and the actual device corresponds to the variation in the cross-sectional areas of the conductor on the respective planes and to the variation in the spacing between the turns.

In the aforementioned exemplary embodiment(s), the boundary area must include at least two turns therein because it encompasses a plurality of turns. The boundary area can include more than two turns. Indeed, in an exemplary embodiment, a coil includes a boundary area encompassing 3 turns, 4 turns, 5 turns or 6 turns. In an exemplary embodiment of all of these embodiments relating to the various numbers of turns, an effective AC resistance of a portion of the conductor located within the boundary area is lower than that which would be the case for a same number of turns located within the same boundary area where the turns are spaced evenly apart from one another and where cross-sectional areas of the conductor on respective planes normal to a longitudinal axis of the conductor is non-varying with location along the conductor within the boundary area.

It is noted that the physical phenomena associated with the resistances (DC or AC) detailed herein relate to turns on the same level (e.g., on the same side of the substrate). That said, in an alternate embodiment, the physical phenomenon associated with the resistances detailed herein relate to turns that can be on different levels, at least in some embodiments utilizing a weave feature as will be detailed below.

A variation on the concept presented above will now be described. Briefly, the variation entails utilizing, in an exemplary embodiment, the conductor having a varying width) as detailed above (or height, as will be detailed below), but where the layers on which the windings are located are alternated between PCB layers with respect to the location of the conductor as the conductor extends from the inside diameter thereof to the outside diameter thereof, and as the conductor extends from the outside diameter thereof to the inside diameter thereof.

Figure 15:
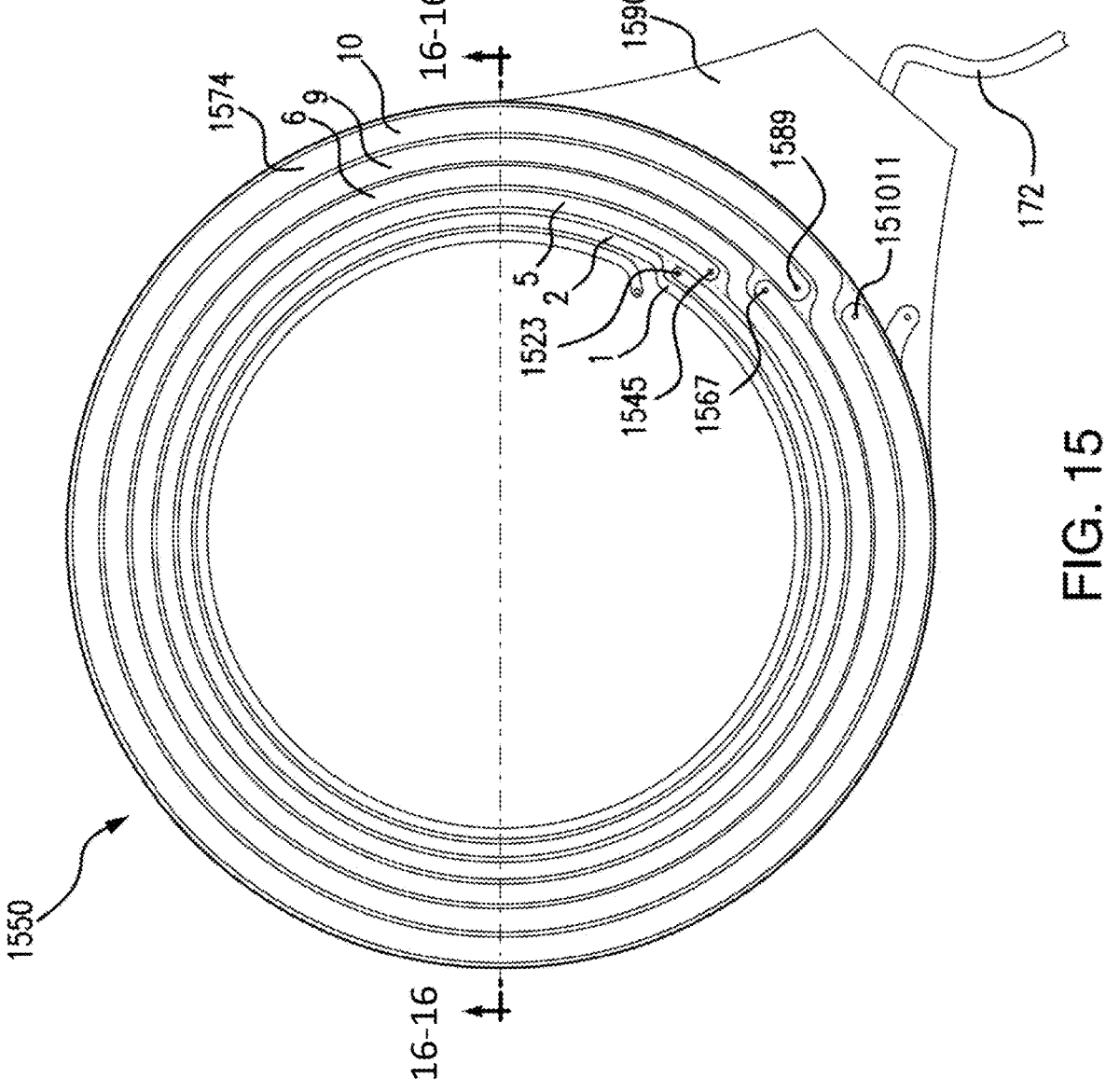
FIG. 15 is an exemplary conceptual schematic of a top view of an exemplary printed circuit board of another exemplary embodiment.

More specifically, FIG. 15 depicts an exemplary embodiment of printed circuit board (PCB) 1550 corresponding to a printed circuit board of an external inductance communication component corresponding with respect to functionality thereof to external inductance communication component 170 of FIG. 1B presented above. As can be seen, the width of the conductor varies from turn to turn. In the embodiment of FIG. 15, the width is depicted as varying in a digital manner from turn to turn, and thus the embodiment of FIG. 15 is based in part on the embodiment of FIG. 5B. It is noted that in other embodiments, the concepts that will be detailed with respect to FIG. 15 can be applied with respect to the other embodiments herein (e.g., the continuously varying width of FIG. 5A, etc.).

As can be seen, the embodiment of FIG. 15 includes a coil 1574 comprising a conductor that includes a plurality of turns. In FIG. 15, which depicts a top of the PCB, there are six (6) turns, as can be seen (as opposed to the embodiment of FIG. 5B, where there are only 5 turns on the top—again, as noted above, the number of turns on a given side of the PCB can vary from embodiment to embodiment). This is as opposed to the bottom of the PCB (the opposite side from that shown in FIG. 15), which includes five turns, as will be described in greater detail below.

More generally, it is noted that the embodiment of FIG. 15 includes five (5) turns on both the top and bottom, and an additional sixth turn on the top (or on the bottom in some alternate embodiments). As used herein, a turn entails a portion of the conductor that subtends an angle of about 360°. A beginning of a turn can be considered to begin anywhere, although in the exemplary embodiments detailed herein the turns will be described as beginning at the location closest to the connection interface 1590. With respect to the drawling of FIG. 15, each turn begins at or between the 4 and 5 o'clock position. In other embodiments, the turns can be considered to begin elsewhere.

As noted above, the coil 1574 is implemented on a PCB. That is, in an exemplary embodiment, the coils are PCB based coils. Accordingly, in an exemplary embodiment, the coils can correspond to PCB traces/conductive traces.

Figure 16:
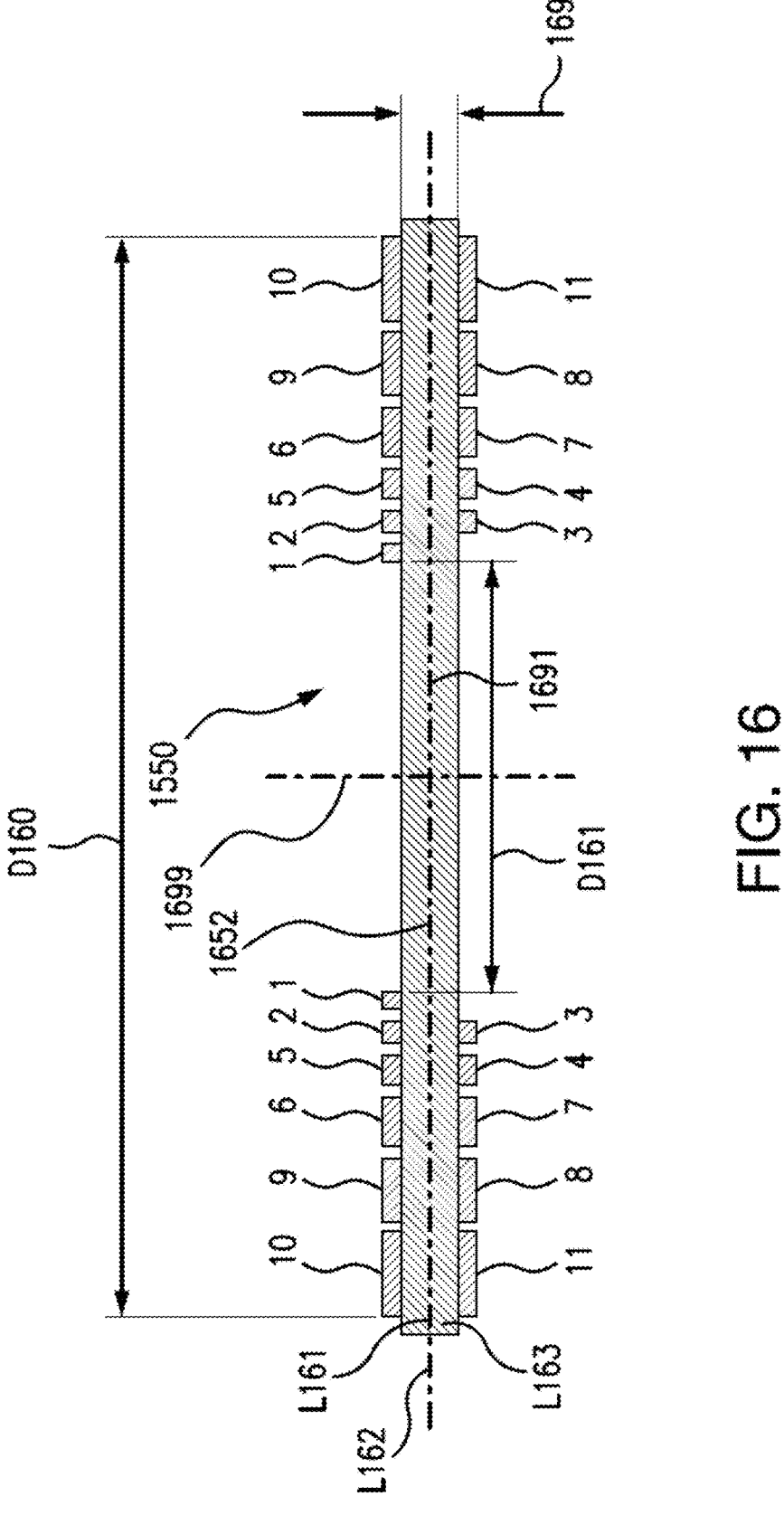
FIG. 16 is an exemplary cross-sectional view of the exemplary circuit board of FIG. 15.

In the embodiment depicted in FIG. 15, the layers on which the windings are located are alternated between PCB layers with respect to the location of the conductor as the conductor extends from the inside diameter thereof to the outside diameter thereof, and as the conductor extends from the outside diameter thereof to the inside diameter thereof. This along with the feature that the width of the conductor varies with distance from the axis of rotation of the coil. More specifically, FIG. 15 depicts turns 1, 2, 5, 6, 9 and 10, which connect via vias 1523 (where the last two groups of digits correspond to the turns connected by the via—here, turn 2 to turn 3), 1545, 1567 and 1589 and 151011 to turns located on the opposite side of the PCB. In this regard, FIG. 16 depicts a cross-sectional view taken at line 16-16 of FIG. 15, which shows the aforementioned turns, along with turns 3, 4, 7, 8, and 11. As can be seen, turns 1, 2, 5, 6, 9, and 10 are located on one side of the substrate 1652, and are centered about axis 1699, while turns 3, 4, 7, 8, and 11 are located on an opposite side of the of the substrate 1652, which turns can also be centered around axis 1699. Also as can be seen, turns 1, 2, 5, 6, 9, and 10 have widths that increase with distance from axis 1699, while turns 3, 4, 7, 8, and 11 also have widths that increase with distance from axis 1699. It is noted that while the embodiment depicted FIGS. 15 and 16 is such that the width increases with distance from the longitudinal axis 1699, in an alternate embodiment, the width can vary in a manner akin to any other arrangement detailed herein and/or variation thereof (e.g., such as according to the embodiment of FIG. 9, etc.). As can be seen, there is one (1) less turn on the bottom of the substrate 1652 than on the top of the substrate 1652. That said, in an alternative embodiment, the number of turns can be the same on both sides of the substrate 1652. Still further, in an alternative embodiment, the number of turns on the top of the substrate 1652 can be less than the number of turns on the bottom of the substrate 1652. Any arrangement of the number of turns that can enable the teachings detailed herein and/or variations thereof can be utilized in at least some exemplary embodiments.

As noted above, FIG. 16 depicts a cross-sectional view of the PCB 1550. As can be seen, respective turns on respective layers are aligned with one another and have the same widths (e.g., turn 6 is the same width as turn 7, turn 4 has the same width as turn 5, etc.). Also, as can be seen, the turns are concentric with one another (which results from the fact that they are aligned with one another—in some embodiments, the turns are concentric but not aligned with one another).

It is noted that while the following embodiments are presented in terms of having six turns on one side and five turns on the other, in some alternate embodiments, more or fewer turns can be utilized on one or both sides. Any number of turns that can have utilitarian value with respect to the teachings detailed herein can be utilized in at least some exemplary embodiments. Indeed, in an exemplary embodiment, a single turn can be utilized (which includes a single turn on each side of the substrate 1652). Still further, in some alternate embodiments, a third and/or a fourth and/or a fifth and/or a sixth or more layers of conductor componentry are utilized in some exemplary embodiments of an inductive communication component utilizing at least some of the teachings detailed herein. Note further that there can be, in some embodiments, layers of substrate outside the layers of windings (e.g., with respect to FIG. 1C, above turns 7, 8, 9, 10, 11, and below turns 6, 5, 4, 3, 2, 1). That is, in some embodiments, the windings may not be on the outer layers.

Axis 1699 constitutes the axis of rotation of the turns and/or the longitudinal axis of the PCB 1550/center of the PCB 1550.

A conductive path extending from the inner diameter (D161) of the conductor 1574 to the outer diameter of the conductor 1572 (D160) extends as follows in an exemplary embodiment: from a source or sink to turn 1, then on the same level/tier to turn 2 (where turn 2 has a width that is wider than turn 1), and then through substrate 1652 to turn 3 (which has the same width as turn 2 (at least on average—the width over the entire turn), in some embodiments), and then on the same level/tier to turn 4 (where turn 4 has a width that is wider than turn 3), and then through substrate 1652 to turn 5 (which has the same width, at least on average, as turn 4, in some embodiments), and then on the same level/tier to turn 6 (where turn 6 has a width that is wider than turn 5), and then through substrate 1652 to turn 7, and then on the same level/tier to turn 8 (where turn 8 has a width that is wider than turn 7), and then through substrate 1652 to turn 9 and then on the same level/tier to turn 10 (where turn 10 has a width that is wider than turn 9) and then through substrate 1652 to turn 11 and then to a sink or source.

Still with reference to FIG. 15, in an exemplary embodiment, it can be seen that at the beginning of the coil or location proximate the beginning of the coil, a contiguous electrical path of the conductor 1574 subtends an angle totaling almost 720° on a first level of the coil (here, the level of that of FIG. 15). That is, starting at the location where the conductor bends to begin the first turn (turn 1), the coil subtends a bit less than 360 degrees, and then juts out to the second track to begin the second turn (turn 2) and then subtends a bit less than 360° from the location where the conductor juts out to the second track, and then ends (where via 1523 then extends the electrical path to the loops beneath the level of that depicted in FIG. 15, the turns on the other side of the substrate). In totality, the conductor/electrical path subtends an angle almost 720° on the first layer/same layer. This is as opposed to an exemplary embodiment where, for example, after subtending the slightly less than 360°, the conductor ended at a via where the electrical path extended from the first level to the second level (the other side of the substrate). Such would thus only establish an electrical path that contiguously extends an angle less than 360°.

It is also noted that the aforementioned feature with respect to the path subtending an angle totaling almost 720° can also be the case with respect to the end of the conductor. Accordingly, in an exemplary embodiment, with respect to at least one of a beginning or an end of the coil or locations proximate thereto, a contiguous electrical path of the conductor subtends an angle totaling at least 600, 610, 620, 630, 640, 650, 660, 670, 675, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719 or 720 degrees on the same level (and/or no more than one of the aforementioned values).

To be clear, in this embodiment, the widths of turns 2 and 3 are the same (or at least approximately the same), at least on average, turns 4 and 5 are the same (or at least approximately the same), at least on average, turns 6 and 7 are the same (or at least approximately the same), at least on average, turns 8 and 9 are the same (or at least approximately the same), at least on average, and turns 10 and 11 are the same (or at least approximately the same), at least on average. Thus, the resulting conductive path is in the form of a weave, as is presented conceptually by the path 1710 presented in FIG. 17. Thus, in an exemplary embodiment, there is a conductor that is configured such that an electrical path extends through a first turn (turn 2 with reference to FIG. 17) on one side of the substrate and then through a second and third turn (turns 3 and 4 with reference to FIG. 17) on an opposite side of the substrate and then through a fourth and fifth turn (turns 5 and 6) on one side of the substrate and then through a sixth and seventh turn (turns 7 and 8) on the opposite side of the substrate and then through an eighth and ninth turn (turns 9 and 10) on the one side of the substrate and then through at least a tenth turn (turn 11) on the opposite side of the substrate. It is further noted that in an exemplary embodiment, the conductor is configured such that an electrical path extends through the tenth turn and then through an eleventh turn (not shown) on the opposite side of the substrate. Alternatively or in addition to this, in an exemplary embodiment, the conductor is configured such that an electrical path extends through a turn prior to the first turn (e.g., turn 1) on the one side of the substrate.

It is noted that in an alternate embodiment, the weave path can begin on the bottom as opposed to on the top of the PCB 1550 and end on the top as opposed to the bottom of the PCB 1550. Alternatively, the weave path can begin on the top or begin on the bottom and end on the bottom.

Note that the use of the aforementioned beginnings and ends are used simply to explain the weave concept in general. The conductive path extends beyond the turns (to and from the component that generates the current). Thus, the weave is a portion of the conductive path.

It is noted that all of the teachings detailed herein with respect to a set of turns on one side of the substrate of the PCB corresponds to a set of turns on the opposite side of the substrate of the PCB, at least in some embodiments. In an exemplary embodiment, respective given turns are substantially identical (which includes identical) to one another. In this regard, in an exemplary embodiment, there is an inductance communication coil (or other type of communication coil, or other types of coil for that matter—embodiments can include inductance coils that are not used exclusively for communication, as will be described below) that includes a first turn located on a first side of a printed circuit board substrate and a second turn located on a second side of the substrate. In an exemplary embodiment, the width of the first turn is the same as the width of the second turn at least along substantially all of the turns. In an exemplary embodiment, the turns are mirror images of one another and/or duplicities of one another located on different levels of the inductance communication component, save for the sections connecting to the leads/feedthroughs (the portion that extends from one side of the substrate to the other side of the substrate, sometimes referred to as vias herein) and/or the portions that connect the turn(s) to the remaining portions of the circuit (e.g., the rest of the receiver stimulator). In another exemplary embodiment, the turns are a copy that has been rotated through 180 degrees about an axis perpendicular to the coil's main axis and passing through the vias or other components connecting to the leads/feedthroughs.

In view of the above, in an exemplary embodiment, there is an inductance communication coil, comprising a first layer including a first plurality of conductive turns (turns 1, 2, 5, 6, 9, and 10 in FIG. 17) and a second layer including a second plurality of conductive turns (turns 3, 4, 7, 8, and 11 in FIG. 17) separated from the turns of the first layer by a distance (e.g., about 0.35 mm—more on this below). In this exemplary embodiment, a portion of a conductive path (e.g., the portion within circle 1720) extends through the first plurality of conductive turns and the second plurality of conductive turns. In an exemplary embodiment, the portion of the conductive path begins at an outside of a turn (e.g., outside of turn 11) of the first plurality of conductive turns or the second plurality of conductive turns and ends at an inside turn (e.g., turn 1) of the other of the first plurality of conductive turns or the second plurality of conductive turns.

It is noted that with respect to the phrase "portion of a conductive path," this does not necessarily mean that the entire path of which the portion of the conductive path is a part begins and ends as recited. It is only a portion of the conductive path that begins and ends as recited. In this regard, it is to be noted that in at least some exemplary embodiments, the conductive path extends from the component that generates the electrical current to generate the inductance field to one of the turns (e.g. turn 1 or turn 11), extends through the turns, and then extend from the last turn (e.g., the other of turn 1 or turn 11) back to the component that generates electrical current. Thus, the conductive path begins and ends outside of the turns. It is further noted that the beginning and the end of the portion of the conductive path need not have definitive beginnings and ends. That is, a portion of a conductive path can be an arbitrary portion, providing that it meets the aforementioned requirements.

Figure 18:
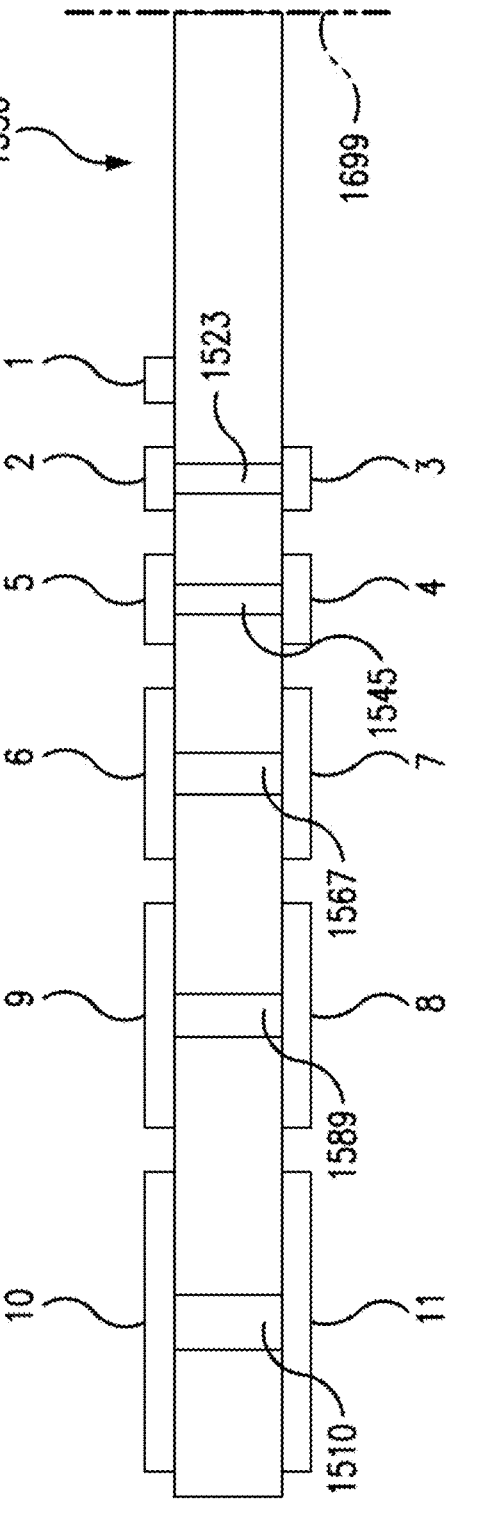
FIG. 18 depicts additional details of a conceptual exemplary cross-sectional view of FIG. 16.

As noted above, vias are utilized to connect the turns on the upper layer/tier to turns on the bottom layer/tier. FIG. 18 depicts a functional representation of the vias, where, as noted above, the numerals after the "15" correspond to the turns that are connected by the vias (e.g., via 1523 connects turn 2 to turn 3).

Accordingly, in an exemplary embodiment, there is an inductance communication coil, comprising a conductor, such as conductor 1574, including a first portion extending in a first level (e.g., turns 1, 2) and a second portion extending in a second level (e.g., turns 3, 4), wherein the conductor includes a third portion (e.g., turns 5 and 6) located on a different level than that of the second portion.

As will be understood from the structure of the present specification, the use of "first portion," "first turn," "second portion," "second turn," etc., are used for accounting purposes/for purposes of providing a distinguishing name. This does not connote order or primacy unless otherwise noted. This is as opposed to descriptor purposes (e.g., the turn that comes before others is the first turn—turn 1), and thus, for example, the first portion and the first turn does not necessarily correspond to turn 1, etc. Descriptor names (e.g., turn 1, turn 2, turn 3, etc.) are used as proper nouns herein when describing the exact turn.

Figure 17:
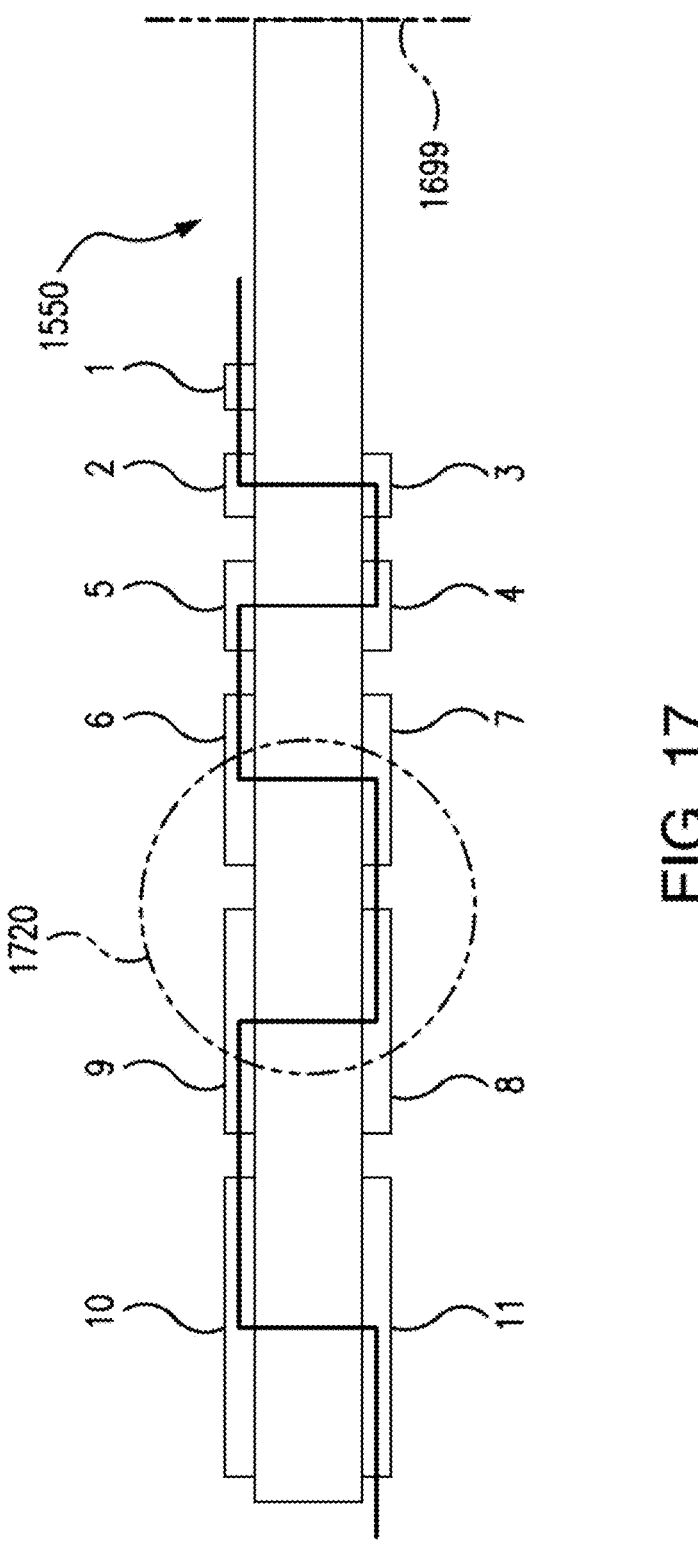
FIG. 17 depicts a detailed view of the exemplary cross-sectional view of FIG. 16.

In this exemplary embodiment, the electrical path of the conductor is such that the second portion is located between the first portion and the third portion. FIG. 17 depicts how this is the case with respect to path 1710. In an exemplary embodiment, the level on which the third portion is located is the first level, as seen in FIG. 16. In an exemplary embodiment, the first, second, and third portions are turns of the conductor (the first portion includes turn 1 and/or turn 2, the second portion includes turn 3 and/or turn 4, and the third portion includes turn 5 and/or turn 6). While the aforementioned embodiment includes a path where the electrical path extends through two turns on a first level and then extends to a second level and then extends through two turns and then extends to the first level, in an alternate embodiment, the electrical path extends through one turn on one level and then extends to a second level and then extends through another turn and then extends to the first level. Still further, a path of extension can have an extension through one turn on one level, two turns on another level and then one turn on the prior level, etc. Thus, in an exemplary embodiment, the second portion can include only one turn. It is noted that the terminology "portion" does not directly correspond to a turn. A portion can include two turns. That said, even in a scenario where a portion corresponds to one turn, with respect to the aforementioned embodiment where the second portion is located on a different level than the first portion and the third portion, there can be fourth portion corresponding to a fourth turn, wherein the fourth portion is located on the second level as well, and the electrical path of the conductor is such that the fourth portion is located between the first portion and the third portion.

In view of the figures, it is to be understood that in an exemplary embodiment, the first portion is a first turn (e.g., turn 2), the second portion is a second turn (e.g., turn 3), and the third portion is a third turn (e.g., turn 5), and the first turn is an inner turn relative to the third turn. Still further, the first turn (e.g., turn 2) and the third turn (e.g., turn 5) are on the same level.

It is further noted that in an alternate embodiment, there are more than two levels in which the conductor extends. In this regard, FIG. 19 conceptually depicts a cross-section of a PCB 1950 that includes a first substrate 1999 and a second substrate 1998, respectively supporting two different layers of conductors. (One or more substrates could be located between these substrates.) As can be seen, PCB 1950 includes turns 1 to 21. Electrical path 1910 extends from turn 1 in the first level to turn numeral 2. Then, electrical path 1910 extends from turn 2 through substrate 1999 to turn 3. After extending through turn 3 in the second layer, electrical path 1910 extends to turn 4 in the third layer. After extending through turn 4 in the third layer, electrical path 1910 extends through substrate 1998 to turn 5. (Here, the widths of turns 2, 3, 4 and 5 are the same or approximately the same (or at least the average width is the same), etc. After extending through turn 5 in the fourth layer, electrical path extends to turn 6 (which has a width that is wider than turn 5). After extending through turn 6 in the fourth layer, electrical path 1910 extends through substrate 1998 to turn 7, and so on, following path numeral 1910 until reaching turn 21, and then extending to the source or sink of the current.

Figure 19:
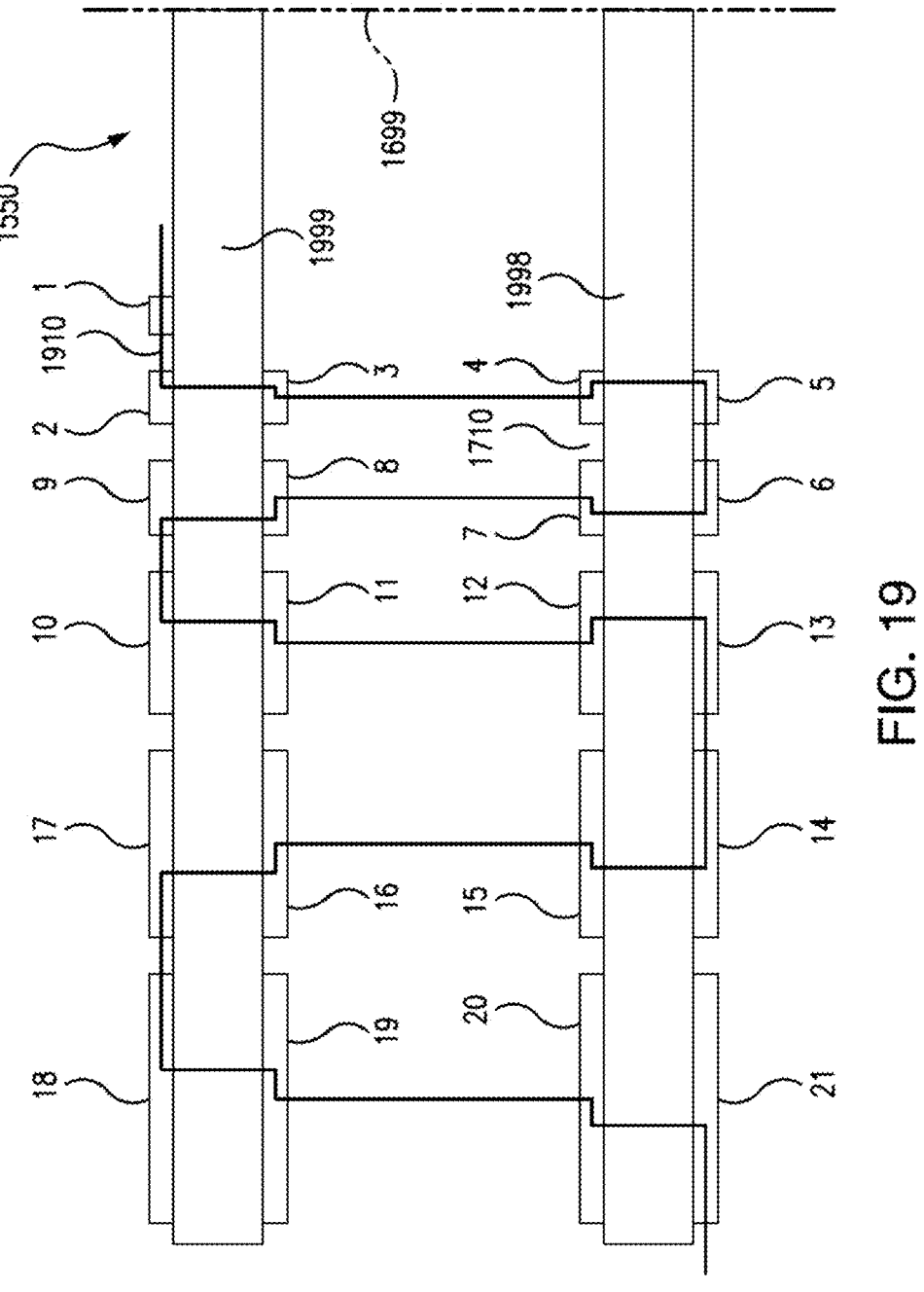
FIG. 19 depicts a detailed view of the exemplary cross-sectional view of another exemplary embodiment.

It is noted that in some alternate embodiments, the electrical path can extend in a different pattern (e.g., from level 1 to level 3 to level 2 to level 4; from level 1 to level 4 to level 2 to level 3; from level 2 to level 1 to level 3 to level 4; from level 4 to level 1 to level 3 to level 2, etc.). Note further that while the embodiment depicted in FIG. 19 depicts the path extending in a pattern that repeats itself (layer 1 to layer 2 to layer 3 to layer 4 to layer 3, to layer 2 to layer 1, etc.), in some alternate embodiments, the conductive path does not extend in a repeating pattern (it extends in a non-repeating pattern).

It is noted that in at least some exemplary embodiments, the electrical path of the turns/tracks extend in only two different levels and no more than two different levels.

In view of the above, it is noted that the widths of turns 2, 3, 4 and 5 are the same or approximately the same (or the average widths are the same or approximately the same), the widths of turns 6-9 are the same or approximately the same (or the average widths are the same or approximately the same), but wider than the turns of 2-5, the widths of turns 10-13 are the same or approximately the same (or the average widths are the same or approximately the same), but wider than the turns of 6-9, the widths of turns 14-17 are the same or approximately the same (or the average widths are the same or approximately the same), but wider than the turns of 10-13, the widths of turns 18-21 are the same or approximately the same (or the average widths are the same or approximately the same), but wider than the turns of 14-17. That said, in an alternate embodiment, the widths of turns 2, 3, 4 and 5 are the same or approximately the same (or the average widths are the same or approximately the same), the widths of turns 6-9 are the same or approximately the same (or the average widths are the same or approximately the same), but wider than the turns of 2-5, the widths of turns 10-13 are the same or approximately the same (or the average widths are the same or approximately the same), but wider than the turns of 6-9, the widths of turns 14-17 are the same or approximately the same (or the average widths are the same or approximately the same), but narrower than the turns of 10-13, the widths of turns 18-21 are the same or approximately the same (or the average widths are the same or approximately the same), but narrower than the turns of 14-17.

Still further, it is noted that in an exemplary embodiment, the widths of turns 2, 3, 4 and 5 can be different from one another (one or more), or the average widths are different from one another, the widths of turns 6-9 are different from one another (one or more) or the average widths are different from one another, but are wider than the turns of 2-5, etc.

Thus, in an exemplary embodiment, with respect to the aforementioned embodiment having a conductor having a first portion, a second portion, and a third portion, where the respective portions are located on different levels, the level on which the third portion is located is a level different from the first level and the second level, where the first portion is located on the first level and the second portion is located on the second level. In more basic terms, there is a substrate (e.g., substrate 1652) that has a first side and a second side (e.g., with respect to FIG. 16, the top side of substrate 1652 and the bottom side of substrate 1652), where the substrate supports a conductor that includes a first turn on a first side (e.g., turn 2 on the top side) and a second turn on a second side (e.g., turn 3 on the bottom side), where the conductor extends into the substrate after completing one or more turns. Still further, in an exemplary embodiment, the conductor can include a third turn (e.g., turn 5 on the top side). In an exemplary embodiment, an "alternation cycle" of the exemplary conductor extends from the first turn through the second turn to the third turn, as seen in FIG. 17, where the alternation cycle takes the conductive path from one the first level to another level and then back to the first level (there might be additional levels between the first level and returning back to the first level. Note further that the alternation cycle of the cycled conductor can extend from the first turn (turn 2) through the second turn (turn 3) and fourth turn (e.g., turn 4) to the third turn (turn 5). Because the conductor alternates in a cyclic manner into the substrate 1652 via a plurality of alternation cycles, the conductor can be considered to be weaved/woven into the substrate 1652. In an exemplary embodiment, the conductor alternatingly cycles through the substrate for more than one complete cycle. By way of example only and not by way of limitation, the conductor can extend on the first level, and then to the second level, and then extend back up to the first level and then extend to the second level, thus representing basically one and a half cycles, and thus more than one complete cycle.

As can be seen from FIGS. 15-19, the turns of the conductor are aligned with one another in the vertical direction (i.e., with location along axis 1699). Thus, in an exemplary embodiment, the aforementioned first, second, and third portions of the conductor are turns of the conductor, and the first, second, and third portions (or additional portions (turns)) are aligned with each other about an axis of rotation (axis 1699) over at least about 300 degrees of subtended angle of the turns. In an exemplary embodiment, the various portions are aligned with each other over at least about 310, 320, 330, 340, 350, or 360 degrees or any value or range of values therebetween in 1° increments (e.g., about 12°, about 347°, about 303 degrees to about 355°, etc.).

It is further noted that some exemplary embodiments can be considered to utilize a conductor that is cycled into a substrate. By way of example, with reference to FIG. 17, the portion of the conductive path 1710 located within the circle 1720 is an alternation cycle in that the path goes down into the substrate, extends a distance along the second level, and then extends up into the substrate. That said, an alternation cycle can also correspond to a portion of the path that goes up into the substrate, extends along the first level, and then extend down into the substrate.

Again with respect to FIG. 18, vias are utilized to place a portion of the conductor located on one level into electrical communication with a portion of the conductor located on another level. In this regard, a given alternation cycle can include two vias that extend through the substrate. In an exemplary embodiment, each of the vias of a given alternation cycle connect a turn on one side of the substrate with a turn on another side of the substrate.

At least some embodiments are configured such that the resulting inductance coil has a Q factor that has utilitarian value. In an exemplary embodiment, there is an inductance communication coil, comprising a coiled conductor including at least two turns on a first layer and at least two turns on a second layer different from the first layer. In an exemplary embodiment, the number of turns on the first layer correspond to 2, 3, 4, 5, 6, 7, 8, 9, or 10 turns or more. In an exemplary embodiment, the number of turns on the second layer corresponds to 2, 3, 4, 5, 6, 7, 8, 9, or 10 turns or more (the same number of turns can be on both (or all) layers or the number of turns can be different on one or more layers). A maximum outer diameter of the outermost turn (turns 10 and 11 in the exemplary embodiments of FIGS. 15-18) of the given turn (or any of the aforementioned number of turns) is about 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, or about 40 mm, or any value or range of values therebetween in about 0.1 mm increments. Further, the coiled conductor is of a configuration where a bare winding thereof, when subjected to an electrical current having a frequency of about 5 MHz, having one of the aforementioned number of turns within one of the aforementioned diameters, has a Q factor of one of at least 70, at least 71, at least 72, at least 73, at least 74, at least 75, at least 76, at least 77, at least 78, at least 79, or at least 80 or more.

By "bare winding," it is meant that all other components of the inductance communication component are not present, such as the magnet, EMI shielding, etc. Such can be determined by way of example and not by way of limitation, by computer models, stimulations, or by holding the windings in space using materials that effectively do not impact the Q value.

It is noted that in at least some exemplary embodiments, the teachings detailed herein can have utilitarian value with respect to reducing electromagnetic interference (EMI) resulting from the use of the inductance coil. In some embodiments, because the "higher numbered" turns are kept away from the "lower numbered" turns, as opposed to implementations where the turns progress from the inside (outside) sequentially on one side, and then progress from the outside (or inside) on the other side (i.e., no weave, such as the arrangement used to generate the data of FIG. 22 detailed below), parasitic capacitance and/or electric field strength that would exist, all other things being equal (width, thickness length of conductor, distance between tiers, material, current source and frequency, substrate makeup, same EMI shielding, same proximity to other components (e.g., the BTE), etc.) is reduced relative to that which is the case in the implementations where the higher numbered turns are not kept away from the lower numbered turns. In an exemplary embodiment, the overall reduction (i.e., for the entire inductance coil) is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more.

Indeed, in an exemplary embodiment, there is an inductance coil where the Q value is at least more than about 1%, 2%, 3%, 4%, 5%, 6%, 7%, 8%, 9%, 10%, 11%, 12%, 13%, 14%, 15%, 16%, 17%, 18%, 19%, 20%, or more than that which would exist, all other things being equal (width, thickness length of conductor, distance between tiers, material, current source and frequency, substrate makeup, same EMI shielding, same proximity to other components (e.g., the BTE), etc.) relative to that which is the case in the implementations where the higher numbered turns are not kept away from the lower numbered turns (i.e., no weave). That is, if the only difference was the presence of the weave, the above differences would be present.

With reference back to FIG. 5B, as can be seen, in an exemplary embodiment, a given turn of the inductance coil 574B subtends an angle of about 360° or so about the same inner and/or outer radius before increasing to a new and or and or outer radius. That is, the "track" of the turn is the same for about 360°, until changing to a new track, which is outside the inner track. In this regard, as a conceptual manner, the aforementioned inner and/or outer radii are quasi-independent of the width. Alternatively, in an exemplary embodiment, this feature can be described as a centerline of the conductor has a constant radius over an angle of about 360°, and then the centerline changes to another radius, a larger radius, and that centerline extends over an angle of about 360° until the centerline changes again to have another radius, a larger radius, etc. In an exemplary embodiment, the angle subtended by the portion of the conductor on the same track and/or having the same inner radius and/or outer radius and/or centerline is at least or equal to 200, 210, 220, 230, 240, 250, 260, 270, 280, 290, 300, 310, 320, 330, 340, 350, or even 360 of these or any value or range of values therebetween in 1 degree increment. As can be seen in the figures, in an exemplary embodiment, there is at least one, two, three, or four or more discrete occurrences of such (where by discrete occurrences, the angles do not overlap). In an exemplary embodiment, there is at least 1, 2, 3, 4, 5, 6, 7, 8, 9, 10, 11, 12, 13, 14, 15 or more discrete occurrences of such.

In a similar vein, this feature is also the case with respect to the embodiment of FIG. 5A, where, as can be seen, in an exemplary embodiment, a portion of the inductance coil 574A subtends an angle of about 300 degrees or so (note that this is for conceptual purposes—the drawings do not reflect all embodiments/are not exact with respect to all embodiments) before being fully outside of the outer radius of the turn precedent (inner thereto) with respect to the location where the beginning of that angle is measured. In this regard, as can be seen in FIG. 5A, the inner radius of the turn (e.g., turn 1) grows larger with respect to location on the turn relative to the beginning of the turn. At some point, the inner radius is larger than the outer radius at the beginning of the turn (e.g., the portion of the turn having the smallest outer radius). In FIG. 5A, in an exemplary embodiment, the angle is about 300° at this point. That is, prior to reaching about 300°, the inner radius is smaller than the outer radius as that value exists at the beginning point. In an exemplary embodiment, this angle can be at least or equal to 190, 200, 210, 220, 230, 240, 250, 260, 270, 280, 290, 300, 310, 320, 330, 340, 350, or even 360 of these or any value or range of values therebetween in 1 degree increment. It is also noted that the aforementioned features can be described in terms of the centerline of the conductor. In this regard, in an exemplary embodiment, the centerline subtends an angle of any of the aforementioned values where the radius of the centerline minus the local width is less than or equal to the radius of the centerline at the beginning of the angle. As can be seen in the figures, in an exemplary embodiment, there is at least two, three, or four or more discrete occurrences of such (where by discrete occurrences, the angles do not overlap). In an exemplary embodiment, there is at least 2, 3, 4, 5, 6, 7, 8, 9, 10, 11, 12, 13, 14, 15 or more discrete occurrences of such.

It is also noted that in at least some exemplary embodiments where the aforementioned relationships described in the above two paragraphs occur, such occurs in a staggered fashion, such that an occurrence with respect to a first radius (measured from either the inner or the outer or the centerline of the conductor) and an occurrence with respect to a second radius and then an occurrence with respect to a third radius, where the first radius is the smallest radius, the third radius is the largest radius, and the second radius is in between the two radii, occurs such that with respect to the path of the electrical circuit established by the conductor, the path extends through the occurrence related to the first radius, and then through the occurrence related to the second radius and then through the occurrence related to the third radius. This is also the case with respect to an occurrence with respect to a fourth radius a fifth radius a sixth radius etc. where each radius is larger than the preceding radius.

By way of example only and not by way of limitation, in an exemplary embodiment, other than with respect to the ends (or beginnings), the conductor is such that a given radius of the conductor (inner, centerline, outer) is at least one of constant, or increasing over an angle equal to or greater than 200, 210, 220, 230, 240, 250, 260, 270, 280, 290, 300, 310, 320, 330, 340, 350, or even 360. That is, in an exemplary embodiment, the given radius never decreases (with respect to one direction of an electrical path—with respect to another path (the opposite path), the radius is always decreasing or remains constant (other than in some embodiments at the beginning and the end)).

It is also noted that in at least some exemplary embodiments, the aforementioned detailed features of the preceding four paragraphs are the case with respect to the path of the conductor on a first level (the same level), while in other embodiments the aforementioned detailed features are the case with respect to portions of the conductor that are on a first level and portions of the conductor that are on a second level. By way of example only and not by way of limitation, in an exemplary embodiment, where for a conductor that has a given radius meeting one or more of the aforementioned features, where the angle subtended is at least 300 degrees, in an exemplary embodiment, a portion of those 300° can be located on a first level and a portion of those 300° can be located on a second level. It is also noted that in an exemplary embodiment, the aforementioned occurrences of the preceding four paragraphs can be varied such that there is one discontinuity over the path of the conductor subtended by the given angle. This discontinuity can be related to the end of the conductor path on the first level in the beginning of the conductor path on the second level and the via that connects the two levels at that local location. Accordingly, in an exemplary embodiment, the aforementioned occurrences can exist, but with the caveat that there is a sub-angle of no more than 1, 2, 3, 4, 5, 6, 7, 8, 9, 10, 12.5, 15, 17.5, 20, 25 or 30 or 35 or 40 degrees or any value or range of values therebetween in 1° increments where the aforementioned occurrence does not exist.

It is also noted that in at least some exemplary embodiments of the teachings detailed herein (e.g., with respect to the conductor is having different widths), in an exemplary embodiment, other than the beginning and end of the conductive path, the path does not cross itself on a given level. Still further, in an exemplary embodiment (e.g., with respect to the conductor having different widths), in an exemplary embodiment, other than the beginning and end of the conductive path, when the path does cross itself, it crosses itself only where the path subtends an angle of at least about 10, 15, 20, 25, 30, 35, 40, 45, 50, 55 or 60 degrees or more or any value or range of values therebetween in 1° increments at another level and remains on that level over the subtended angle. Still further, in an exemplary embodiment, in an exemplary embodiment, other than the beginning and end of the conductive path, when the path does cross itself, it crosses itself only where the path is located on an opposite side of the substrate (as opposed to the middle of the substrate). That is, in an exemplary embodiment, any locations where the paths cross each other (looking downward on the plane of the conductor (e.g., the plane of FIG. 15) are such that the "crossings" occur on opposite sides of the substrate.

It is also noted that in at least some exemplary embodiments where paths cross each other, or at least otherwise overlap, again, with respect to looking downward on the plane of the conductor, the overlap of the portions of the conductor (partial or total overlap) subtends an angle greater than at least about 10, 15, 20, 25, 30, 35, 40, 45, 50, 55 or 60 degrees or more or any value or range of values therebetween in 1° increments.

FIG. 20 presents an exemplary flowchart 10000 for an exemplary method according to an exemplary embodiment. Method 10000 includes method action 10010, which entails transcutaneously transmitting, using a first coiled inductance antenna (e.g., external coil 130 of FIG. 1A, corresponding to an embodiment detailed herein or a variation thereof) located outside the skin of the recipient (e.g., located above a mastoid bone of the recipient), an inductance signal to an implanted second coiled inductance antenna (e.g., located above the mastoid bone of the recipient). This can be executed with any of the inductance coils detailed herein or variations thereof. Method 10000 further includes method action 10020, which entails at least one of recharging an implanted battery or powering an implanted functional component based on a signal from the second coiled inductance antenna, the second signal being generated by the inductance signal. In an exemplary embodiment, this implanted battery is the implanted battery noted above with respect to the implanted component 100 of system 10 detailed above. In an exemplary embodiment, the functional component could be a receiver stimulator of the implanted component 100. The functional component could be any implanted component that requires power to function. It is noted that in an exemplary embodiment, method actions 10010 and 10020 can be executed automatically.

In this exemplary embodiment, the first coiled inductance antenna includes a first tier containing conductive turns and a second tier containing conductive turns located above the first tier, such as by way of example only and not by way limitation, that which results from implementing the embodiment of FIG. 15 detailed above. Still further, any electric field located at any location directly between the first tier and the second tier at the middle distance between the first tier and the second tier has a value of no more than about $4 \times 10^5$ V/m, when the coil is energized at about 1 amp, at a frequency of about 5 MHz, having, dimensions corresponding to those detailed herein.

By "directly between" it is meant that the location is within the footprint of the turns (e.g., location L161 in FIG. 16 as opposed to L162). By "the middle distance between the first tier and the second tier," it is meant that the location is half way between the two tiers (L161 as opposed to L163, again with reference to FIG. 16). That said, in an alternate embodiment, any electric field located at any location directly between the first tier and the second tier within a range of about 50% of the distance from one of the turns on the first tier to another of the turns on the second tier centered on either side of the middle location (i.e., $\frac{1}{4}^{th}$ the total distance between the two tiers (closest facing surfaces of the turns) on either side of the middle location), with the above-noted control variables (amperage, frequency, dimensions, etc.) has a value of no more than about $4 \times 10^5$ V/m. That said, in an alternate embodiment, any electric field located at any location directly between the first tier and the second tier within a range of about 60% of the distance from one of the turns on the first tier to another of the turns on the second tier centered on either side of the middle location (i.e., 30% the total distance between the two tiers (closest facing surfaces of the turns) on either side of the middle location) with the above-noted control variables (amperage, frequency, dimensions, etc.) has a value of no more than about $4 \times 10^5$ V/m. That said, in an alternate embodiment, any electric field located at any location directly between the first tier and the second tier within a range of about 70% of the distance from one of the turns on the first tier to another of the turns centered on the second tier on either side of the middle location (i.e., 35% the total distance between the two tiers (closest facing surfaces of the turns) on either side of the middle location) with the above-noted control variables (amperage, frequency, dimensions, etc.) has a value of no more than about $4 \times 10^5$ V/m. That said, in an alternate embodiment, any electric field located at any location directly between the first tier and the second tier within a range of about 80% of the distance from one of the turns centered on the first tier to another of the turns on the second tier on either side of the middle location (i.e., 40% the total distance between the two tiers (closest facing surfaces of the turns) on either side of the middle location) with the above-noted control variables (amperage, frequency, dimensions, etc.) has a value of no more than about $4 \times 10^5$ V/m. That said, in an alternate embodiment, any electric field located at any location directly between the first tier and the second tier within a range of about 40% of the distance from one of the turns on the first tier to another of the turns on the second tier centered on either side of the middle location (i.e., 20% the total distance between the two tiers (closest facing surfaces of the turns) on either side of the middle location) with the above-noted control variables (amperage, frequency, dimensions, etc.) has a value of no more than about $4 \times 10^5$ V/m.

It is noted that the aforementioned features are the case for all of the locations directly between the turns (i.e., every turn, not just some of the turns). It is further noted that the aforementioned electric field values can be instead no more than about 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or $1.0 \times 10^5$ V/m or even lower (e.g., see FIG. 21A) with the above-noted control variables (amperage, frequency, dimensions, etc.).

Briefly, it is noted that in an exemplary embodiment, the distance 169 from one turn to the other/closest turns (with respect to different turns in different tiers, as opposed to different turns on the same tier) is about 0.35 mm/no greater than about 0.35 mm. In an exemplary embodiment, 169 is about/no greater than about 0.15 mm, 0.16 mm, 0.17 mm, 0.18 mm, 0.19 mm, 0.2 mm, 0.21 mm, 0.22 mm, 0.23 mm, 0.24 mm, 0.25 mm, 0.26 mm, 0.27 mm, 0.28 mm, 0.29 mm, 0.3 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.51 mm, 0.52 mm, 0.53 mm, 0.54 mm, 0.55 mm, 0.56 mm, 0.57 mm, 0.58 mm, 0.59 mm, 0.60 mm, 0.61 mm, 0.62 mm, 0.63 mm, 0.64 mm or 0.65 mm or more or less or any value or range of values therebetween in about 0.001 mm increments. Thus, in an exemplary embodiment, the minimum distance between turns of the first tier and turns of the second tier is no greater than about 0.6 mm.

Figure 21A:
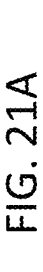
FIG. 21A depicts an exemplary graph presenting data according to an exemplary embodiment.

FIG. 21A depicts an exemplary electric field plot depicting the electric field in V/m (values on bar on the right are given in values of $\times 10^5$, starting from 0 to 5 in 0.5 increments) for locations between the two tiers of turns (and other areas as well), where the values on the left are given in values of $\times 10^{-3}$ m (in $0.2 \times 10^{-3}$ m increments). It is noted that while the plot of FIG. 21A is presented for turns having the same width, the general data is applicable for turns having different widths, providing that the turns have the weave feature as detailed herein. (The data might need to be scaled, although in other embodiments, this data may be directly applicable to the varying width embodiment.) In this regard, the resulting electric fields can be lower than that depicted, in some embodiments, using the varying width, while in other embodiments, the resulting electric fields can be the same as (or approximately the same as), that presented in FIG. 21A.

Figure 21B:
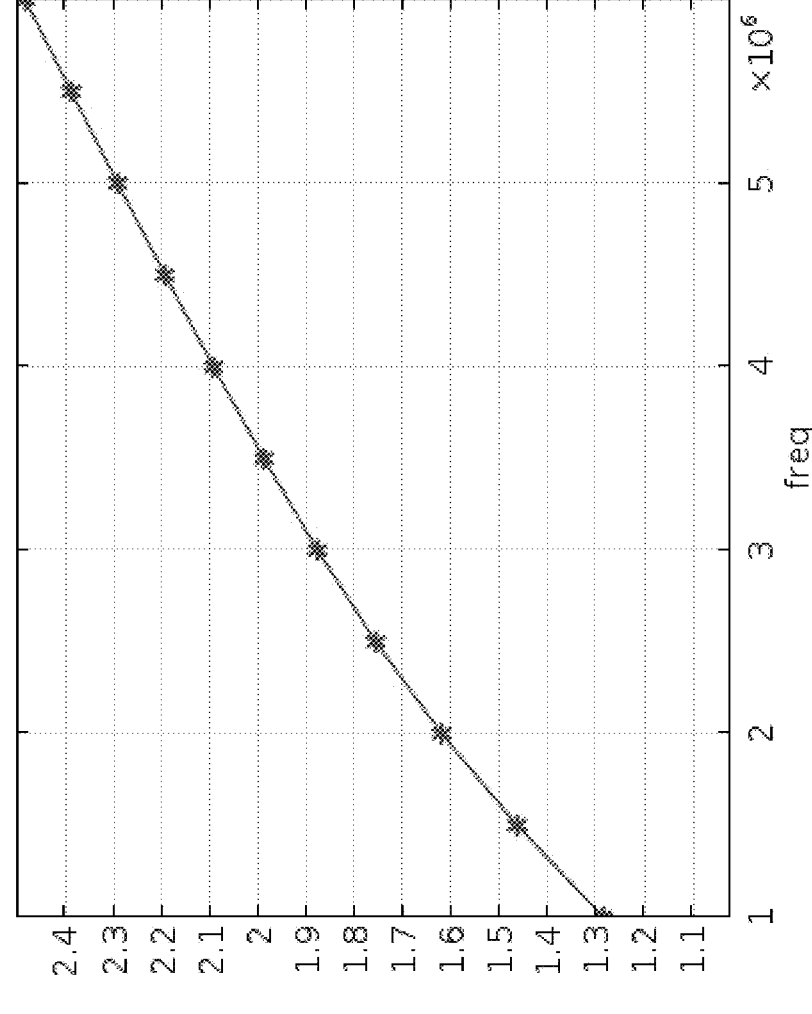
FIG. 21B depicts an exemplary graph presenting data according to an exemplary embodiment associated with FIG. 21A.

The Y axis details distance in meters from the center (middle distance) of the two tiers, and the X axis details distance in meters from the center of rotation (e.g., axis 1699) of the turns. In this exemplary embodiment, the current applied to the exemplary inductance coil was at a frequency of 5.0 MHz. Again, the details of FIG. 21A can be adjusted to account for the varying width pattern (e.g., turns 2 and 5 might be closer to center of rotation, owing to the fact that they will be narrower than that shown, thus accommodating for the wider turns 6, 8 and 11, etc.). Moreover, FIG. 21B depicts an exemplary graph of coil voltage vs. frequency for an exemplary embodiment associated with the plot of FIG. 21A. In an exemplary embodiment, the values present in FIG. 21A are scaled to the data presented in FIG.

21B, where the data for FIG. 21A was developed for the resulting coil voltage at a frequency of 5 MHz (2.3V).

In an exemplary embodiment, the coiled inductance antenna having the aforementioned electric field values is of a configuration where a bare winding thereof, when subjected to an electrical current having a frequency of 5 MHz, has a Q factor of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80. Indeed, it is noted that in at least some exemplary embodiments, the aforementioned electric field values are for a bare winding having the control variables detailed herein.

With respect to the graph of FIG. 21A, the highest value obtained at the aforementioned control values was $6.74 \times 10^5$ V/m, and the lowest value was 4.74 V/m.

Figure 22A:
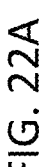
FIG. 22A depicts an exemplary graph presenting data according to an exemplary embodiment.
Figure 22B:
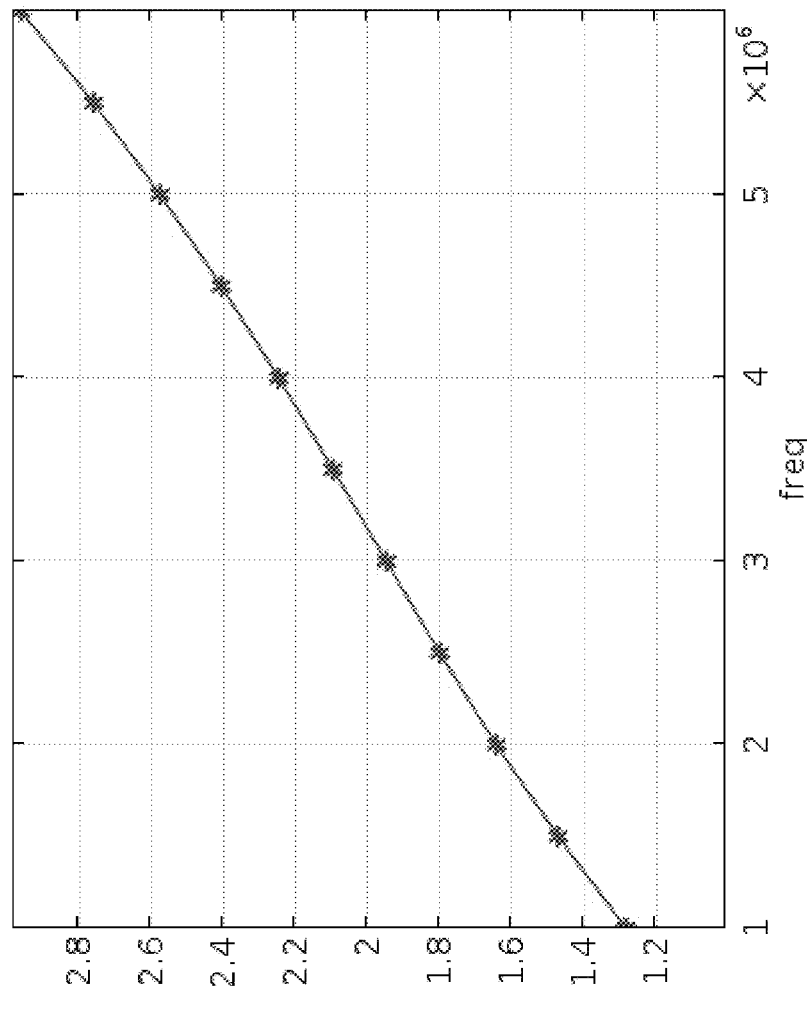
FIG. 22B depicts an exemplary graph presenting data according to an exemplary embodiment associated with FIG. 22A.

FIG. 22A depicts an electric field resulting from an inductance coil that utilizes a configuration where the conductor is such that an electrical path extends through turns outwardly (or inwardly) on one layer/tier, and then extends inwardly (or outwardly) on another layer/tier (as opposed to having the weave/cycling configuration) for the exact same application of current to the conductor as that resulting in the field of FIG. 21A. Again, as with FIG. 21A, while this data is presented in terms of uniform width turns, this concept can be applicable to varying widths as well, and the data can be scaled (if necessary or otherwise utilitarian) accordingly. That is, other than the fact that the inductance coil of FIG. 22A does not utilize the weave/cycling of the inductance coil of FIG. 21A, the inductance coil of FIG. 22A is the same and used in the same way. As can be seen, the embodiment utilizing the weave (FIG. 21A) is different than the embodiment of FIG. 22A, all other things being equal. With respect to the graph of FIG. 22A, the highest value obtained at the aforementioned control values was $2.67 \times 10^6$ V/m, and the lowest value was 3.79 V/m. Thus, the differences between the highest values of the field strengths for the two different coils represented by FIGS. 21A and 22A, all other things being equal, was almost an order of magnitude different. Moreover, FIG. 22B depicts an exemplary graph of coil voltage vs. frequency for an exemplary embodiment associated with the plot of FIG. 21A. In an exemplary embodiment, the values present in FIG. 22A are scaled to the data presented in FIG. 22B, where the data for FIG. 22A was developed for the resulting coil voltage at a frequency of 5 MHz (2.57V). (It is noted that while the dielectric properties of the materials around the turns (substrate, air, etc.) affect the electric field level, because the differences between FIGS. 21A and 22A are limited to those detailed above (e.g., these features are the same for both coils), these do not impact the results.)

FIG. 23 depicts an exemplary flowchart 13000 for an exemplary method according to an exemplary embodiment. Method 13000 includes method action 13010, which entails capturing an ambient sound with a microphone. In an exemplary embodiment, this method action is executed using the cochlear implant system 10 detailed above, where the microphone is either implanted in the recipient or is external to the recipient (e.g., the totally implantable hearing prosthesis is utilizing an external microphone). Method 13000 further includes method action 13020, which entails converting the captured ambient sound to a first signal. In at least some exemplary embodiments, this first signal corresponds to the output of the aforementioned microphone.

Method 13000 also includes method action 1330, which entails transcutaneously transmitting, using a first coiled inductance antenna located outside the skin of the recipient, such as over a mastoid bone of the recipient (e.g., external coil 130 of FIG. 1A, corresponding to an embodiment detailed herein or a variation thereof) an inductance signal based on the first signal to an implanted second coiled inductance antenna. Thereafter, method action 13040 is executed, which entails evoking a hearing percept based on a signal from the second coiled inductance antenna, the second signal being generated by the inductance signal. It is noted that in an exemplary embodiment, method actions 13010, 13020, 13030 and 13040 can be executed automatically.

In this exemplary embodiment, the first coiled inductance antenna includes a first tier containing conductive turns and a second tier containing conductive turns located above the first tier, such as by way of example only and not by way of limitation, that which results from implementing the embodiment of FIG. 15 detailed above. Still further, any electric field located at any location directly between the first tier and the second tier at the middle distance between the first tier and the second tier (or any of the other locations detailed above) has a value of no more than about $4 \times 10^5$ V/m (or no more than any of the other values noted above.

It is noted that in an exemplary embodiment, method 10000 can be executed using the same system 10 as that used to execute method 13000. Indeed, method 10000 can be executed after method 13000, and method 13000 can be executed after method 10000.

It is further noted that in an exemplary embodiment, there is an inductance communication coil, such as a coil configured to transcutaneously communicate with an implanted inductance communication coil that is in signal communication with a stimulator unit of an implantable medical device, where the implanted inductance coil is located above the mastoid bone of the recipient, having a coiled conductor including at least three turns on a first layer, wherein a maximum outer diameter of the outermost turn of the at least three turns is about 30 mm, and the coiled conductor is of a configuration where a bare winding thereof, when subjected to an electrical current having a frequency of about 5 MHz, at about 1 amp, has a resulting magnetic field corresponding to any of those detailed herein. In this regard, in an exemplary embodiment, the inductance communication coil has any one of the configurations (e.g., dimensions) detailed herein. In an exemplary embodiment, the coil has at least 4 turns, at least 5 turns, at least 6 turns, at least 7 turns, at least 8 turns, at least 9 turns or at least 10 turns within any of the aforementioned diameters detailed herein, on one or both sides of a given substrate.

In view of the above, in an exemplary embodiment, there is a method, comprising transcutaneously transmitting, using a first coiled inductance antenna located above a mastoid bone of the recipient, an inductance signal to an implanted second coiled inductance antenna, and at least one of recharging an implanted battery or powering an implanted functional component based on a second signal from the second coiled inductance antenna, the second signal being generated by the inductance signal, wherein the first coiled inductance antenna includes a first tier containing conductive turns and a second tier containing conductive turns located above the first tier, and any electric field located at any location between the first tier and the second tier at the middle distance between the first tier and the second tier has a value of no more than about $4 \times 10^5$ V/m. In an exemplary embodiment of this method, the minimum distance between turns of the first tier and turns of the second tier is no greater than about 0.5 mm. In an exemplary embodiment of this method, the coiled inductance antenna is of a configuration where a bare winding thereof, when subjected to an electrical current having a frequency of about 5 MHz, has a Q factor of at least 60. In an exemplary embodiment of this method, a distance between turns of the first tier and turns of the second tier is no greater than about 0.4 mm. In an exemplary embodiment of this method, a distance between turns of the first tier and turns of the second tier is no greater than about 0.35 mm. In an exemplary embodiment of this method, any electric field located at any location between the first tier and the second tier at the middle distance between the first tier and the second tier has a value of no more than about $3\times10^5$ V/m. In an exemplary embodiment of this method, any electric field located at any location between the first tier and the second tier at the middle distance between the first tier and the second tier has a value of no more than about $2\times10^5$ V/m. Still further, in an exemplary embodiment of this method, any electric field located at any location between the first tier and the second tier at the middle distance between the first tier and the second tier has a value of no more than about $1.5\times10^5$ V/m.

In an exemplary embodiment, there is a communication coil, comprising a first layer including a first plurality of conductive turns, and a second layer including a second plurality of conductive turns separated from the turns of the first layer by a distance, wherein a portion of a conductive path extends through the first plurality of conductive turns and the second plurality of conductive turns, the portion of the conductive path beginning at an outside of a turn of the first plurality of conductive turns or the second plurality of conductive turns and ending at an inside turn of the first plurality of conductive turns or the second plurality of conductive turns.

While the above has been presented most often in terms of a communication coil in general, and an inductance communication coil in particular, embodiments include a coil that is utilized in data transfer/communication and power transfer/communication systems and/or in electronic components. In an exemplary embodiment, wireless power transfer systems can utilize one or more or all of the teachings detailed herein. Accordingly, any disclosure of a coil detailed herein and/or features associated therewith corresponds to a disclosure of power transfer system utilizing such coil and/or having such features. Note further that in some embodiments, power transfer capabilities and data communication capability is combined in one system. In an exemplary embodiment, the coil is used for both. (Note that the term communication can encompass both data and power communication.) In an exemplary embodiment, the teachings detailed herein can be utilized to transfer power over relatively larger distances than that which would be the case with other, pre-existing technologies. By way of example only and not by way limitation, in an exemplary embodiment, owing to the relatively high Q values which can be achieved by at least some exemplary embodiments of the teachings detailed herein, this can enable power to be transferred over larger distances relative to that which would be the case utilizing technologies that do not provide the Q values as can be achieved with the teachings detailed herein. By way of example only and not by way of limitation, all other things being equal, a given amount of energy transfer in a given unit time a distance that is at least about 20%, 30%, 40%, 50%, 60%, 70%, 80%, 90% or 100% or more greater than the distance of transfer for a coil not using one or more of the teachings detailed herein, all other things being equal.

By way of example only and not by way of limitation, the teachings detailed herein can be utilized with the REZENCE™ power transfer system (e.g., systems utilizing the REZENCE™ standard for power transfer) and/or the QI™ power transfer system (e.g., systems utilizing the QI™ standard for power transfer). Still further, in an exemplary embodiment, the teachings detailed herein can be utilized to alleviate the deleterious effects associated with relatively poorly aligned coils when such coils are utilized for power transfer. In this regard, in an exemplary embodiment, because of the relatively high Q values that can be obtained, power transfer can be executed utilizing coils that are misaligned more than that which would otherwise might be the case for a given amount of power transfer within a given period of time. In an exemplary embodiment, the amount of misalignment that can be incurred while achieving the same amount of energy transfer within a given unit time, all other things being equal, with respect to existing coils not utilizing the teachings detailed herein, can be greater (again all of the things being equal).

Still further, it is noted that in an exemplary embodiment, repeaters, including passive repeaters, can be utilized in power transfer systems utilizing some or all of the teachings detailed herein. Thus, embodiments include power transfer systems that utilize passive repeaters (or other types of repeaters) including one or more of the teachings detailed herein.

At least some exemplary embodiments of the teachings detailed herein can be utilized in RF (Radio Frequency) circuits, including but not limited to those that are semiconductor-based and/or chip based. By way of example only and not by way of limitation, in at least some exemplary embodiments, there are silicon chips that utilize some or all of the teachings detailed herein, and in some embodiments, these chips are utilized as RF circuits. Such exemplary embodiments can include RF circuits that are utilized for high frequencies (e.g., above 1 GHz, 1.5 GHz, 2 GHz, 2.4 GHz, 3 GHz, etc.). Note further, in at least some exemplary embodiments, chip inductors can incorporate the teachings detailed herein and/or variations thereof.

In some exemplary embodiments, the teachings detailed herein and/or variations thereof can be utilized with respect to wirelessly charging consumer handheld products, such as cell phones, smart phones, etc. In some exemplary embodiments, the teachings detailed herein and/or variations thereof can utilize with respect to wirelessly charging devices such as laptop computers, portable entertainment systems (e.g., dedicated gaming devices, etc.), large pads (e.g., pads with 7×12 inch screens), etc. Still further, in some exemplary embodiments, the teachings detailed herein and/or variations thereof can be applied to wirelessly charging large devices such as, by way of example only and not by way limitation, electric vehicles, unmanned aerial vehicles, robots, etc. Any application of the teachings detailed herein that can have utilitarian value can be practiced in some embodiments.

It is further noted that in at least some exemplary embodiments, the teachings detailed herein can be utilized for RFID systems.

Corollary to the above is that the teachings detailed herein and/or variations thereof can be applicable to technologies outside of the medical device arena. In at least some exemplary embodiments, the teachings detailed herein and/or variations thereof can be utilized in technology that utilizes magnetic induction and/or magnetic resonance (at least those areas of these technologies that utilize a coil). Still further, some embodiments include inductors and/or transformers that utilize the teachings detailed herein. In an exemplary embodiment, some inductors and/or transformers are constructed utilizing PCB traces and planar cores that go through the PCB. In an exemplary embodiment, the traces and/or other components of these inductors and/or transformers are constructed according to the teachings detailed herein, at least in part. In at least some exemplary embodiments, such constructions result in lower resistances of the windings relative to that which would be the case without utilizing the teachings detailed herein, all other things being equal. In an exemplary embodiment, the overall resistance of the system is reduced by more than 1%, 2%, 3%, 4%, 5%, 7%, 10%, 12%, 15%, 20%, 25%, 30%, 35%, 40%, 45%, 50%, 60%, 65%, 70% or more or any value or range of values therebetween in 0.1% increments.

Figure 24:
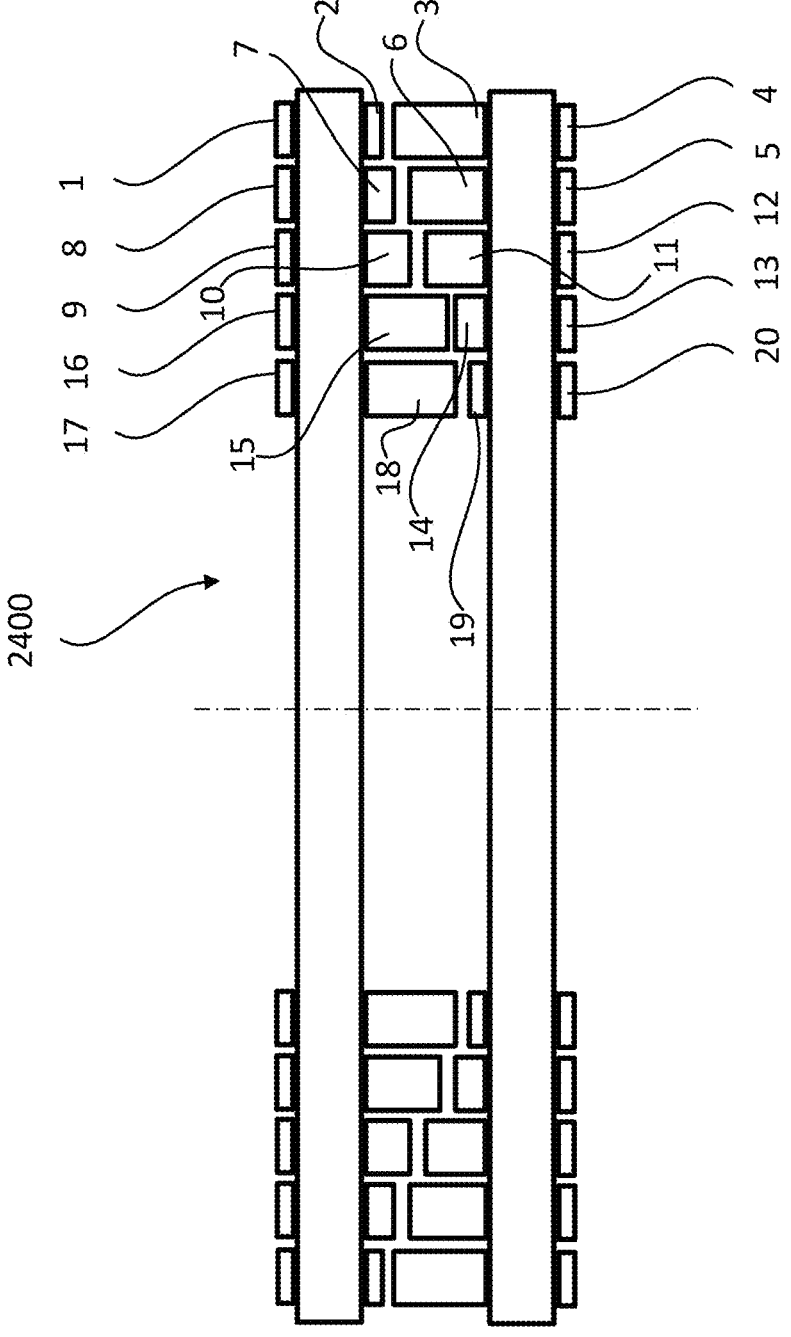
FIG. 24 depicts a detailed view of the exemplary cross-sectional view of another exemplary embodiment.

FIG. 24 depicts an alternate embodiment of a coil assembly, including two levels in which the conductor extends. In this regard, FIG. 24 conceptually depicts a cross-section of a PCB 2400 that includes a first substrate and a second substrate, respectively supporting two different layers of conductors. (One or more substrates could be located between these substrates.) As can be seen, PCB 2400 includes turns 1 to 20. The electrical path (not shown) extends from turn 1 in the first level to turn numeral 2 in the second layer (through the substrate supporting those turns). Then, the electrical path extends from turn 2 to turn 3. After extending through turn 3, the electrical extends to turn 4 in the fourth. (Here, the widths of turns 1-20 are the same or approximately the same (or at least the average width is the same, although in alternate embodiments, the widths can vary), etc. After extending through turn 4 in the fourth layer, electrical path extends to turn 5 in that layer. After extending through turn 5 in the fourth layer, the electrical path extends through the substrate to turn 6, and so on, following path until reaching turn 20, and then extending to the source or sink of the current. Note that in an alternate embodiment, the path can be different as will be detailed below.

As can be seen, the heights of some of the conductors vary, thus varying the cross-sectional area. In some embodiments, this can have a similar and/or a same effect or at least some utilitarian value concomitant with the coil having varying widths (instead of the width being varied to vary the cross-sectional area, the height is varied). It is noted that while the embodiment depicted in FIG. 24 depicts an arrangement where the outer layers have a uniform height, in some alternate embodiments, the outer layers can also have a varying height. Still further, while the inner layers are depicted as having conductors having varying heights and conductors that are interleaved with each other, in some alternate embodiments, the conductors are not interleaved (e.g., the heights of the conductors facing one another are the same, only one layer has a varying height, some heights on one layer vary while others do not, etc.). Note further that in some embodiments, the widths of the conductors can also vary according to the teachings detailed herein.

In an alternate embodiment, the electrical path of FIG. 24 (not shown) extends from turn 1 in the first level to turn numeral 8 to turn numeral 9 to turn numeral 16 to turn numeral 17 and then to turn numeral 18, to 15, to 10, to 7 to 2, to 3, to 6 to 11, to 14, to 19 to 20, to 13, to 12 to 5 to 4 and then to a source or sink of the current. Note that in an alternate embodiment, the path can be different.

It is noted that while the embodiments detailed herein disclosing the weave (e.g., FIGS. 15-24) are presented in terms of a conductor having a varying width (and/or height), in an alternate embodiment, such embodiments can be implemented with a uniform width and/or height/uniform cross-section. That is, the weave concept can be utilized with a conductor that has a constant width and/or height.

It is noted that any disclosure herein of a coil or an inductance coil or an inductance component corresponds to a disclosure of an inductance antenna or an inductance communication device. That is, any of the teachings detailed herein disclosed with respect to an inductance coil also corresponds to a disclosure of an inductance antenna or an inductance communication device and/or an inductance RF communication device/antenna. Any disclosure of an inductance antenna and/or an inductance communication device corresponds to a disclosure of an inductor or an inductor coil or a coil utilized for other purposes.

In an exemplary embodiment, there is an inductance communication coil, comprising: a conductor having at least one conductive turn, wherein a width of the conductor is wider at a first location relative to that at a second location. In an exemplary embodiment, there is an inductance communication coil as described above and/or below, wherein the conductor comprises a plurality of turns, wherein the first location is at a first turn and the second location is at a second turn, and the second turn is an outer turn relative to the first turn.

In an exemplary embodiment, there is an inductance communication coil as described above and/or below, wherein the conductor comprises a plurality of turns, wherein the first location is at a first turn and the second location is at a second turn. In an exemplary embodiment, there is the inductance communication coil as described above and/or below, wherein the second turn is an outer turn relative to the first turn. In an exemplary embodiment, there is an inductance communication coil as described above and/or below, wherein the second turn is an inner turn relative to the first turn. In an exemplary embodiment of the coil described above and/or below, the third turn is an outer turn relative to the second turn; and the first turn is an outer turn relative to the second turn and the third turn. In an exemplary embodiment, the coil as described above and/or below is such that the conductor comprises a plurality of turns, wherein the first location is at a first turn and the second location is at a second turn; a width of the conductor is wider at a third location relative to that at the first location; and the third location is on one of the first or second turns.

In an exemplary embodiment, there is a transcutaneous inductance communication antenna, comprising a conductor having a non-uniform geometry.

It is noted that in an exemplary embodiment, there is a transcutaneous inductance communication antenna as detailed above and/or below, wherein the conductor is a multilayer conductor, wherein the conductor extends into the substrate and then out of the substrate a plurality of times. It is noted that in an exemplary embodiment, there is a transcutaneous inductance communication antenna as detailed above and/or below, wherein the conductor includes a first turn, a second turn and a third turn, wherein the second turn is an outer turn relative to the first turn, and the third turn is an outer turn relative to the second turn; and the second turn is wider than the width of the first turn and the width of the third turn. In an exemplary embodiment, there is a transcutaneous inductance communication antenna as detailed above and/or below, wherein the conductor includes a first turn, a second turn and a third turn, wherein the second turn is an outer turn relative to the first turn, and the third turn is an outer turn relative to the second turn; and the second turn is wider than the width of the first turn and the width of the third turn. It is noted that in an exemplary embodiment, there is a transcutaneous inductance communication antenna as detailed above and/or below, wherein the conductor includes a fourth turn that is an inner turn relative to the first turn; the conductor includes a fifth turn that is an outer turn relative to the third turn; a width of the fourth turn is narrower than the width of the first turn; and the width of the fifth turn is narrower than the width of the third turn.

In an exemplary embodiment, there is an inductance coil, comprising a conductor having a plurality of turns, wherein DC resistance of the conductor varies along a path between a first location and a second location, wherein the plurality of turns are electrically located between the first location and the second location. In an exemplary embodiment, there is an inductance coil as describe above and/or below, wherein a cross-sectional areas of the conductor on respective planes normal to a longitudinal axis of respective turns are different for at least two turns of the plurality of turns.

In an exemplary embodiment, there is a coil, comprising a conductor including a first portion extending in a first level and a second portion extending in a second level, wherein the conductor includes a third portion located on a different level than that of the second portion, wherein an electrical path of the conductor is such that the second portion is located between the first portion and the third portion. In an exemplary embodiment, there is a coil is described and/or below, wherein at least one of:

(i) the level on which the third portion is located is the first level, and the conductor includes a fourth portion extending in the first level, wherein an electrical path of the conductor is such that the fourth portion is located after the first portion, the second portion and the third portion, and a fifth portion is located between the third portion and the fourth portion, and the fifth portion is located on the second level; or (ii) with respect to at least one of a beginning or an end of a coil, a contiguous electrical path of the conductor subtends an angle totaling at least 600 degrees on a same level.

In an exemplary embodiment, there is a coil as described above and/or below, wherein the level on which the third portion is located is the first level. In an exemplary embodiment, there is a coil as described above and/or below, wherein the first, second and third portions are turns of the conductor. In an exemplary embodiment, there is a coil as described above and/or below, wherein the level on which the third portion is located is the first level. In an exemplary embodiment, there is a coil as described above and/or below, wherein the level on which the third portion is located is a level different from the first level and the second level.

In an exemplary embodiment, there is an inductance communication coil, comprising, a conductor; and a substrate, wherein the conductor alternatingly cycles through the substrate. In an exemplary embodiment, there is a coil as described above and/or below, wherein the conductor alternatingly cycles through the substrate for more than one complete cycle. In an exemplary embodiment, there is an inductance communication coil as described above and/or below, wherein the conductor is configured such that an electrical path extends through a first turn on one side of the substrate and then through a second and third turn on an opposite side of the substrate and then through a fourth and fifth turn on the one side of the substrate and then through a sixth and seventh turn on the opposite side of the substrate and then through an eighth and ninth turn on the one side of the substrate and then through at least a tenth turn on the opposite side of the substrate. In an exemplary embodiment, there is an inductance communication coil as described above and/or below, wherein the conductor is configured such that an electrical path extends through the tenth turn and then through an eleventh turn on the opposite side of the substrate.

In an exemplary embodiment, there is a coil as described above and/or below, wherein the first, second and third portions are turns of the conductor. In an exemplary embodiment, there is a coil as described above and/or below, further comprising a fourth portion corresponding to a fourth turn, wherein the fourth portion is located on the second level, and wherein the electrical path of the conductor is such that the fourth portion is located between the first portion and the third portion.

In an exemplary embodiment, there is an inductance transcutaneous communication coil, comprising: a coiled conductor including at least three turns on a first tier and a plurality of turns on a second tier different from the first tier, wherein a maximum outer diameter of the outermost turn of the at least three turns is about 30 mm, and the coiled conductor is of a configuration where a bare winding thereof, when subjected to an electrical current having a frequency of 5 MHz and a current of one amp is such that any electric field located at any location between the first tier and the second tier at the middle distance between the first tier and the second tier has a value of no more than about $4 \times 10^5$ V/m. In an exemplary embodiment, there is an inductance transcutaneous communication coil as described above and/or below, wherein any electric field located at any location between the first tier and the second tier at the middle distance between the first tier and the second tier has a value of no more than about $2 \times 10^5$ V/m. In an exemplary embodiment, there is an inductance transcutaneous communication coil as described above and/or below, wherein any electric field located at any location between the first tier and the second tier at the middle distance between the first tier and the second tier has a value of no more than about $1.5 \times 10^5$ V/m. In an exemplary embodiment, there is an inductance transcutaneous communication coil as described above and/or below, wherein the distance between the first tier and the second tier is no more than 0.6 mm, and there are at least five turns on the first tier and at least five turns on the second tier, and wherein the turns are generally circular.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is noted that any disclosure herein of a coil or an inductance coil or an inductance component corresponds to a disclosure of an inductance antenna or an inductance communication device. That is, any of the teachings detailed herein disclosed with respect to an inductance coil also corresponds to a disclosure of an inductance antenna or an inductance communication device. Any disclosure of an inductance antenna and/or an inductance communication device corresponds to a disclosure of an inductor or an inductor coil or a coil utilized for other purposes.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

It is noted that in at least some exemplary embodiments, any feature disclosed herein can be utilized in combination with any other feature disclosed herein, unless otherwise specified. Accordingly, exemplary embodiments include a medical device including one or more or all of the teachings detailed herein, in any combination.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. An inductance communication coil, comprising:
a coiled conductor including at least two turns on a first layer, wherein
a maximum outer diameter of the highest diameter turn is about 40 mm, and
the coiled conductor is of a configuration where a bare winding thereof, when subjected to an electrical current having a frequency of 5 MHz, has a Q factor of at least 75.

2. The inductance communication coil of claim 1, wherein:
the coiled conductor is of a configuration where a bare winding thereof, when subjected to an electrical current having a frequency of 5 MHz, has a Q factor of at least 80.

3. The inductance communication coil of claim 1, wherein:
the coiled conductor is of a configuration where a bare winding thereof, when subjected to an electrical current having a frequency of 5 MHz, has a Q factor of at least 94.

4. The inductance communication coil of claim 1, wherein:
the coiled conductor is of a configuration where a bare winding thereof, when subjected to an electrical current having a frequency of 5 MHz, has a Q factor of at least 85.

5. The inductance communication coil of claim 1, wherein:
the coiled conductor is of a configuration where a bare winding thereof, when subjected to an electrical current having a frequency of 5 MHz, has a Q factor of at least 90.

6. A method, comprising:
transcutaneously transmitting, using a first coiled inductance antenna located outside the skin of the recipient, an inductance signal to an implanted second coiled inductance antenna, wherein
a current is applied to the first coiled inductance antenna to generate a magnetic field, thereby transmitting the inductance signal, and
an average current density at least one of increases or decreases with distance from a geometric center of turns of the first coiled inductance antenna over at least a portion of the distance from the geometric center.

7. The method of claim 6, wherein:
the action of transmitting the inductance signal transfers at least data to the implanted second coiled inductance antenna.

8. The method of claim 6, further comprising:
evoking a sensory percept based on the inductance signal transmitted to the second coiled inductance antenna.

9. The method of claim 8, further comprising:
at least one of powering an implanted functional component that evokes the sensory percept or recharging an implanted battery that powers the implanted functional component based on the inductance signal transmitted to the second coiled inductance antenna.

10. The method of claim 8, further comprising, after transcutaneously transmitting the inductance signal:
transcutaneously transmitting, using the first coiled inductance antenna, a second inductance signal to the implanted second coiled inductance antenna; and
at least one of recharging an implanted battery or powering an implanted functional component based on a third signal from the second coiled inductance antenna, the third signal being generated by the second inductance signal.

11. The method of claim 6, wherein:
the average current density at a given cross-section of a given turn of the fist coiled inductance antenna decreases with distance from the geometric center for a portion of the distance from the geometric center and then increases with distance from the geometric center for another portion of the distance from the geometric center.

12. The method of claim 6, wherein:
the average current density decreases over a first distance from the geometric center of turns of the first coiled inductance antenna over at least a portion of the distance from the geometric center, and the average current density increases over a second distance from the geometric center of turns of the first coiled inductance antenna over a second portion of the distance from the geometric center, wherein the portion of the distance from the geometric center corresponding to the first distance is located between the geometric center and the second portion.

13. The method of claim 6, wherein:
the average current density decreases over a first distance from a geometric center of turns of the first coiled inductance antenna over at least a portion of the distance from the geometric center, and the average current density increases over a second distance from the geometric center of turns of the first coiled inductance antenna over a second portion of the distance from the geometric center, wherein the portion of the distance from the geometric center corresponding to the second distance is located between the geometric center and the first portion.

14. The method of claim 6, wherein:
the average current density decreases over a first distance from a geometric center of turns of the first coiled inductance antenna over at least a portion of the distance from the geometric center.

15. The method of claim 6, wherein:
the average current density increases over a first distance from a geometric center of turns of the first coiled inductance antenna over a portion of the distance from the geometric center.

16. The method of claim 6, wherein:

the at least one of the first coiled inductance antenna or the second coiled inductance antenna is substantially identical to at least 500 others previously provided to other recipients and used to transcutaneously communicate an inductance signal.

5

\* \* \* \* \*